(12) United States Patent
Berneth et al.

(10) Patent No.: US 10,001,703 B2
(45) Date of Patent: Jun. 19, 2018

(54) PHOTOPOLYMER FORMULATION FOR PRODUCTION OF HOLOGRAPHIC MEDIA COMPRISING BORATES WITH LOW TG

(71) Applicant: Covestro Deutschland AG, Leverkusen (DE)

(72) Inventors: Horst Berneth, Leverkusen (DE); Thomas Rölle, Leverkusen (DE); Friedrich-Karl Bruder, Krefeld (DE); Dennis Hönel, Zülpich-Wichterich (DE); Marc-Stephan Weiser, Leverkusen (DE); Thomas Fäcke, Leverkusen (DE); Rainer Hagen, Leverkusen (DE); Günther Walze, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days. days.

(21) Appl. No.: 15/029,080

(22) PCT Filed: Oct. 13, 2014

(86) PCT No.: PCT/EP2014/071877
§ 371 (c)(1),
(2) Date: Apr. 13, 2016

(87) PCT Pub. No.: WO2015/055576
PCT Pub. Date: Apr. 23, 2015

(65) Prior Publication Data
US 2016/0252808 A1 Sep. 1, 2016

(30) Foreign Application Priority Data
Oct. 17, 2013 (EP) .................................. 13189138

(51) Int. Cl.
*G03H 1/02* (2006.01)
*G03F 7/028* (2006.01)
(Continued)

(52) U.S. Cl.
CPC ............ *G03F 7/001* (2013.01); *C07C 211/63* (2013.01); *C07D 213/20* (2013.01);
(Continued)

(58) Field of Classification Search
None
See application file for complete search history.

(56) References Cited

U.S. PATENT DOCUMENTS 4,033,905 A * 7/1977 Bloom .................. H01B 1/122
252/299.2
5,153,100 A * 10/1992 Weed ........................ C08F 2/50
430/281.1
(Continued)

FOREIGN PATENT DOCUMENTS

DE 196 48 282 A1 5/1997
EP 0223587 A1 5/1987
(Continued)

OTHER PUBLICATIONS

Machine translation of JP 2000-267273 (Sep. 2000).*
(Continued)

*Primary Examiner* — Martin J Angebranndt
(74) *Attorney, Agent, or Firm* — Drinker Biddle & Reath LLP

(57) ABSTRACT

The invention relates to a photopolymer formulation comprising a component reactive toward isocyanates, a polyisocyanate component, a writing monomer and a photoinitiator containing at least one dye and a coinitiator, characterized in that the coinitiator contains at least one substance of the formula (Ia)

(Continued)

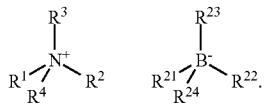

(Ia)

The invention further provides a process for preparing the specific coinitiators and the coinitiators obtainable by this process, and additionally a process for producing a holographic medium using the specific coinitiators, and a holographic medium obtainable using the inventive photopolymer formulation. The invention further relates to a laminate structure comprising an inventive holographic medium and likewise specific borates suitable as coinitiators.

14 Claims, 3 Drawing Sheets

(51) Int. Cl.
| | | |
|---|---|---|
| G03F 7/029 | (2006.01) | |
| G03F 7/035 | (2006.01) | |
| G03F 7/00 | (2006.01) | |
| C07F 5/02 | (2006.01) | |
| C07C 211/63 | (2006.01) | |
| C07D 213/20 | (2006.01) | |
| C07D 233/58 | (2006.01) | |
| C07D 295/037 | (2006.01) | |

(52) U.S. Cl.
CPC ....... *C07D 233/58* (2013.01); *C07D 295/037* (2013.01); *C07F 5/027* (2013.01); *G03F 7/029* (2013.01); *G03F 7/035* (2013.01); *G03H 1/0248* (2013.01); *G03H 2001/0264* (2013.01); *G03H 2260/12* (2013.01)

(56) References Cited

U.S. PATENT DOCUMENTS

| | | | | |
|---|---|---|---|---|
| 5,807,905 A | * | 9/1998 | Cunningham | C07F 5/027 430/269 |
| 5,932,393 A | | 8/1999 | Cunningham et al. | |
| 5,952,152 A | * | 9/1999 | Cunningham | C07F 5/027 430/281.1 |
| 6,011,180 A | | 1/2000 | Cunningham et al. | |
| 6,165,686 A | * | 12/2000 | Kamata | C09D 4/06 430/281.1 |
| 6,218,076 B1 | * | 4/2001 | Ogata | B41M 5/36 430/281.1 |
| 6,919,159 B2 | * | 7/2005 | Matsumoto | G03F 7/002 430/138 |
| 8,361,678 B2 | | 1/2013 | Weiser et al. | |
| 8,771,903 B2 | | 7/2014 | Hönel et al. | |
| 8,889,322 B2 | | 11/2014 | Weiser et al. | |
| 9,146,456 B2 | | 9/2015 | Berneth et al. | |
| 2003/0224294 A1 | * | 12/2003 | Fukushige | C08F 2/50 430/281.1 |
| 2007/0166625 A1 | * | 7/2007 | Cole | G03H 1/02 430/1 |
| 2008/0076062 A1 | * | 3/2008 | Makino | G03F 7/0045 430/270.1 |
| 2008/0312403 A1 | * | 12/2008 | Stockel | C08F 299/00 528/59 |
| 2010/0203241 A1 | * | 8/2010 | Weiser | G03F 7/028 427/162 |
| 2013/0177746 A1 | * | 7/2013 | Facke | B32B 27/40 428/195.1 |
| 2013/0224634 A1 | * | 8/2013 | Berneth | C09B 11/12 430/2 |

FOREIGN PATENT DOCUMENTS

| | | | |
|---|---|---|---|
| EP | 0475153 A1 | | 3/1992 |
| EP | 2 172 503 A1 | | 4/2010 |
| EP | 2450893 A1 | | 5/2012 |
| JP | 50-071799 | * | 6/1975 |
| JP | 09-067406 | * | 3/1997 |
| JP | H09188710 A | | 7/1997 |
| JP | 09-241614 | * | 9/1997 |
| JP | 2000267273 A | | 9/2000 |
| JP | 2003-321476 | * | 11/2003 |
| WO | WO-2011054797 A1 | | 5/2011 |
| WO | WO-2011067057 A1 | | 6/2011 |
| WO | 2012/062655 | * | 5/2012 |
| WO | WO-2012062655 A2 | | 5/2012 |

OTHER PUBLICATIONS

International Search Report for PCT/EP2014/071877 dated Jan. 23, 2015.
Kulapina et al., "Physicochemical Properties of Tetraalkylammonium Tetraphenylborates and Tetraalkylammonium Dodecylsufates", Russian Journal of Inorganic Chemistry, vol. 58, No. 1, pp. 112-116 (2013).
Third Party Observations on European Patent Application No. 14783851.0, dated Oct. 6, 2017.

* cited by examiner

PHOTOPOLYMER FORMULATION FOR PRODUCTION OF HOLOGRAPHIC MEDIA COMPRISING BORATES WITH LOW TG

CROSS-REFERENCE TO RELATED APPLICATIONS

This application is a national stage application (under 35 U.S.C. § 371) of PCT/EP2014/071877, filed Oct. 13, 2014, which claims benefit of European Application No. 13189138.4, filed Oct. 17, 2013, both of which are incorporated herein by reference in their entirety.

The invention relates to a photopolymer formulation comprising a component reactive toward isocyanates, a polyisocyanate component, a writing monomer and a photoinitiator containing at least one dye and a specific coinitiator.

The invention further provides a process for preparing the specific coinitiators and the coinitiators obtainable by this process, and additionally a process for producing a holographic medium using the specific coinitiators, and a holographic medium obtainable using the inventive photopolymer formulation. The invention further relates to a laminate structure comprising an inventive holographic medium and likewise specific borates suitable as coinitiators.

BACKGROUND OF THE INVENTION

Ammonium salts of alkyl triarylborates as coinitiators and the synthesis thereof are known. In the synthesis, which can be performed efficiently on industrial scale by the following route:

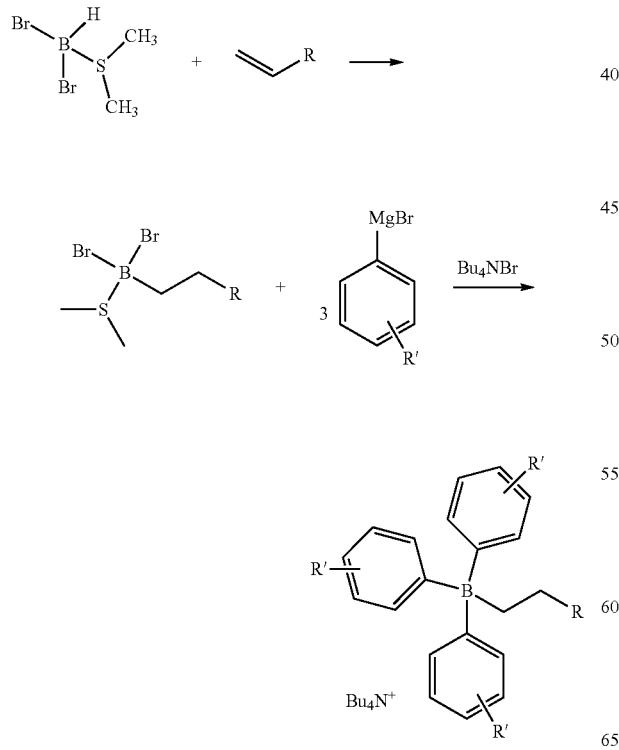

a mixture of alkyltriarylborates of the formula (A)

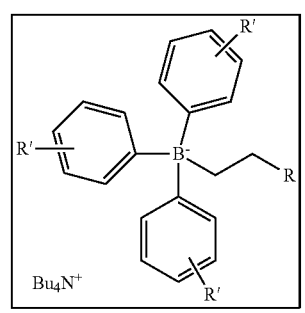

(A)

and tetraarylborates of the formula (B)

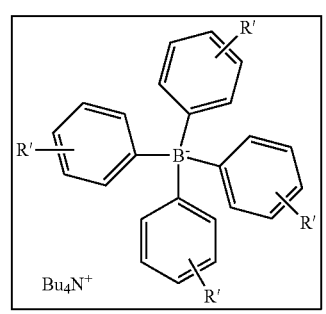

(B)

is always obtained, since the hydroboration requires tribromoborane as catalyst. If, in contrast, the mixture of alkyl triarylborates and tetraarylborates obtained in the synthesis is used as coinitiators in holographic media, inadequate long-term stability and photochemical bleachability are found. Materials of this kind are therefore unsuitable for industrial utilization. However, the separation of this mixture is complex and inevitably leads to considerable substance losses.

It was therefore an object of the present invention to provide a photopolymer composition which comprises a coinitiator which is simple and inexpensive to prepare and, at the same time, is suitable for producing holographic media having good long-term stability and photochemical bleachability. An efficient process for preparing suitable coinitiators was likewise to be provided.

BRIEF SUMMARY OF THE INVENTION

This object was achieved in accordance with the invention by a photopolymer formulation comprising a component reactive toward isocyanates, a polyisocyanate component, a writing monomer and a photoinitiator containing at least one dye and a coinitiator, characterized in that the coinitiator contains at least one substance of the formula (Ia)

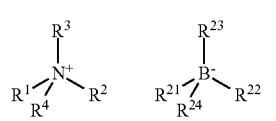

(Ia)

in which
- $R^1$ is an optionally branched $C_{14}$- to $C_{22}$-alkyl radical,
- $R^2$ is an optionally branched and/or optionally substituted $C_8$- to $C_{22}$-alkyl radical, a cyclohexyl or cycloheptyl radical, a $C_7$- to $C_{10}$-aralkyl radical, or a phenyl radical substituted by nonionic radicals, and
- $R^3$ and $R^4$ are each independently an optionally branched and/or optionally substituted $C_1$- to $C_5$-alkyl radical or
- $R^1$ is an optionally branched $C_{14}$- to $C_{22}$-alkyl radical,
- $R^2$ is an optionally branched and/or optionally substituted $C_8$- to $C_{22}$-alkyl radical or a $C_7$- to $C_{10}$-aralkyl radical and
- $R^3$ and $R^4$ together form a —(CH$_2$)$_4$—, —(CH$_2$)$_5$— or —(CH$_2$)$_2$—O—(CH$_2$)$_2$— bridge or
- $R^1$ is an optionally branched $C_{14}$- to $C_{22}$-alkyl radical and
- $R^2$, $R^3$ and $R^4$ together with the N$^+$ form an imidazole or pyridine ring substituted at least by one radical selected from $C_1$- to $C_8$-alkyl, $C_1$- to $C_8$-alkoxy, $C_5$- to $C_7$-cycloalkyl, benzyl or phenyl and in which
- $R^{21}$ is an optionally substituted $C_1$- to $C_{22}$-alkyl, $C_3$- to $C_{22}$-alkenyl, $C_5$- to $C_7$-cycloalkyl or $C_7$- to $C_{13}$-aralkyl radical and
- $R^{22}$ to $R^{24}$ are each independently a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and phenoxy.

It has now been found that, surprisingly, the inventive photopolymer formulations are suitable for production of holographic media having good long-term stability and photochemical bleachability. In addition, the coinitiators used in accordance with the invention are simple and inexpensive to prepare, since the mixture of alkyl triarylborates and tetraarylborates obtained in the above-described synthesis can be converted directly to a suitable coinitiator by a simple process. The coinitiators obtained can be used as such, without the holographic media produced having the abovementioned disadvantages. The coinitiators preferably have a glass transition temperature $T_g \leq 0°$ C.

DETAILED DESCRIPTION OF THE INVENTION

The preparation of such carbon-substituted ammonium triarylalkylborates as are suitable in particular embodiments for use as coinitiators in the inventive photopolymer formulations too is known in general terms from the prior art, specifically from JP 2000267273. However, the use of such carbon-substituted ammonium triarylalkylborates for holographic applications has not been described in the prior art.

Preferably, the coinitiators used in the inventive photopolymer formulation have a glass transition temperature $T_g$ of $\leq 0°$ C. More preferably, the $T_g$ is $\leq -10°$ C., more preferably $\leq -15°$ C., most preferably $\leq -20°$ C.

In the context of this invention, the glass transition temperature $T_g$ is determined by means of dynamic differential calorimetry based on DIN EN 61006, method A, using a DSC instrument which, for determination of $T_g$, has been calibrated with indium and lead, and conducting three successive heating runs, from $-100°$ C. to $+80°$ C. for the first run and from $-100°$ C. to $+150°$ C. for the second and third runs, at a constant heating rate of 20 K/min, with subsequent cooling at a cooling rate of 50 K/min, and using the third heating curve to determine the values. The $T_g$ is given by the temperature at half the height of a glass transition step.

Further details of preferred embodiments of these measurements are given in the methods specified in the examples section.

The coinitiators used in accordance with the invention preferably contain at least one substance of the formula (Ia) in which
- $R^1$ is an optionally branched $C_{14}$- to $C_{22}$-alkyl radical,
- $R^2$ is an optionally branched $C_8$- to $C_{22}$-alkyl radical, a cyclohexyl or cycloheptyl radical, a phenyl-$C_1$- to $C_3$-alkyl radical or a phenyl radical substituted by at least one radical selected from $C_1$- to $C_8$-alkyl, $C_1$- to $C_8$-alkoxy, fluorine, chlorine, trifluoromethyl, trifluoromethoxy, $C_5$- to $C_7$-cycloalkyl, benzyl, phenyl and phenoxy and
- $R^3$ and $R^4$ are each independently methyl, ethyl, propyl, butyl, chloroethyl, hydroxyethyl or cyanoethyl or
- $R^1$ is an optionally branched $C_{14}$- to $C_{22}$-alkyl radical,
- $R^2$ is an optionally branched $C_8$- to $C_{22}$-alkyl radical or a phenyl-$C_1$- to $C_3$-alkyl radical and
- $R^3$ and $R^4$ together form a —(CH$_2$)$_4$—, —(CH$_2$)$_5$— or —(CH$_2$)$_2$—O—(CH$_2$)$_2$— bridge or
- $R^1$ is an optionally branched $C_{14}$- to $C_{22}$-alkyl radical and
- $R^2$, $R^3$ and $R^4$ together with the N atom form an imidazole or pyridine ring substituted at least by one radical selected from $C_1$- to $C_8$-alkyl, $C_1$- to $C_8$-alkoxy, $C_5$- to $C_7$-cycloalkyl, benzyl or phenyl.

Particular preference is given to substances of the formula (Ia)
in which
- $R^1$ is tetradecyl, hexadecyl, octadecyl, eicosyl or docosyl,
- $R^2$ is octyl, 2-ethylhexyl, nonyl, decyl, dodecyl, tetradecyl, hexadecyl, octadecyl, eicosyl, docosyl, cyclohexyl, cycloheptyl, benzyl, 2-phenylethyl, 2- or 3-phenylpropyl or a phenyl radical substituted by at least one radical in the 3, 4 and/or 5 position, selected from $C_4$- to $C_8$-alkyl, $C_4$- to $C_8$-alkoxy, trifluoromethyl, trifluoromethoxy, $C_5$- to $C_7$-cycloalkyl, benzyl, phenyl and phenoxy, and
- $R^3$ and $R^4$ are each independently methyl or ethyl or
- $R^1$ is tetradecyl, hexadecyl, octadecyl, eicosyl or docosyl,
- $R^2$ is octyl, 2-ethylhexyl, nonyl, decyl, dodecyl, tetradecyl, hexadecyl, octadecyl, eicosyl, docosyl, benzyl, 2-phenylethyl, 2- or 3-phenylpropyl and
- $R^3$ and $R^4$ together form a —(CH$_2$)$_4$—, —(CH$_2$)$_5$— or —(CH$_2$)$_2$—O—(CH$_2$)$_2$— bridge or
- $R^1$ is tetradecyl, hexadecyl, octadecyl, eicosyl or docosyl and
- $R^2$, $R^3$ and $R^4$ together with the N atom form an imidazole or pyridine ring substituted at least by one radical selected from methyl, ethyl, 1- or 2-propyl, 1- or 2-butyl, 1,1-dimethylethyl, 1-pentyl, 1-hexyl, 1-octyl, methoxy, ethoxy, 1- or 2-propoxy, 1- or 2-butoxy, 1,1-dimethylethoxy, 1-pentoxy, 1-hexyloxy, cyclopentyl, cyclohexyl, benzyl and phenyl.

Very particular preference is given to substances of the formula (Ia)
in which
- $R^1$ is hexadecyl or octadecyl,
- $R^2$ is octyl, 2-ethylhexyl, decyl, dodecyl, tetradecyl, hexadecyl, octadecyl, benzyl, 3-phenylpropyl or a phenyl radical substituted by at least one radical in the 3, 4 and/or 5 position, selected from 1- or 2-butyl, 1,1-dimethylethyl, 1-pentyl, 1-hexyl, 1-octyl, 1- or 2-butoxy, 1,1-dimethylethoxy, 1-pentoxy, 1-hexoxy, 1-octoxy, trifluoromethyl, trifluoromethoxy, cyclohexyl, benzyl, phenyl and phenoxy, and $R^3$ and $R^4$ are each independently methyl or $R^1$ is hexadecyl or octadecyl, $R^2$ is octyl, 2-ethylhexyl, decyl, dodecyl, tetradecyl, hexadecyl, octadecyl, benzyl or 3-phenylpropyl and $R^3$ and $R^4$ together form a —(CH$_2$)$_4$—, —(CH$_2$)$_5$— or —(CH$_2$)$_2$—O—(CH$_2$)$_2$— bridge or $R^1$ is hexadecyl or octadecyl and $R^2$, $R^3$ and $R^4$ together with the N$^+$ atom form an imidazole ring wherein the second nitrogen atom is substituted by 1- or 2-butyl, 1-pentyl, 1-hexyl, 1-octyl, cyclopentyl, cyclohexyl, benzyl or phenyl, or a pyridine ring with the ring substituted at least by one radical selected from 1- or 2-butyl, 1,1-dimethylethyl, 1-pentyl, 1-hexyl, 1- or 2-butoxy, 1,1-dimethylethoxy, 1-pentoxy, 1-hexyloxy, cyclopentyl, cyclohexyl, benzyl and phenyl.

Preference is given to using, in the inventive photopolymer formulation, coinitiators containing at least one substance of the formula (Ia) wherein the $R^{22}$ to $R^{24}$ radicals are the same. Further preferably, the substituents in the $R^{22}$ to $R^{24}$ radicals are in the 3, 4 and/or 5 position, more preferably in the 3 or 4 position or in the 3,4 arrangement.

Preference is also given to coinitiators containing at least one substance of the formula (Ia) where $R^{21}$ is an optionally branched and optionally fluorine-, chlorine-, methoxy-, ethoxy- or cyano-substituted C$_2$- to C$_{18}$-alkyl, C$_3$- to C$_{12}$-alkenyl or C$_7$ to C$_{10}$-aralkyl radical, cyclopentyl or cyclohexyl and $R^{22}$ to $R^{24}$ are each independently a C$_6$- to C$_{10}$-aryl radical substituted by at least one radical selected from fluorine, chlorine, C$_1$- to C$_4$-alkyl, trifluoromethyl, C$_1$- to C$_4$-alkoxy, trifluoromethoxy, phenyl and phenoxy.

Particular preference is given to coinitiators containing at least one substance of the formula (Ia) where $R^{21}$ is 1- or 2-butyl, 1,1-dimethylethyl, 1- or 2-pentyl, 1- or 2-hexyl, 1- or 2-heptyl, 1- or 2-octyl, 2-ethylhexyl, 1- or 2-nonyl, 1- or 2-decyl, 1-dodecyl, 1-tetradecyl, 1-hexadecyl, 1-octadecyl, allyl, 2-buten-1-yl, benzyl, 2-phenylethyl, 2- or 3-phenylpropyl, cyclopentyl or cyclohexyl and $R^{22}$ to $R^{24}$ are each independently a phenyl radical optionally substituted in the 3 and/or 4 position by at least one radical selected from fluorine, chlorine, methyl, tert-butyl, trifluoromethyl, methoxy and trifluoromethoxy.

Very particular preference is given to coinitiators containing at least one substance of the formula (Ia) where $R^{21}$ is 1-butyl, 1-pentyl, 1-hexyl, 1-heptyl, 1-octyl, 1-nonyl, 1-decyl, 1-dodecyl, 1-tetradecyl, 1-hexadecyl, 1-octadecyl, allyl, 3-phenylpropyl, cyclopentyl or cyclohexyl and $R^{22}$ to $R^{24}$ are each 4-fluorophenyl, 4-chlorophenyl, 4-tert-butylphenyl, 3-fluoro-4-methylphenyl or 3-chloro-4-methylphenyl and $R^{22}$ to $R^{24}$ are the same.

Preference is further given to coinitiators containing at least one substance of the formula (Ia) where $R^{21}$ is 1-butyl, 1-hexyl, 1-octyl, 1-dodecyl or 3-phenylpropyl, $R^{22}$ to $R^{24}$ are each 4-fluorophenyl, 4-chlorophenyl, 3-fluoro-4-methylphenyl or 3-chloro-4-methylphenyl and $R^{22}$ to $R^{24}$ are the same.

In a preferred embodiment of the invention, the coinitiators used in the inventive photopolymer formulations further comprise at least one substance of the formula (Ib)

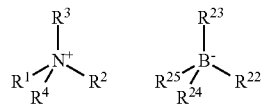

(Ib)

in which $R^1$ to $R^4$ are each as defined in Claim 1 and $R^{22}$ to $R^{25}$ are each independently a C$_6$- to C$_{10}$-aryl radical optionally substituted by at least one radical selected from halogen, C$_1$- to C$_4$-alkyl, trifluoromethyl, C$_1$- to C$_4$-alkoxy, trifluoromethoxy, phenyl and phenoxy.

The coinitiators used in accordance with the invention contain the substances of the formulae (Ia) and (Ib) preferably in a molar ratio of 80:20 to 99.99:0.01, more preferably 90:10 to 99.95:0.05, even more preferably 95:5 to 99.9:0.1 and further preferably 97:3 to 99.9:0.1.

In a preferred embodiment, the coinitiator consists of the substance of the formula (Ia) or a mixture of the substances of the formulae (Ia) and (Ib).

For the $R^1$ to $R^4$ and $R^{22}$ to $R^{24}$ radicals in the substances of the formula (Ib), the preferred embodiments cited above for the substances of the formula (Ia) apply likewise. For $R^{25}$ in the formula (Ib), the preferred embodiments of $R^{22}$, $R^{23}$ or $R^{24}$ detailed above with regard to substances of the formula (Ia) apply likewise.

In a further preferred embodiment of the invention, the coinitiator additionally also contains salts of the formula (II)

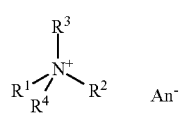

(II)

in which

An$^-$ is an anion having an AC log P in the range from 2 to 8, preferably 3 to 6, more preferably 3.5 to 5 and $R^1$ to $R^4$ are each as defined above for the substances of the formula (Ia).

For $R^1$ to $R^4$ in the salts of the formula (II), the preferred embodiments cited above for substances of the formula (Ia) with regard to $R^1$ to $R^4$ apply likewise.

It has been found that, surprisingly, particularly suitable anions An$^-$ are those which have an AC log P in the range from 2 to 8, preferably 3 to 6, more preferably 3.5 to 5.

The AC log P is calculated according to J. Comput. Aid. Mol. Des. 2005, 19, 453; Virtual Computational Chemistry Laboratory, http://www.vcclab.org.

The coinitiators used in accordance with the invention may therefore contain or consist of mixtures of borates and salts having anions of the formula An$^-$ with the inventive ammonium cations. In a preferred embodiment of the invention, the coinitiator contains a mixture of substances of the formulae (Ia), (Ib) and (II) or substances of the formulae (Ia) and (II); further preferably, the coinitiator consists of a mixture of substances of the formulae (Ia), (Ib) and (II) or substances of the formulae (Ia) and (II).

The coinitiator contains preferably 0.01 to 10% by weight, more preferably 0.05 to 7% by weight and most preferably 1 to 5% by weight of the salts of the formula (II), based on the total mass of the coinitiator.

Examples of suitable anions An⁻ are:

| Anion | AClogP |
|---|---|
| CH₃(CH₂)₁₁OSO₃⁻ (dodecyl sulfate) | 3.05 |
| Perfluorooctyl sulfate (C₈F₁₇OSO₃⁻) | 3.32 |
| Secondary alkyl sulfonate (C₆H₁₃CH(SO₃⁻)C₇H₁₅-type) | 3.45 |
| Bis(1H,1H,7H-perfluoroheptyl) sulfosuccinate | 3.62 |
| Bis(2-ethylhexyl) sulfosuccinate | 3.67 |
| 4-(alkyl)benzenesulfonate (secondary alkyl branched) | 4.85 |
| Propyl oleate / alkenyl sulfonate structure | 5.78 |

In a further preferred embodiment of the invention, the anion An⁻ has a molar mass M≥150 g/mol and more preferably ≥250 g/mol.

The anion of the formula An⁻ may preferably comprise at least one phosphorus or sulphur atom, preferably at least one sulphur atom and more preferably a sulphur atom in an $SO_3$ moiety.

Likewise preferably, the anion An⁻ may include at least one linear or branched aliphatic radical, preferably a linear or branched aliphatic $C_8$ to $C_{18}$ radical. If the anion contains more than one linear or branched aliphatic radical, these together contain 8 to 36, preferably 8 to 24, carbon atoms. This aliphatic radical may bear substituents such as fluorine, methoxy or ethoxy.

Very particularly preferred anions of the formula An⁻ consequently have a molar mass of ≥250 g/mol and contain an $SO_3^-$ moiety and at least one alkyl group having at least 8 carbon atoms, and have an AC log P in the range of 3 to 6, preferably 3.5 to 5.

The inventive anions of the formula An⁻ especially also comprise the following substances, provided that the AC log P value thereof is in the range of 2 to 8:

$C_8$- to $C_{25}$-alkanesulphonate, preferably $C_{13}$- to $C_{25}$-alkanesulphonate, $C_6$- to $C_{18}$-perfluoroalkanesulphonate, preferably $C_6$- to $C_{18}$-perfluoroalkanesulphonate, $C_9$- to $C_{25}$-alkanoate, $C_9$- to $C_{25}$-alkenoate, $C_8$- to $C_{25}$-alkylsulphate, preferably $C_{13}$- to $C_{25}$-alkylsulphate, $C_8$- to $C_{25}$-alkenylsulphate, preferably $C_{13}$- to $C_{25}$-alkenylsulphate, $C_6$- to $C_{18}$-perfluoroalkylsulphate, preferably $C_4$- to $C_{18}$-perfluoroalkylsulphate, polyether sulphates based on at least 4 equivalents of ethylene oxide and/or equivalents 4 of propylene oxide, bis($C_4$- to $C_{25}$-alkyl, $C_5$- to $C_7$-cycloalkyl, $C_3$- to $C_8$-alkenyl or $C_7$- to $C_{11}$-aralkyl)sulphosuccinate, bis-$C_2$- to $C_{10}$-alkylsulphosuccinate substituted by at least 8 fluorine atoms, $C_8$- to $C_{25}$-alkylsulphoacetates, benzenesulphonate substituted by at least one radical from the group of $C_8$- to $C_{25}$-alkyl, perfluoro-$C_6$- to $C_{12}$-alkyl and/or $C_8$- to $C_{18}$-alkoxycarbonyl, sulphonated or sulphated, optionally at least monounsaturated $C_8$ to $C_{25}$ fatty acid esters of aliphatic $C_1$- to $C_8$-alcohols or glycerol, bis(sulpho-$C_2$- to $C_6$-alkyl)-$C_3$- to $C_{12}$-alkanedicarboxylic esters, bis(sulpho-$C_2$- to $C_6$-alkyl)itaconic esters, (sulpho-$C_2$- to $C_6$-alkyl)-$C_6$- to $C_{18}$-alkanecarboxylic esters, (sulpho-$C_2$- to $C_6$-alkyl)acrylic or methacrylic esters, where, in the case of polyvalent anions, An– represents one equivalent of this anion, and where the alkane and alkyl groups may be branched and/or may be substituted by halogen, cyano, methoxy, ethoxy, methoxycarbonyl or ethoxycarbonyl.

Particular preference is given to:
sec-$C_{11}$- to $C_{18}$-alkanesulphonate, $C_{13}$- to $C_{25}$-alkylsulphate, branched $C_8$- to $C_{25}$-alkylsulphate, optionally branched bis-$C_6$- to $C_{25}$-alkylsulphosuccinate, biscyclopentyl- or -cyclohexylsulphosuccinate, sec- or tert-$C_8$- to $C_{25}$-alkylbenzenesulphonate, sulphonated or sulphated, optionally at least monounsaturated $C_8$ to $C_{25}$ fatty acid esters of aliphatic $C_1$- to $C_8$-alcohols or glycerol, bis(sulpho-$C_2$- to $C_6$-alkyl)-$C_3$- to $C_{12}$-alkanedicarboxylic esters, (sulpho-$C_2$- to $C_6$-alkyl)-$C_6$- to $C_{18}$-alkanecarboxylic esters.

Very particular preference is given to: bis(1-hexyl)sulphosuccinate, bis(1-octyl)sulphosuccinate, bis(2-ethylhexyl)sulphosuccinate, biscyclohexylsulphosuccinate, 4-n-dodecylbenzenesulphonate, 4-s-dodecylbenzenesulphonate, 4-branched-dodecylbenzenesulphonate, dodecylsulphate, tetradecylsulphate, hexadecylsulphate, octadecylsulphate.

Photopolymer formulations in a further embodiment are characterized in that the coinitiator additionally contains substances of the formulae (IIIa) and optionally (IIIb)

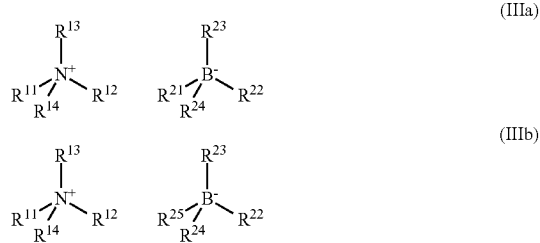

in which
$R^{11}$ to $R^{14}$ are each independently $C_1$- to $C_4$-alkyl and $R^{21}$ to $R^{24}$ are each as defined above for formula (Ia) and $R^{25}$ is as defined above for formula (Ib).

In this context, for $R^{21}$ to $R^{25}$, the preferred embodiments specified above for $R^{21}$ to $R^{25}$ with regard to the formulae (Ia) and (Ib) apply likewise.

The coinitiators used in accordance with the invention contain the substances of the formulae (IIIa) and (IIIb) preferably in a molar ratio of 80:20 to 99.99:0.01, more preferably 90:10 to 99.95:0.05, even more preferably 95:5 to 99.9:0.1 and further preferably 97:3 to 99.9:0.1.

At the same time, the coinitiator contains the substances (IIIa) and (IIIb) preferably in the same molar ratio relative to one another in which the substances (Ia) and (Ib) are also present relative to one another.

In a preferred embodiment of the invention, the coinitiator consists of a mixture of the substances of the formulae (Ia), (Ib), (IIIa) and (IIIb) or (Ia) and (IIIa), more preferably of a mixture of the substances (Ia) and (IIIa).

The molar ratio of the substances (IIIa) and optionally (IIIb) to the sum total of the substances (Ia) and optionally (Ib) is preferably ≤15:85, more preferably ≤10:90, even more preferably ≤5:95 and further preferably ≤2:98. Preferably, the molar ratio of the substances (IIIa) and optionally (IIIb) to the sum total of the substances (Ia) and optionally (Ib), however, is ≥0.01:99.99, more preferably ≥0.05:99.95 and even more preferably ≥0.10:99.90.

The coinitiator used in accordance with the invention may also contain or consist of a mixture of the substances of the formulae (Ia), (Ib), (IIIa) and (IIIb) with salts of the formula (II). Equally, the coinitiator used in accordance with the invention may contain or consist of a mixture of substances of the formulae (Ia) and (IIIa) with salts of the formula (II). These mixtures too contain preferably 0.01 to 10% by weight, more preferably 0.05 to 7% by weight and most preferably 1 to 5% by weight of the salts of the formula (II), based on the total mass of the coinitiator.

Photopolymer Formulation

Suitable photopolymer formulations suitable for the production of a photopolymer layer are likewise known to those skilled in the art and are described, for example, in WO-A 2011/054797 and WO 2011/067057. In this case, the photopolymer formulation for the production of the photopolymer layer is one comprising a polyisocyanate component a), an isocyanate-reactive component b), a writing monomer and a photoinitiator.

The polyisocyanate component a) comprises at least one organic compound having at least two NCO groups. These organic compounds may especially be monomeric di- and triisocyanates, polyisocyanates and/or NCO-functional prepolymers. The polyisocyanate component a) may also contain or consist of mixtures of monomeric di- and triisocyanates, polyisocyanates and/or NCO-functional prepolymers.

Monomeric di- and triisocyanates used may be any of the compounds that are well known per se to those skilled in the art, or mixtures thereof. These compounds may have aromatic, araliphatic, aliphatic or cycloaliphatic structures. The monomeric di- and triisocyanates may also comprise minor amounts of monoisocyanates, i.e. organic compounds having one NCO group.

Examples of suitable monomeric di- and triisocyanates are butane 1,4-diisocyanate, pentane 1,5-diisocyanate, hexane 1,6-diisocyanate (hexamethylene diisocyanate, HDI), 2,2,4-trimethylhexamethylene diisocyanate and/or 2,4,4-trimethylhexamethylene diisocyanate (TMDI), isophorone diisocyanate (IPDI), 1,8-diisocyanato-4-(isocyanatomethyl)octane, bis(4,4'-isocyanatocyclohexyl)methane and/or bis(2',4-isocyanatocyclohexyl)methane and/or mixtures thereof having any isomer content, cyclohexane 1,4-diisocyanate, the isomeric bis(isocyanatomethyl)cyclohexanes, 2,4- and/or 2,6-diisocyanato-1-methylcyclohexane (hexahydrotolylene 2,4- and/or 2,6-diisocyanate, $H_6$-TDI), phenylene 1,4-diisocyanate, tolylene 2,4- and/or 2,6-diisocyanate (TDI), naphthylene 1,5-diisocyanate (NDI), diphenylmethane 2,4'- and/or 4,4'-diisocyanate (MDI), 1,3-bis(isocyanatomethyl)benzene (XDI) and/or the analogous 1,4 isomers or any desired mixtures of the aforementioned compounds.

Suitable polyisocyanates are also compounds which have urethane, urea, carbodiimide, acylurea, amide, isocyanurate, allophanate, biuret, oxadiazinetrione, uretdione and/or iminooxadiazinedione structures and are obtainable from the aforementioned di- or triisocyanates.

More preferably, the polyisocyanates are oligomerized aliphatic and/or cycloaliphatic di- or triisocyanates, it being possible to use especially the above aliphatic and/or cycloaliphatic di- or triisocyanates.

Very particular preference is given to polyisocyanates having isocyanurate, uretdione and/or iminooxadiazinedione structures, and biurets based on HDI or mixtures thereof.

Suitable prepolymers contain urethane and/or urea groups, and optionally further structures formed through modification of NCO groups as specified above. Prepolymers of this kind are obtainable, for example, by reaction of the abovementioned monomeric di- and triisocyanates and/or polyisocyanates a1) with isocyanate-reactive compounds b1).

Isocyanate-reactive compounds b1) used may be alcohols, amino or mercapto compounds, preferably alcohols. These may especially be polyols. Most preferably, isocyanate-reactive compounds b1) used may be polyester polyols, polyether polyols, polycarbonate polyols, poly(meth)acrylate polyols and/or polyurethane polyols.

Suitable polyester polyols are, for example, linear polyester diols or branched polyester polyols, which can be obtained in a known manner by reaction of aliphatic, cycloaliphatic or aromatic di- or polycarboxylic acids or anhydrides thereof with polyhydric alcohols of OH functionality ≥2. Examples of suitable di- or polycarboxylic acids are polybasic carboxylic acids such as succinic acid, adipic acid, suberic acid, sebacic acid, decanedicarboxylic acid, phthalic acid, terephthalic acid, isophthalic acid, tetrahydrophthalic acid or trimellitic acid, and acid anhydrides such as phthalic anhydride, trimellitic anhydride or succinic anhydride, or any desired mixtures thereof. The polyester polyols may also be based on natural raw materials such as castor oil. It is likewise possible that the polyester polyols are based on homo- or copolymers of lactones, which can preferably be obtained by addition of lactones or lactone mixtures, such as butyrolactone, ε-caprolactone and/or methyl-ε-caprolactone onto hydroxy-functional compounds such as polyhydric alcohols of OH functionality ≥2, for example of the abovementioned type.

Examples of suitable alcohols are all polyhydric alcohols, for example the $C_2$-$C_{12}$ diols, the isomeric cyclohexanediols, glycerol or any desired mixtures thereof.

Suitable polycarbonate polyols are obtainable in a manner known per se by reaction of organic carbonates or phosgene with diols or diol mixtures.

Suitable organic carbonates are dimethyl, diethyl and diphenyl carbonate.

Suitable diols or mixtures comprise the polyhydric alcohols of OH functionality ≥2 mentioned per se in the context of the polyester segments, preferably butane-1,4-diol, hexane-1,6-diol and/or 3-methylpentanediol. It is also possible to convert polyester polyols to polycarbonate polyols.

Suitable polyether polyols are polyaddition products, optionally of blockwise structure, of cyclic ethers onto OH- or NH-functional starter molecules.

Suitable cyclic ethers are, for example, styrene oxides, ethylene oxide, propylene oxide, tetrahydrofuran, butylene oxide, epichlorohydrin, and any desired mixtures thereof.

Starters used may be the polyhydric alcohols of OH functionality ≥2 mentioned per se in the context of the polyester polyols, and also primary or secondary amines and amino alcohols.

Preferred polyether polyols are those of the aforementioned type based exclusively on propylene oxide, or random or block copolymers based on propylene oxide with further 1-alkylene oxides. Particular preference is given to propylene oxide homopolymers and random or block copolymers containing oxyethylene, oxypropylene and/or oxybutylene units, where the proportion of the oxypropylene units based on the total amount of all the oxyethylene, oxypropylene and oxybutylene units amounts to at least 20% by weight, preferably at least 45% by weight. Oxypropylene and oxybutylene here encompasses all the respective linear and branched $C_3$ and $C_4$ isomers.

Additionally suitable as constituents of the polyol component b1), as polyfunctional, isocyanate-reactive compounds, are also low molecular weight (i.e. with molecular weights ≤500 g/mol), short-chain (i.e. containing 2 to 20 carbon atoms), aliphatic, araliphatic or cycloaliphatic di-, tri- or polyfunctional alcohols.

These may, for example, in addition to the abovementioned compounds, be neopentyl glycol, 2-ethyl-2-butylpropanediol, trimethylpentanediol, positionally isomeric diethyloctanediols, cyclohexanediol, 1,4-cyclohexanedimethanol, 1,6-hexanediol, 1,2- and 1,4-cyclohexanediol, hydrogenated bisphenol A, 2,2-bis(4-hydroxycyclohexyl)propane or 2,2-dimethyl-3-hydroxypropyl 2,2-dimethyl-3-hydroxypropionate. Examples of suitable triols are trimethylolethane, trimethylolpropane or glycerol. Suitable higher-functionality alcohols are di(trimethylolppane), pentaerythritol, dipentaerythritol or sorbitol.

It is especially preferable when the polyol component is a difunctional polyether, polyester, or a polyether-polyester block copolyester or a polyether-polyester block copolymer having primary OH functions.

It is likewise possible to use amines as isocyanate-reactive compounds b1). Examples of suitable amines are ethylenediamine, propylenediamine, diaminocyclohexane, 4,4'-dicyclohexylmethanediamine, isophoronediamine (IPDA), difunctional polyamines, for example the Jeffamines®, amine-terminated polymers, especially having number-average molar masses ≤10 000 g/mol. Mixtures of the aforementioned amines can likewise be used.

It is likewise possible to use amino alcohols as isocyanate-reactive compounds b1). Examples of suitable amino alcohols are the isomeric aminoethanols, the isomeric aminopropanols, the isomeric aminobutanols and the isomeric aminohexanols, or any desired mixtures thereof.

All the aforementioned isocyanate-reactive compounds b1) can be mixed with one another as desired.

It is also preferable when the isocyanate-reactive compounds b1) have a number-average molar mass of ≥200 and ≤10 000 g/mol, further preferably ≥500 and ≤8000 g/mol and most preferably ≥800 and ≤5000 g/mol. The OH functionality of the polyols is preferably 1.5 to 6.0, more preferably 1.8 to 4.0.

The prepolymers of the polyisocyanate component a) may especially have a residual content of free monomeric di- and triisocyanates of <1% by weight, more preferably <0.5% by weight and most preferably <0.3% by weight.

It is optionally also possible that the polyisocyanate component a) contains, entirely or in part, organic compound whose NCO groups have been fully or partly reacted with blocking agents known from coating technology. Example of blocking agents are alcohols, lactams, oximes, malonic esters, pyrazoles, and amines, for example butanone oxime, diisopropylamine, diethyl malonate, ethyl acetoacetate, 3,5-dimethylpyrazole, ε-caprolactam, or mixtures thereof.

It is especially preferable when the polyisocyanate component a) comprises compounds having aliphatically bonded NCO groups, aliphatically bonded NCO groups being understood to mean those groups that are bonded to a primary carbon atom.

The isocyanate-reactive component b) preferably comprises at least one organic compound having an average of at least 1.5 and preferably 2 to 3 isocyanate-reactive groups. In the context of the present invention, isocyanate-reactive groups are regarded as being preferably hydroxyl, amino or mercapto groups.

The isocyanate-reactive component may especially comprise compounds having a numerical average of at least 1.5 and preferably 2 to 3 isocyanate-reactive groups.

Suitable polyfunctional, isocyanate-reactive compounds of the component b) are, for example, the above-described compounds b1), including all the preferred embodiments mentioned for the component b1).

Further examples of suitable polyethers and processes for preparation thereof are described in EP 2 172 503 A1, the disclosure of which in this regard is hereby incorporated by reference.

Reaction of the polyisocyanate component a) with the isocyanate-reactive component b) gives rise to a polymeric matrix material. More preferably, this matrix material is consisting of addition products of butyrolactone, ε-caprolactone and/or methyl-ε-caprolactone onto polyether polyols of a functionality of ≥1.8 and ≤3.1 having number-average molar masses of ≥200 and ≤4000 g/mol in conjunction with isocyanurates, uretdiones, iminooxadiazinediones and/or other oligomers based on HDI. Very particular preference is given to addition products of ε-caprolactone onto poly (tetrahydrofurans) having a functionality of ≥1.9 and ≤2.2 and number-average molar masses of ≥500 and ≤2000 g/mol, especially of ≥600 and ≤1400 g/mol, having a total number-average molar mass of ≥800 and ≤4500 g/mol, especially of ≥1000 and ≤3000 g/mol, in conjunction with oligomers, isocyanurates and/or iminooxadiazinediones based on HDI.

In a further preferred embodiment, the writing monomer comprises or consists of at least one mono- and/or one multifunctional writing monomer. Further preferably, the writing monomer may comprise or consist of at least one mono- and/or one multifunctional (meth)acrylate writing monomers. Most preferably, the writing monomer may comprise or consist of at least one mono- and/or one multifunctional urethane (meth)acrylate.

Suitable acrylate writing monomers are especially compounds of the general formula (IV)

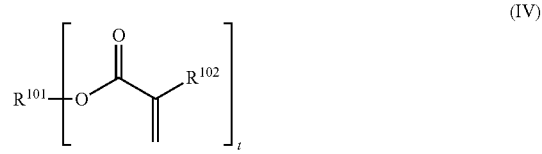

in which t≥1 and t≤4 and $R^{101}$ is a linear, branched, cyclic or heterocyclic organic radical which is unsubstituted or else optionally substituted by heteroatoms and/or $R^{102}$ is hydrogen or a linear, branched, cyclic or heterocyclic organic radical which is unsubstituted or else optionally substituted by heteroatoms. More preferably, $R^{102}$ is hydrogen or methyl and/or $R^{101}$ is a linear, branched, cyclic or heterocyclic organic radical which is unsubstituted or else optionally substituted by heteroatoms.

Acrylates and methacrylates refer, respectively, to esters of acrylic acid and methacrylic acid. Examples of acrylates and methacrylates usable with preference are phenyl acrylate, phenyl methacrylate, phenoxyethyl acrylate, phenoxyethyl methacrylate, phenoxyethoxyethyl acrylate, phenoxyethoxyethyl methacrylate, phenylthioethyl acrylate, phenylthioethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, bisphenol A diacrylate, bisphenol A dimethacrylate, and the ethoxylated analogue compounds thereof, N-carbazolyl acrylates.

Urethane acrylates are understood to mean compounds having at least one acrylic ester group and at least one urethane bond. Compounds of this kind can be obtained, for example, by reacting a hydroxy-functional acrylate or methacrylate with an isocyanate-functional compound.

Examples of isocyanate-functional compounds usable for this purpose are monoisocyanates, and the monomeric diisocyanates, triisocyanates and/or polyisocyanates mentioned under a). Examples of suitable monoisocyanates are phenyl isocyanate, the isomeric methylthiophenyl isocyanates. Di-, tri- or polyisocyanates have been mentioned above, and also triphenylmethane 4,4',4''-triisocyanate and tris(p-isocyanatophenyl) thiophosphate or derivatives thereof with urethane, urea, carbodiimide, acylurea, isocyanurate, allophanate, biuret, oxadiazinetrione, uretdione, iminooxadiazinedione structure and mixtures thereof. Preference is given to aromatic di-, tri- or polyisocyanates.

Useful hydroxy-functional acrylates or methacrylates for the preparation of urethane acrylates include, for example, compounds such as 2-hydroxyethyl (meth)acrylate, polyethylene oxide mono(meth)acrylates, polypropylene oxide mono(meth)acrylates, polyalkylene oxide mono(meth)acrylates, poly(ε-caprolactone) mono(meth)acrylates, for example Tone® M100 (Dow, Schwalbach, DE), 2-hydroxypropyl (meth)acrylate, 4-hydroxybutyl (meth)acrylate, 3-hydroxy-2,2-dimethylpropyl (meth)acrylate, hydroxypropyl (meth)acrylate, 2-hydroxy-3-phenoxypropyl acrylate, the hydroxy-functional mono-, di- or tetraacrylates of polyhydric alcohols such as trimethylolpropane, glycerol, pentaerythritol, dipentaerythritol, ethoxylated, propoxylated or alkoxylated trimethylolpropane, glycerol, pentaerythritol, dipentaerythritol or the technical mixtures thereof. Preference is given to 2-hydroxyethyl acrylate, hydroxypropyl acrylate, 4-hydroxybutyl acrylate and poly(ε-caprolactone) mono(meth)acrylate.

It is likewise possible to use the fundamentally known hydroxyl-containing epoxy (meth)acrylates having OH contents of 20 to 300 mg KOH/g or hydroxyl-containing polyurethane (meth)acrylates having OH contents of 20 to 300 mg KOH/g or acrylated polyacrylates having OH contents of 20 to 300 mg KOH/g and mixtures thereof, and mixtures with hydroxyl-containing unsaturated polyesters and mixtures with polyester (meth)acrylates or mixtures of hydroxyl-containing unsaturated polyesters with polyester (meth)acrylates.

Preference is given especially to urethane acrylates obtainable from the reaction of tris(p-isocyanatophenyl) thiophosphate and/or m-methylthiophenyl isocyanate with alcohol-functional acrylates such as hydroxyethyl (meth)acrylate, hydroxypropyl (meth)acrylate and/or hydroxybutyl (meth)acrylate.

It is likewise possible that the writing monomer comprises or consists of further unsaturated compounds such as α,β-unsaturated carboxylic acid derivatives, for example maleates, fumarates, maleimides, acrylamides, and also vinyl ethers, propenyl ethers, allyl ethers and compounds containing dicyclopentadienyl units, and also olefinically unsaturated compounds, for example styrene, α-methylstyrene, vinyltoluene and/or olefins.

In a further preferred embodiment, the photopolymer formulation additionally contains urethanes as additives, in which case the urethanes may especially be substituted by at least one fluorine atom.

Preferably, the urethanes may have the general formula (V)

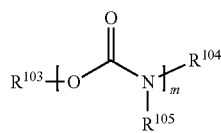

(V)

in which m≥1 and m≤8 and $R^{103}$ is a linear, branched, cyclic or heterocyclic organic radical which is unsubstituted or else optionally substituted by heteroatoms and/or $R^{104}$, $R^{105}$ are each independently hydrogen, in which case preferably at least one of the $R^{103}$, $R^{104}$, $R^{105}$ radicals is substituted by at least one fluorine atom and, more preferably, $R^{103}$ is an organic radical having at least one fluorine atom. More preferably, $R^{105}$ is a linear, branched, cyclic or heterocyclic organic radical which is unsubstituted or else optionally substituted by heteroatoms, for example fluorine.

Photoinitiators are compounds activatable typically by means of actinic radiation, which can trigger polymerization of the writing monomers. In the case of the photoinitiators, a distinction can be made between unimolecular (type I) and bimolecular (type II) initiators. In addition, they are distinguished by their chemical nature as photoinitiators for free-radical, anionic, cationic or mixed types of polymerization.

Type I photoinitiators (Norrish type I) for free-radical photopolymerization form free radicals on irradiation through unimolecular bond scission. Examples of type I photoinitiators are triazines, oximes, benzoin ethers, benzil ketals, bisimidazoles, aroylphosphine oxides, sulphonium salts and iodonium salts.

Type II photoinitiators (Norrish type II) for free-radical polymerization consist of a dye as sensitizer and a coinitiator, and undergo a bimolecular reaction on irradiation with light matched to the dye. First of all, the dye absorbs a photon and transfers energy from an excited state to the coinitiator. The latter releases the polymerization-triggering free radicals through electron or proton transfer or direct hydrogen abstraction.

In the context of this invention, preference is given to using type II photoinitiators.

Photoinitiator systems of this kind are described in principle in EP 0 223 587 A and consist preferably of a mixture of one or more dyes with ammonium alkylarylborate(s).

Suitable dyes which, together with an ammonium alkylarylborate, form a type II photoinitiator are the cationic dyes described in WO 2012062655, in combination with the anions likewise described therein. Cationic dyes are preferably understood to mean those from the following classes: acridine dyes, xanthene dyes, thioxanthene dyes, phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, externally cationic merocyanine dyes, externally cationic neutrocyanine dyes, zeromethine dyes—especially naphtholactam dyes, streptocyanine dyes. Dyes of this kind are described, for example, in H. Berneth in Ullmann's Encyclopedia of Industrial Chemistry, Azine Dyes, Wiley-VCH Verlag, 2008, H. Berneth in Ullmann's Encyclopedia of Industrial Chemistry, Methine Dyes and Pigments, Wiley-VCH Verlag, 2008, T. Gessner, U. Mayer in Ullmann's Encyclopedia of Industrial Chemistry, Triarylmethane and Diarylmethane Dyes, Wiley-VCH Verlag, 2000.

Particular preference is given to phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, zeromethine dyes—especially naphtholactam dyes, streptocyanine dyes.

Examples of cationic dyes are Astrazon Orange G, Basic Blue 3, Basic Orange 22, Basic Red 13, Basic Violet 7, Methylene Blue, New Methylene Blue, Azure A, 2,4-diphenyl-6-(4-methoxyphenyl)pyrylium, Safranin O, Astraphloxin, Brilliant Green, Crystal Violet, Ethyl Violet and thionine.

Preferred anions are especially $C_8$- to $C_{25}$-alkanesulphonate, preferably $C_{13}$- to $C_{25}$-alkanesulphonate, $C_3$- to $C_{18}$-perfluoroalkanesulphonate, $C_4$- to $C_{18}$-perfluoroalkanesulphonate bearing at least 3 hydrogen atoms in the alkyl chain, $C_9$- to $C_{25}$-alkanoate, $C_9$- to $C_{25}$-alkenoate, $C_8$- to $C_{25}$-alkylsulphate, preferably $C_{13}$- to $C_{25}$-alkylsulphate, $C_8$- to $C_{25}$-alkenylsulphate, preferably $C_{13}$- to $C_{25}$-alkenylsulphate, $C_3$- to $C_{18}$-perfluoroalkylsulphate, $C_4$- to $C_{18}$-perfluoroalkylsulphate bearing at least 3 hydrogen atoms in the alkyl chain, polyether sulphates based on at least 4 equivalents of ethylene oxide and/or 4 equivalents of propylene oxide, bis($C_4$- to $C_{25}$-alkyl, $C_5$- to $C_7$-cycloalkyl, $C_3$- to $C_8$-alkenyl or $C_7$- to $C_{11}$-aralkyl)sulphosuccinate, bis-$C_2$- to $C_{10}$-alkylsulphosuccinate substituted by at least 8 fluorine atoms, $C_8$- to $C_{25}$-alkylsulphoacetates, benzenesulphonate substituted by at least one radical from the group of halogen, $C_4$- to $C_{25}$-alkyl, perfluoro-$C_1$- to $C_8$-alkyl and/or $C_1$- to $C_{12}$-alkoxycarbonyl, naphthalene- or biphenylsulphonate optionally substituted by nitro, cyano, hydroxyl, $C_1$- to $C_{25}$-alkyl, $C_1$- to $C_{12}$-alkoxy, amino, $C_1$- to $C_{12}$-alkoxycarbonyl or chlorine, benzene-, naphthalene- or biphenyldisulphonate optionally substituted by nitro, cyano, hydroxyl, $C_1$- to $C_{25}$-alkyl, $C_1$- to $C_{12}$-alkoxy, $C_1$- to $C_{12}$-alkoxycarbonyl or chlorine, benzoate substituted by dinitro, $C_6$- to $C_{25}$-alkyl, $C_4$- to $C_{12}$-alkoxycarbonyl, benzoyl, chlorobenzoyl or tolyl, the anion of naphthalenedicarboxylic acid, diphenyl ether disulphonate, sulphonated or sulphated, optionally at least monounsaturated $C_8$ to $C_{25}$ fatty acid esters of aliphatic $C_1$ to $C_8$ alcohols or glycerol, bis(sulpho-$C_2$- to $C_6$-alkyl) $C_3$- to $C_{12}$-alkanedicarboxylates, bis(sulpho-$C_2$- to $C_6$-alkyl) itaconates, (sulpho-$C_2$- to $C_6$-alkyl) $C_6$- to $C_{18}$-alkanecarboxylates, (sulpho-$C_2$- to $C_6$-alkyl) acrylates or methacrylates, triscatechol phosphate optionally substituted by up to 12 halogen radicals, an anion from the group of tetraphenylborate, cyanotriphenylborate, tetraphenoxyborate, $C_4$- to $C_{12}$-alkyltriphenylborate, wherein the phenyl or phenoxy radicals may be substituted by halogen, $C_1$- to $C_4$-alkyl and/or $C_1$- to $C_4$-alkoxy, $C_4$- to $C_{12}$-alkyltrinaphthylborate, tetra-$C_1$- to $C_{20}$-alkoxyborate, 7,8- or 7,9-dicarba-nido-undecaborate(1-) or (2-), which are optionally substituted on the boron and/or carbon atoms by one or two $C_1$- to $C_{12}$-alkyl or phenyl groups, dodecahydrodicarbadodcaborate$^{(2-)}$ or B—$C_1$- to $C_{12}$-alkyl-C-phenyldodecahydrodicarbadodcaborate$^{(1-)}$, where, in the case of polyvalent anions such as naphthalenedisulphonate, A⁻ represents one equivalent of this anion, and where the alkane and alkyl groups may be branched and/or may be substituted by halogen, cyano, methoxy, ethoxy, methoxycarbonyl or ethoxycarbonyl.

It is also preferable when the anion A⁻ of the dye has an AC log P in the range from 1 to 30, more preferably in the range from 1 to 12 and especially preferably in the range from 1 to 6.5. The AC log P is calculated according to J. Comput. Aid. Mol. Des. 2005, 19, 453; Virtual Computational Chemistry Laboratory, http://www.vcclab.org.

Suitable ammonium alkylarylborates are the inventive ammonium alkyl aryl borates of formula (Ia) as well as their also inventive mixtures with borates of the formulae (Ib) and/or (IIIa) and/or (IIIb) and/or the salts of formula (II).

It may be advantageous to use mixtures of these photoinitiators. According to the radiation source used, the type and concentration of photoinitiator has to be adjusted in the manner known to those skilled in the art. Further details are described, for example, in P. K. T. Oldring (Ed.), Chemistry & Technology of UV & EB Formulations For Coatings, Inks & Paints, vol. 3, 1991, SITA Technology, London, p. 61-328.

It is most preferable when the photoinitiator comprises a combination of dyes whose absorption spectra at least partly cover the spectral range from 400 to 800 nm, with at least one coinitiator matched to the dyes.

It is also preferable when at least one photoinitiator suitable for a laser light colour selected from blue, green and red is present in the photopolymer formulation.

It is also further preferable when the photopolymer formulation contains one suitable photoinitiator each for at least two laser light colours selected from blue, green and red.

Finally, it is most preferred when the photopolymer formulation contains one suitable photoinitiator for each of the laser colours blue, green and red.

The photopolymer formulation can be used to produce photopolymer films preferably having a layer thickness of $\geq 1$ µm and $\leq 100$ µm, more preferably of $\geq 5$ µm and $\leq 30$ µm and most preferably of $\geq 7$ µm and $\leq 25$ µm.

Holographic Media

Using the inventive coinitiators containing at least one substance of the formula (Ia) or mixtures thereof with substances of the formulae (Ib), (IIIa) and/or (IIIb) and optionally salts of the formula (II), it was possible to produce photopolymer films which exhibit high long-term stability and photochemical bleachability, and into which light-coloured holograms can be exposed.

The invention further provides holographic media which can be produced using the inventive photopolymer formulation.

The holographic media may contain or consist of the abovementioned photopolymer films based on the inventive photopolymer formulation.

The holographic media may be in exposed or unexposed form.

The inventive holographic media can can be processed to holograms by means of appropriate exposure processes for optical applications over the entire visible range (400-800 nm). Visual holograms include all holograms which can be recorded by methods known to those skilled in the art. These include in-line (Gabor) holograms, off-axis holograms, full-aperture transfer holograms, white light transmission holograms ("rainbow holograms"), Denisyuk holograms, off-axis reflection holograms, edge-lit holograms and holographic stereograms. Preference is given to reflection holograms, Denisyuk holograms, transmission holograms.

Possible optical functions of the holograms which can be produced with the inventive photopolymer formulations correspond to the optical functions of light elements such as lenses, mirrors, deflecting mirrors, filters, diffuser lenses, diffraction elements, light guides, waveguides, projection lenses and/or masks. These optical elements frequently have a frequency selectivity according to how the holograms have been exposed and the dimensions of the hologram.

In addition, by means of the inventive photopolymer formulations, it is also possible to produce holographic images or representations, for example for personal portraits, biometric representations in security documents, or generally of images or image structures for advertising, security labels, brand protection, branding, labels, design elements, decorations, illustrations, collectable cards, images and the like, and also images which can represent digital data, including in combination with the products detailed above. Holographic images can have the impression of a three-dimensional image, but they may also represent image sequences, short films or a number of different objects according to the angle from which and the light source with which (including moving light sources) etc. they are illuminated. Because of this variety of possible designs, holograms, especially volume holograms, constitute an attractive technical solution for the abovementioned application.

The photopolymer formulations can especially be used for production of holographic media in the form of a film. In this case, a ply of a material or material composite transparent to light within the visible spectral range (transmission greater than 85% within the wavelength range from 400 to 780 nm) as carrier is coated on one or both sides, and a cover layer is optionally applied to the photopolymer ply or plies.

The invention therefore also provides a process for producing a holographic medium, in which
(I) an inventive photopolymer formulation is produced by mixing all the constituents,
(II) the photopolymer formulation is converted to the form desired for the holographic medium at a processing temperature and (III) cured in the desired form with urethane formation at a crosslinking temperature above the processing temperature.

Preferably, the photopolymer formulation is produced in step I) by mixing the individual constituents. For this purpose, the writing monomers, the additives and the catalyst are preferably added to and mixed with the component reactive toward isocyanates in a stepwise manner. Subsequently, a solution of the light-sensitive photoinitiator solution is preferably added to the mixture in the dark and mixed, so as to obtain a clear solution. If necessary, the formulation is heated at 60° C. for a short period in order to bring the starting materials into solution more quickly. This mixture can be introduced into one of two reservoir vessels of a film coating system known to the expert. The polyisocyanate component can be introduced into the second reservoir vessel. The two components are then preferably mixed. In this context, it is possible to use systems including the metering, filtering and devolatilization systems known to those skilled in the art. The liquid composition obtained can then be fed to a coating device.

Preferably, the photopolymer formulation is converted in step II) to the form of a film. For this purpose, the photopolymer formulation can be applied, for example, over the area of a carrier substrate, in which case, for example, the apparatuses known to those skilled in the art (doctor blade, knife-over-roll, comma bar, inter alia) or a slot die can be used. The processing temperature here is in the range of 20 to 40° C., preferably in the range of 20 to 30° C.

The carrier substrate used may be a ply of a material or material composite transparent to light in the visible spectral range (transmission greater than 85% in the wavelength range from 400 to 800 nm).

Preferred materials or material composites for the carrier substrate are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyamide, polymethylmethacrylate, polyvinyl chloride, polyvinyl butyral or polydicyclopentadiene or mixtures thereof. They are more preferably based on PC, PET and CTA. Material composites may be film laminates or coextrudates. Preferred material composites are duplex and triplex films formed according to one of the schemes A/B, A/B/A or A/B/C. Particular preference is given to PC/PET, PET/PC/PET and PC/TPU (TPU=thermoplastic polyurethane).

As an alternative to the aforementioned carrier substrates, it is also possible to use planar glass panes, which find use especially for large-area, high-accuracy exposures, for example for holographic lithography (Holographic interference lithography for integrated optics, IEEE Transactions on Electron Devices (1978), ED-25(10), 1193-1200, ISSN: 0018-9383).

The materials or material composites of the carrier substrate may be given an antiadhesive, antistatic, hydrophobized or hydrophilized finish on one or both sides. The modifications mentioned serve the purpose, on the side facing the photopolymer, of making the photopolymer detachable without destruction from the carrier substrate. Modification of the opposite side of the carrier substrate from the photopolymer serves to ensure that the inventive media satisfy specific mechanical demands which exist, for example, in the case of processing in roll laminators, especially in roll-to-roll processes.

The carrier substrate may be coated on one or both sides.

The crosslinking temperature may especially be ≥60° C. and ≤110° C. and preferably ≥70° C. and ≤105° C. and more preferably ≥75° C. and ≤100° C.

The invention also provides a holographic medium obtainable by the process according to the invention.

The invention further provides a laminate structure comprising a carrier substrate, an inventive holographic medium applied thereto, and optionally a cover layer applied to the opposite side of the holographic medium from the carrier substrate.

The laminate structure may especially have one or more cover layers on the holographic medium in order to protect it from soil and environmental influences. For this purpose, it is possible to use polymer films or film composite systems, or else clearcoats.

The cover layers used are preferably film materials analogous to the materials used in the carrier substrate, and these may have a thickness of typically 5 to 200 µm, preferably 8 to 125 µm, more preferably 10 to 50 µm.

Preference is given to cover layers having a very smooth surface. A measure used here is the roughness, determined to DIN EN ISO 4288 "Geometrical Product Specifications (GPS)—Surface texture . . . ", test condition: R3z front and reverse sides. Preferred roughnesses are in the region of less than or equal to 2 µm, preferably less than or equal to 0.5 µm.

The cover layers used are preferably PE or PET films of thickness 20 to 60 µm. More preferably, a polyethylene film having a thickness of 40 µm is used.

It is likewise possible that, in the case of a laminate structure on the carrier substrate, a further cover layer is applied as a protective layer.

Synthesis Processes

The invention further provides a process for preparing coinitiators comprising a mixture of substances of the formula (Ia) and salts of the formula (II), and optionally also containing substances of the formula (Ib) and/or of the formula (IIIa) and/or of the formula (IIIb)

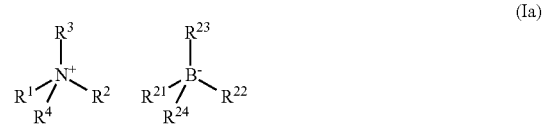
(Ia)

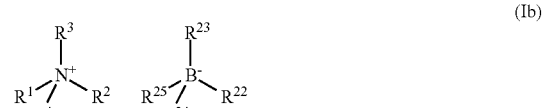
(Ib)

(II)

(IIIa)

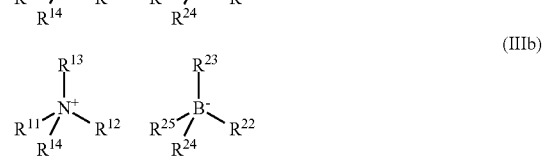
(IIIb)

in which
$R^1$ to $R^4$, $R^{11}$ to $R^{14}$, $R^{21}$ to $R^{24}$, $R^{25}$ and $An^-$ are each as defined above,
characterized in that borates of the formula (IIIa) or a mixture of borates of the formulae (IIIa) and (IIIb) are reacted with an ammonium salt of the formula (VI)

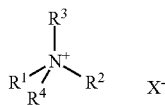  (VI)

in which
$R^1$ to $R^4$ are each as defined above and $X^-$ is an anion, preferably a halide ion,
in the presence of a salt of the formula (VII)

  (VII)

in which
$M^+$ is a cation, preferably an alkali metal ion or an ammonium ion, and
$An^-$ is as defined above,
in a biphasic mixture of water and an ester.
$M^+$ is preferably $Na^+$ or $K^+$, more preferably $Na^+$.

An efficient process for preparing the carbon-substituted ammonium alkyltriarylborates suitable as coinitiators has surprisingly been achieved by synthesizing them in the presence of an anion $An^-$.

It has been found that, surprisingly, particularly suitable anions are the anions $An^-$ which have already been defined above and have an AC log P in the range from 2 to 8, preferably 3 to 6, more preferably 3.5 to 5.

Preferably, the process is conducted in such a way that the biphasic mixture is separated, the organic phase is washed with water to remove anions $X^-$ and, finally, the organic phase is freed of water present.

The number of water washes is determined by the anion $X^-$ introduced with the ammonium salt of the formula (VI) no longer being detectable in the last water wash. If, as is preferred, $X^-$ is chloride or bromide, this detection is conducted, for example, in such a way that a sample from the water wash is acidified with 10 percent by weight nitric acid and then a 5 percent by weight aqueous solution of silver nitrate is added. If no more than barely visible turbidity then arises, it is possible to dispense with further water washes.

It will be appreciated that the number of water washes required also depends on the volume thereof relative to the volume of the organic phase. 3 to 10, preferably 4 to 8, water washes are a good guide value.

Likewise preferably, the procedure is such that the salts of the formula (VII) are used, relative to the substances of the formula (Ia) or the sum total of the substances of the formulae (Ia) and (Ib), in a molar ratio of 0.5 to 10:100, preferably 1 to 5:100.

Additionally preferably, the salts of the formula (II) are used, relative to the sum total of the substances of the formulae (Ia), (Ib) and the salt of the formula (VII), in a molar ratio of 100 to 110:100, preferably 100 to 105:100, more preferably 100 to 102:100.

Suitable esters are the optionally substituted alkyl esters of formic acid, acetic acid, propionic acid or butanoic acid. The alkyl groups may contain 1 to 6 carbon atoms and optionally be branched. They may also bear radicals such as alkoxy.

Examples are n- or i-propyl formate, n-, s- or i-butyl formate, methyl acetate, ethyl acetate, n- or i-propyl acetate, n-, s- or i-butyl acetate, methoxypropyl acetate, diethylene glycol monoethyl ether acetate, ethyl propionate, methyl butyrate, ethyl butyrate. Preference is given to ethyl acetate, n-butyl acetate and methoxypropyl acetate, particular preference to n-butyl acetate.

The process can be conducted at a temperature of $\geq 10$ and $\leq 100°$ C., preferably $\geq 20$ and $\leq 70°$ C., more preferably $\geq 25$ and $\leq 50°$ C.

In the process according to the invention, it is possible to prepare stable solutions of the coinitiators of the formula (Ia) and mixtures thereof with tetraarylborates of the formula (Ib) and/or tetraalkylammonium borates of the formulae (IIIa) and (IIIb) and with salts of the formula (II). The solutions are preferably based on the above-specified solvents, more preferably ethyl acetate, n-butyl acetate and methoxypropyl acetate, most preferably n-butyl acetate. The concentration thereof can vary within wide limits. For example, it is $\geq 1$ and $\leq 90\%$ by weight, preferably $\geq 10$ and $\leq 70\%$ by weight, more preferably $\geq 30$ and $\leq 60\%$ by weight, based on the total mass of the solution. The solutions are preferably stable down to $-78°$ C. Below this temperature, they solidify without separation to give a clear, very tough glass.

The invention therefore also further provides coinitiators preparable by the process according to the invention. These are particularly suitable for use in the abovementioned photopolymer formulations. In addition, the photopolymer formulations obtained are then suitable for production of holographic media with the good properties already detailed above. In this case, the coinitiators, in a preferred embodiment, are in the form of solutions in the abovementioned solvents.

The invention further provides borates of the formula (VIII)

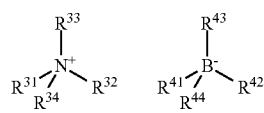  (VIII)

in which
$R^{31}$ is an optionally branched $C_{14}$- to $C_{22}$-alkyl radical,
$R^{32}$ is a $C_7$- to $C_{10}$-aralkyl radical,
$R^{33}$ and $R^{34}$ are each independently an optionally branched and/or optionally substituted $C_1$- to $C_5$-alkyl radical,
$R^{41}$ is a $C_2$- to $C_{22}$-alkyl, $C_3$- to $C_{22}$-alkenyl, $C_5$- to $C_7$-cycloalkyl or $C_7$ to $C_{13}$-aralkyl radical and
$R^{42}$ to $R^{44}$ are each independently a $C_6$- to $C_{10}$-aryl radical substituted by at least one radical selected from halogen, $C_1$- to $C_4$-alkyl, trifluoromethyl, $C_1$- to $C_4$-alkoxy, trifluoromethoxy, phenyl and phenoxy,
excluding the combination of $R^{31}$=tetradecyl, $R^{32}$=benzyl, $R^{33}$ and $R^{34}$=methyl, $R^{41}$=butyl and $R^{42}$ to $R^{44}$=phenyl,
or in which
$R^{31}$ is an optionally branched $C_{14}$- to $C_{22}$-alkyl radical,
$R^{32}$ is a $C_7$- to $C_{10}$-aralkyl radical,
$R^{33}$ and $R^{34}$ are each independently an optionally branched and/or optionally substituted $C_1$- to $C_5$-alkyl radical,
$R^{41}$ is a $C_2$- to $C_{22}$-alkyl, $C_3$- to $C_{22}$-alkenyl, $C_5$- to $C_7$-cycloalkyl or $C_7$ to $C_{13}$-aralkyl radical and
$R^{42}$ to $R^{44}$ are each independently a $C_6$- to $C_{10}$-aryl radical substituted by at least one radical selected from halogen, $C_1$- to $C_4$-alkyl, trifluoromethyl, $C_1$- to $C_4$-alkoxy, trifluoromethoxy, phenyl and phenoxy,
or in which
$R^{31}$ is an optionally branched $C_{14}$- to $C_{22}$-alkyl radical,
$R^{32}$ is an optionally branched $C_8$ to $C_{22}$-alkyl radical or a $C_7$ to $C_{10}$-aralkyl radical,
$R^{33}$ and $R^{34}$ together form a —$(CH_2)_4$—, —$(CH_2)_5$— or —$(CH_2)_2$—O—$(CH_2)_2$— bridge,
$R^{41}$ is a $C_2$- to $C_{22}$-alkyl, $C_3$- to $C_{22}$-alkenyl, $C_5$- to $C_7$-cycloalkyl or $C_7$ to $C_{13}$-aralkyl radical and
$R^{42}$ to $R^{44}$ are each independently a $C_6$- to $C_{10}$-aryl radical substituted by at least one radical selected from halogen, $C_1$- to $C_4$-alkyl, trifluoromethyl, $C_1$- to $C_4$-alkoxy, trifluoromethoxy, phenyl and phenoxy,
or in which
$R^{31}$ is an optionally branched $C_{14}$- to $C_{22}$-alkyl radical,
$R^{32}$ is a phenyl radical substituted by one to three radicals from the group of optionally branched $C_3$- to $C_8$-alkyl radical, optionally branched $C_3$- to $C_8$-alkoxy radical, trifluoromethyl, trifluoromethoxy, cyclopentyl, cyclohexyl, cycloheptyl, phenyl and phenoxy,
$R^{33}$ and $R^{34}$ are each independently an optionally branched and/or optionally substituted $C_1$- to $C_5$-alkyl radical,
$R^{41}$ is a $C_2$- to $C_{22}$-alkyl, $C_3$- to $C_{22}$-alkenyl, $C_5$- to $C_7$-cycloalkyl or $C_7$ to $C_{13}$-aralkyl radical and
$R^{42}$ to $R^{44}$ are each independently a $C_6$- to $C_{10}$-aryl radical substituted by at least one radical selected from halogen, $C_1$- to $C_4$-alkyl, trifluoromethyl, $C_1$- to $C_4$-alkoxy, trifluoromethoxy, phenyl and phenoxy,
or in which
$R^{31}$ is an optionally branched $C_{14}$- to $C_{22}$-alkyl radical and $R^{32}$, $R^{33}$ and $R^{34}$ together with the $N^+$ atom form an imidazole or pyridine ring substituted at least by one radical selected from $C_1$- to $C_8$-alkyl, $C_1$- to $C_8$-alkoxy, $C_5$- to $C_7$-cycloalkyl, benzyl or phenyl,
$R^{41}$ is a $C_2$- to $C_{22}$-alkyl, $C_3$- to $C_{22}$-alkenyl, $C_5$- to $C_7$-cycloalkyl or $C_7$ to $C_{13}$-aralkyl radical and
$R^{42}$ to $R^{44}$ are each independently a $C_6$- to $C_{10}$-aryl radical substituted by at least one radical selected from halogen, $C_1$- to $C_4$-alkyl, trifluoromethyl, $C_1$- to $C_4$-alkoxy, trifluoromethoxy, phenyl and phenoxy.

Preferred borates of the above-detailed formula (VII) are those in which
$R^{31}$ is tetradecyl, hexadecyl, octadecyl, eicosyl or docosyl, more preferably hexadecyl or octadecyl,
$R^{32}$ is benzyl, 2-phenylethyl, 2- or 3-phenylethyl, more preferably benzyl or 3-phenylpropyl, and
$R^{33}$ and $R^{34}$ are the same and are each methyl, ethyl or hydroxyethyl, more preferably methyl,
or in which
$R^{31}$ is tetradecyl, hexadecyl, octadecyl, eicosyl or docosyl, more preferably hexadecyl or octadecyl,
$R^{32}$ is a phenyl radical substituted by at least one radical in the 3, 4 and/or 5 position, from the group of 1- or 2-butyl, 1,1-dimethylethyl, 1-hexyl, 1-octyl, 1- or 2-butoxy, 1,1-dimethylethoxy, trifluoromethyl, trifluoromethoxy, cyclopentyl, cyclohexyl, cycloheptyl, phenyl and phenoxy, and
$R^{33}$ and $R^{34}$ are the same and are each methyl, ethyl or hydroxyethyl, more preferably methyl,
or in which
$R^{31}$ is tetradecyl, hexadecyl, octadecyl, eicosyl or docosyl, more preferably hexadecyl or octadecyl,
$R^{32}$ is octyl, 2-ethylhexyl, nonyl, decyl, dodecyl, tetradecyl, hexadecyl, octadecyl, eicosyl, docosyl, benzyl, 2-phenylethyl, 2- or 3-phenylethyl, more preferably dodecyl, tetradecyl, hexadecyl, octadecyl, benzyl or 3-phenylpropyl, and
$R^{33}$ and $R^{34}$ together form a —$(CH_2)_4$—, —$(CH_2)_5$— or —$(CH_2)_2$—O—$(CH_2)_2$— bridge.

Preferred borates of the above-detailed formula (VIII) are those in which
$R^{41}$ is an optionally branched and optionally fluorine-, chlorine-, methoxy-, ethoxy- or cyano-substituted $C_2$- to $C_{18}$-alkyl, $C_3$- to $C_{12}$-alkenyl or $C_7$- to $C_{10}$-aralkyl radical, cyclopentyl or cyclohexyl and
$R^{42}$ to $R^{44}$ are each independently a $C_6$- to $C_{10}$-aryl radical optionally substituted by at least one radical selected from fluorine, chlorine, $C_1$- to $C_4$-alkyl, trifluoromethyl, $C_1$- to $C_4$-alkoxy, trifluoromethoxy, phenyl and phenoxy.

Particular preference is given to those where
$R^{41}$ is 1- or 2-butyl, 1,1-dimethylethyl, 1- or 2-pentyl, 1- or 2-hexyl, 1- or 2-heptyl, 1- or 2-octyl, 2-ethylhexyl, 1- or 2-nonyl, 1- or 2-decyl, 1-dodecyl, 1-tetradecyl, 1-hexadecyl, 1-octadecyl, allyl, 2-buten-1-yl, benzyl, 2-phenylethyl, 2- or 3-phenylpropyl, cyclopentyl or cyclohexyl and
$R^{42}$ to $R^{44}$ are each independently a phenyl radical optionally substituted in the 3 and/or 4 position by at least one radical selected from fluorine, chlorine, methyl, trifluoromethyl, methoxy and trifluoromethoxy.

Very particular preference is given to those where
$R^{41}$ is 1-butyl, 1-pentyl, 1-hexyl, 1-heptyl, 1-octyl, 1-nonyl, 1-decyl, 1-dodecyl, 1-tetradecyl, 1-hexadecyl, 1-octadecyl, allyl, 3-phenylpropyl, cyclopentyl or cyclohexyl and
$R^{42}$ to $R^{44}$ are each 4-fluorophenyl, 4-chlorophenyl, 3-fluoro-4-methylphenyl or 3-chloro-4-methylphenyl and
$R^{42}$ to $R^{44}$ are the same.

Preference is additionally given to those where
$R^{41}$ is 1-butyl, 1-hexyl, 1-octyl, 1-dodecyl or 3-phenylpropyl,
$R^{42}$ to $R^{44}$ are each 4-fluorophenyl, 4-chlorophenyl, 3-fluoro-4-methylphenyl or 3-chloro-4-methylphenyl and
$R^{42}$ to $R^{44}$ are the same.

In a specific embodiment of the inventive borates, the abovementioned $R^{32}$, $R^{33}$ and $R^{34}$ radicals together with the $N^+$ form an imidazole or pyridine ring corresponding to one of the formulae

(IX)

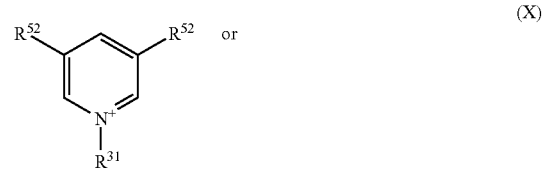

(X)

(XI)

in which $R^{31}$ is an optionally branched $C_{14}$- to $C_{22}$-alkyl radical and $R^{51}$ and $R^{53}$ are each independently an optionally branched $C_3$- to $C_8$-alkyl radical, cyclopentyl, cyclohexyl, cycloheptyl or phenyl, and $R^{51}$ is additionally an optionally branched $C_3$- to $C_8$-alkoxy radical or phenoxy, and $R^{53}$ is additionally phenyl or benzyl, $R^{52}$ is a $C_1$- to $C_4$-alkyl radical and $R^{54}$ is hydrogen, a $C_1$- to $C_4$-alkyl radical or phenyl.

More preferably, $R^{31}$ is tetradecyl, hexadecyl, octadecyl, eicosyl or docosyl, more preferably hexadecyl or octadecyl, $R^{51}$ and $R^{53}$ are each independently 1- or 2-propyl, 1- or 2-butyl, 1,1-dimethylethyl, 1-hexyl, 1-octyl, 2-ethylhexyl, cyclopentyl, cyclohexyl, cycloheptyl or phenyl, more preferably 1- or 2-butyl, 1,1-dimethylethyl, cyclohexyl or phenyl, and $R^{31}$ is additionally 1- or 2-propoxy, 1- or 2-butoxy, 1,1-dimethylethoxy, 1-hexoxy, 1-octoxy, 2-ethylhexoxy or phenoxy, more preferably 1- or 2-butoxy, 1,1-dimethylethoxy or phenoxy, and $R^{53}$ is additionally phenyl or benzyl, more preferably benzyl, $R^{52}$ is methyl, ethyl, 1- or 2-propyl, 1- or 2-butyl or 1,1-dimethylethyl, more preferably 1- or 2-butyl or 1,1-dimethylethyl, and $R^{54}$ is hydrogen, methyl, ethyl or phenyl, more preferably hydrogen or methyl.

EXAMPLES

Starting Substances:
sodium bis(2-ethylhexyl)sulphosuccinate (AC log P=3.67)
sodium sec-dodecylbenzenesulphonate (AC log P=4.85)
Methods:
Measurement of Glass Transition Temperature $T_g$ by Means of DSC The measurements were based on DIN EN 61006, Method A. The calibration of the DSC instrument was effected with the aid of indium and lead as reference.

10 mg of sample are weighed with the aid of a microbalance (MT5 from Mettler-Toledo) in a closed but perforated aluminium crucible having a volume of 40 μl. In a differential heat flux colorimeter (DSC 822 from Mettler-Toledo), the heat flux of the sample is measured relative to a reference at a constant heating rate of 20 K/min. The receptacle of the DSC 822 that contains the sample and the reference is purged with a nitrogen stream of flow rate 20 ml/min during the measurement.

The following programmed temperature cycle is run through:

First cooling. The start temperature is 30° C., the end temperature −100° C. The cooling rate is set to 50 K/min. On attainment of the end temperature, the temperature is kept constant for another 7 min.

First heating. The start temperature is −100° C., the end temperature 80° C. The heating rate is set to 20 K/min. In the course of this, the heat flux is recorded constantly.

Second cooling. The start temperature is 80° C., the end temperature −100° C. The cooling rate is set to 50 K/min. On attainment of the end temperature, the temperature is kept constant for another 7 min.

Second heating. The start temperature is −100° C., the end temperature 150° C. The heating rate is set to 20 K/min. In the course of this, the heat flux is recorded constantly.

Third cooling. The start temperature is 150° C., the end temperature −100° C. The cooling rate is set to 50 K/min. On attainment of the end temperature, the temperature is kept constant for another 7 min.

Third heating. The start temperature is −100° C., the end temperature 150° C. The heating rate is set to 20 K/min. In the course of this, the heat flux is recorded constantly.

The glass transition is identified as a step increase in the heat flux curve in the course of heating. The glass transition temperature is then that temperature at which half the step height has been attained in the heat flux curve at the glass transition.

In order to eliminate the thermal history of the samples, only glass transition temperatures of the third heating are reported.

Determination of the Cation Ratio by Means of $^1$H NMR:

$^1$H NMR were measured on a Bruker DPX-400, 400 MHz and recorded in $CDCl_3$. The evaluation was effected by the integrals of characteristic signals of the individual constituents; see the details in the examples.

Determination of the Proportion of Borates in the Solution by Means of HPLC:

The HPLC measurements were conducted under reversed phase conditions, using an octadecylsilyl-modified silica gel column (end-capped). The mobile phase used was a mixture of acetonitrile and water (buffered, contains an amine). The elution was effected with an eluent gradient altered stepwise. The substances were detected by UV detection at 205 nm, and the quantification was effected with the aid of an external standard.

Examples 1 to 4: Preparation Method

Example 1

500 g of a mixture of 99.7% by weight of tetrabutylammonium hexyltris(3-chloro-4-methylphenyl)borate and 0.3% by weight of tetrabutylammonium tetrakis(3-chloro-4-methylphenyl)borate (m.p.=119-121° C., no $T_g$), 304 g of benzyldimethylhexadecylammonium chloride hydrate (1.05 molar equivalents) and 15.5 g of sodium bis(2-ethylhexyl) sulphosuccinate (0.05 molar equivalent) were stirred in a mixture of 1500 ml of butyl acetate and 1750 ml of water in a 6 l flange apparatus at 25° C. for 2.5 h. This temperature was maintained in all subsequent steps. The stirrer was switched off. After 30 min, the lower aqueous phase was discharged through the base valve. The organic phase was stirred with 800 ml of water for 30 min. The stirrer was switched off. After 30 min, the lower aqueous phase was discharged through the base valve. The organic phase was stirred with 800 ml of water for 30 min. This procedure was repeated twice. In the last water phase, it was still possible to detect a high level of chloride ions (3 ml sample+0.5 ml of 10 percent $HNO_3$+0.5 ml of 5 percent $AgNO_3$ solution). Four more times, the organic phase was stirred with 800 ml of water for 30 min and, finally, after no stirring for 30 minutes, the water phase was discharged. In the last water phase, no chloride ions were detectable any longer. The organic phase was freed of the dissolved and entrained water by azeotropic means on a rotary evaporator at bath temperature 60° C. and a final vacuum of 60 mbar. This gave 937.8 g of a clear solution which, by HPLC, had a 53.9% by weight content of the mixture of the borates of the formulae

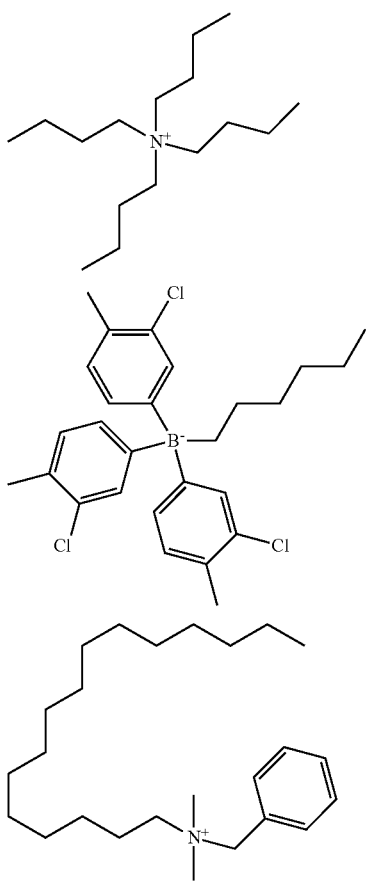

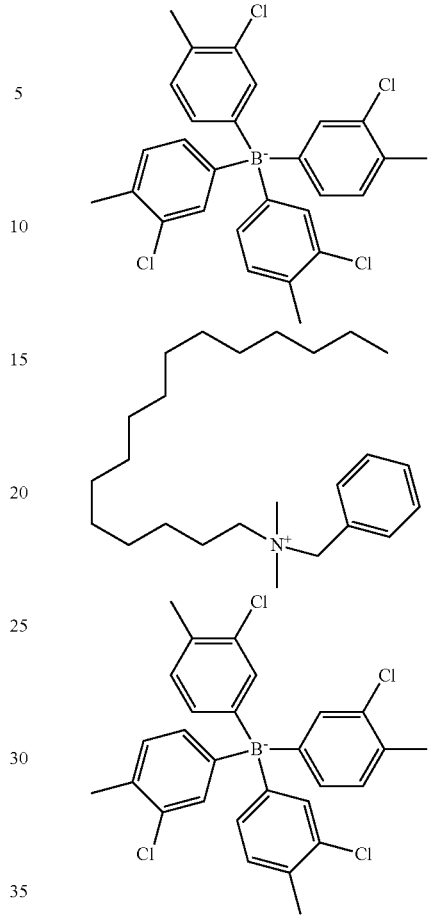

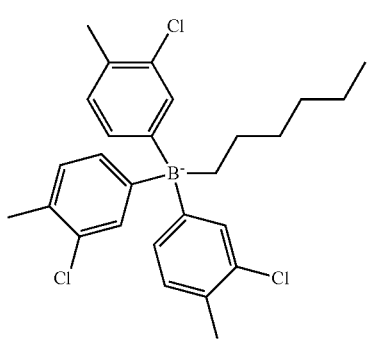

and a 0.1% by weight content of the mixture of the borates of the formulae

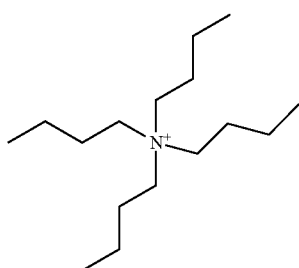

The yield was thus 94.2% of theory. By means of $^1$H NMR (in CDCl$_3$, characteristic signals for tetrabutylammonium: δ=2.55 ppm (m, 8H), for benzyldimethylhexadecylammonium: δ=6.95 ppm (d, 2H), δ=3.40 ppm (s, 2H)), the molar ratio of the tetrabutylammonium to benzyldimethylhexadecylammonium cations was determined to be 1.7:98.3. Likewise by means of $^1$H NMR (in CDCl$_3$, characteristic signal for bis(2-ethylhexyl)sulphosuccinate: δ=3.25-3.1 ppm (m, 2H)), a content of 1.63% by weight of the sulphosuccinate of the formula

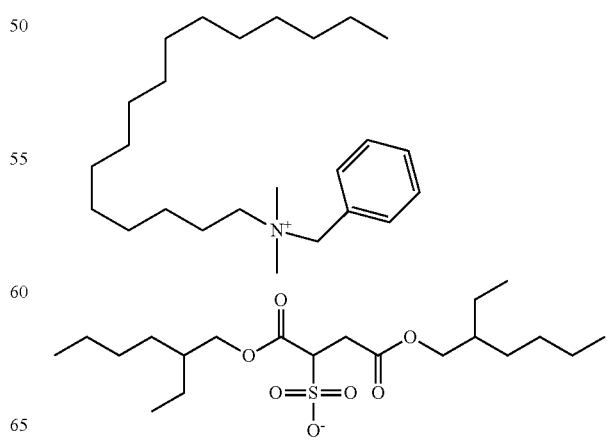

in the solution was found, i.e. 3.02% by weight based on the mixture of the borates.

Total washes: 8

Intermediate phases: 0

After evaporative concentration of a portion of the solution under reduced pressure and drying of the residue at 80° C. under reduced pressure, a colourless honey-like oil having a $T_g$ of −27° C. was obtained.

The above 54% by weight solution in butyl acetate is of unlimited stability at −5° C. and even at −78° C.

For comparison, a 30% by weight solution of the tetrabutylammonium hexyltris(3-chloro-4-methylphenyl)borate in butyl acetate used as reactant crystallizes out significantly at −5° C. after only 3 days. After 4 weeks at −5° C., about 75% by weight of this ammonium borate has crystallized out, i.e. the remaining solution has a content of only 7.5% by weight.

Example 2

The experiment in Example 1 was repeated, except that it was conducted at 45-50° C.

Here too, the reactant, analogously to Example 1, contained a corresponding preparation-related proportion of the analogous tetraarylborate. For the sake of clarity, these and also the products formed therefrom are not specified in detail.

This gave 950.7 g of a clear solution which, by HPLC, had a 54.6% by weight content of the mixture of the borates of the formulae

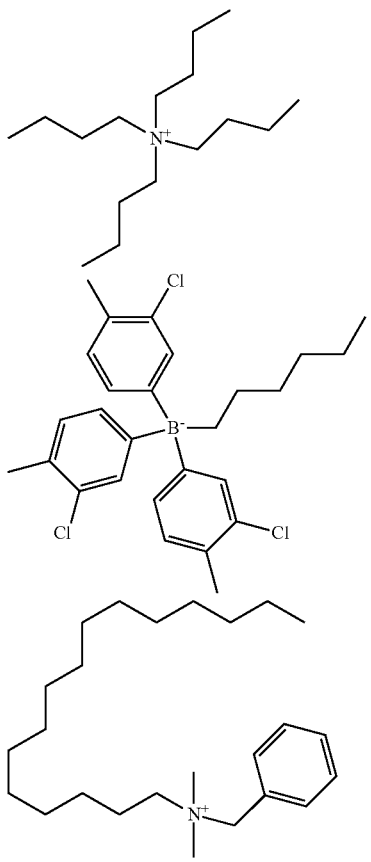

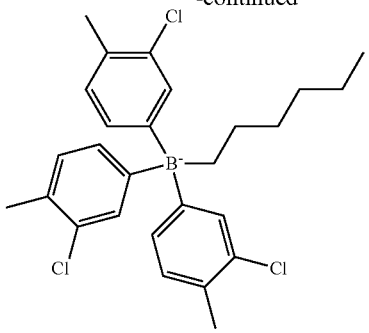

The yield was thus 96.6% of theory. By means of $^1$H NMR (in CDCl$_3$, for signals see Example 1), the molar ratio of the tetrabutylammonium to benzyldimethylhexadecylammonium cations was determined to be 1.7:98.3. Likewise by means of $^1$H NMR (in CDCl$_3$, for signals see Example 1), a content of 1.63% by weight of the sulphosuccinate of the formula

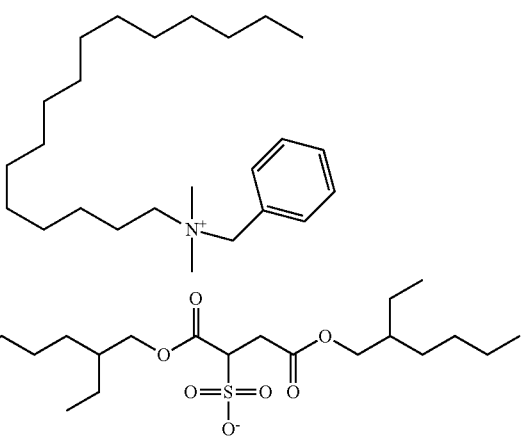

in the solution was found, i.e. 2.98% by weight based on the mixture of the borates.

Total washes: 8

Intermediate phases: 0

Example 3

25 g of tetrabutylammonium hexyltris(3-chloro-4-methylphenyl)borate, 14.8 g of benzyldimethylhexadecylammonium chloride hydrate (1.05 molar equivalents) and 0.79 g of sodium sec-dodecylbenzenesulphonate (0.05 molar equivalent, isomer mixture) were stirred in a mixture of 75 ml of butyl acetate and 85 ml of water at 25° C. for 2.5 h. Here too, the reactant, analogously to Example 1, contained a corresponding preparation-related proportion of the analogous tetraarylborate. For the sake of clarity, these and also the products formed therefrom are not specified in detail. The temperature was maintained in all subsequent steps. The mixture was transferred into a separating funnel and the lower aqueous phase was discharged after 30 min. The organic phase was stirred with 40 ml of water for 30 min and separated again from the aqueous phase in a separating funnel after 30 min. This procedure was repeated twice. In the last water phase, it was still possible to detect a high level of chloride ions (3 ml sample+0.5 ml of 10 percent HNO$_3$+

0.5 ml of 5 percent AgNO₃ solution). Four more times, the organic phase was stirred with 40 ml of water for 30 min and, finally, the water phase was separated off in a separating funnel. In the last water phase, no chloride ions were detectable any longer. The organic phase was freed of dissolved and entrained water by azeotropic means on a rotary evaporator at bath temperature 60° C. and a final vacuum of 60 mbar. This gave 47.6 g of a clear solution which, by ¹H NMR (in CDCl₃, characteristic signals for butyl acetate: δ=4.05 ppm (t, 2H), for hexyltris(3-chloro-4-methylphenyl)borate: δ=6.85 ppm (dd, 3H), δ=2.20 ppm (s, 9H), for benzyldimethylhexadecylammonium: δ=6.95 ppm (d, 2H), δ=3.40 ppm (s, 2H)), had a 54.1% by weight content of the mixture of the borates of the formulae

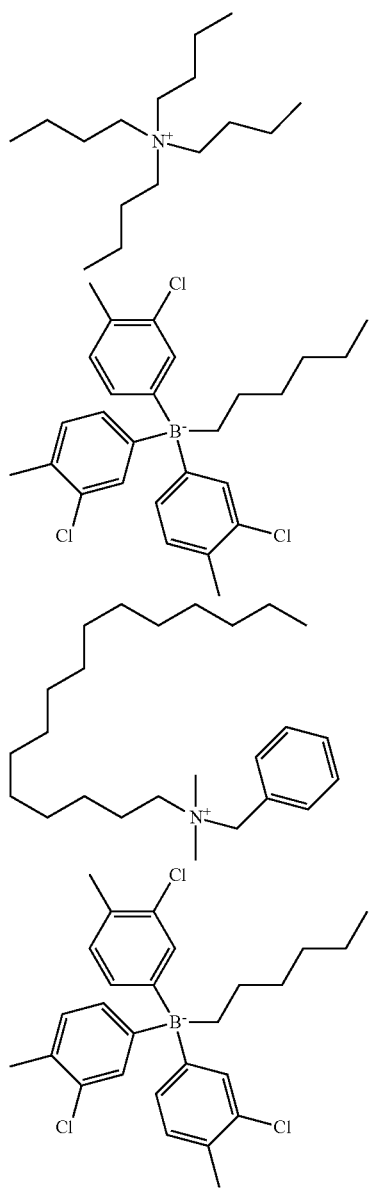

The yield was thus 96.0% of theory. By means of ¹H NMR (in CDCl₃, for signals see Example 1), the molar ratio of the tetrabutylammonium to benzyldimethylhexadecylammonium cations was determined to be 1.1:98.9. Likewise by means of ¹H NMR (in CDCl₃, characteristic signal for dodecylbenzenesulphonate: δ=7.77 ppm (dd, 2H)), a content of 2.08% by weight of the sec-dodecylbenzenesulphonate of the formula

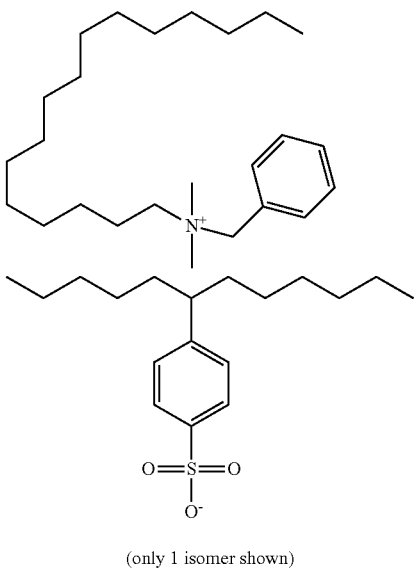

(only 1 isomer shown)

in the solution was found, i.e. 3.84% by weight based on the mixture of the borates.

Total washes: 7

Intermediate phases: 0

After evaporative concentration of a portion of the solution under reduced pressure and drying of the residue at 80° C. under reduced pressure, a colourless honey-like oil having a $T_g$ of −26° C. was obtained.

Example 4

5.00 g of a mixture of 99% by weight of tetrabutylammonium hexyltris(3-chloro-4-methylphenyl)borate and 1% by weight of tetrabutylammonium tetrakis(3-chloro-4-methylphenyl)borate, 3.04 g of benzyldimethylhexadecylammonium chloride hydrate (1.05 molar equivalents) and 0.155 g of sodium bis(2-ethylhexyl)sulphosuccinate (0.05 molar equivalent) were stirred in a mixture of 15 ml of butyl acetate and 20 ml of water at 25° C. for 2.5 h. Here too, the reactant, analogously to Example 1, contained a corresponding preparation-related proportion of the analogous tetraarylborate. For the sake of clarity, these and also the products formed therefrom are not specified in detail. The temperature was maintained in all subsequent steps. The mixture was transferred into a separating funnel and the lower aqueous phase was discharged after 10 min. The organic phase was shaken vigorously with 10 ml of water and separated again from the aqueous phase after 10 min. This procedure was repeated seven times. In the last water phase, it was no longer possible to detect any chloride ions (3 ml sample+0.5 ml of 10 percent HNO₃+0.5 ml of 5 percent AgNO₃ solution). The organic phase was freed of the dissolved and entrained water and the solvent by azeotropic means on a rotary evaporator at bath temperature 60° C. and a final vacuum of 60 mbar. The honey obtained was dried to constant mass at 80° C. under reduced pressure. This gave 5.60 g of a yellowish honey-like oil which, by HPLC, had a 92.0% by weight content of the mixture of the borates of the formulae

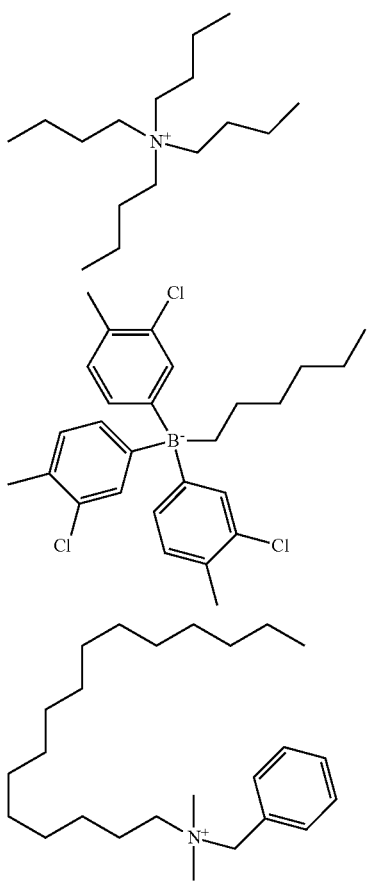

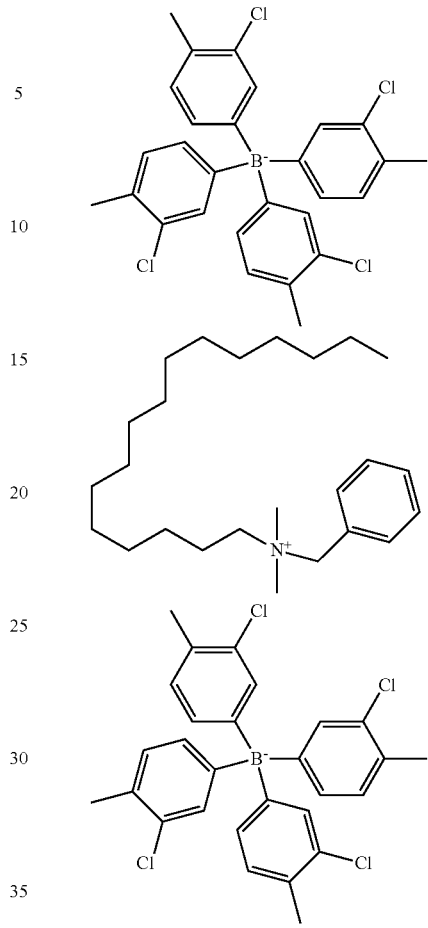

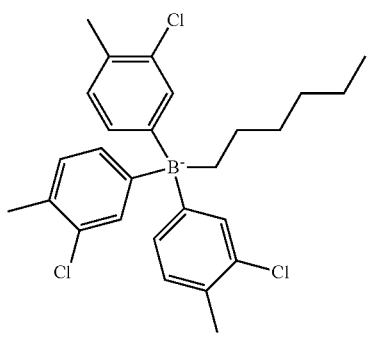

and a 0.7% by weight content of the mixture of the borates of the formulae

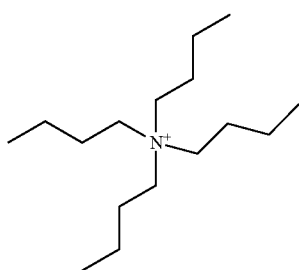

The yield was thus 88.9% of theory. By means of $^1$H NMR (CDCl$_3$, for signals see Example 1), the molar ratio of the tetrabutylammonium to benzyldimethylhexadecylammonium cations was determined to be 0.3:99.7. Likewise by means of $^1$H NMR (CDCl$_3$, for signals see Example 1), a content of 4.34% by weight of the sulphosuccinate of the formula

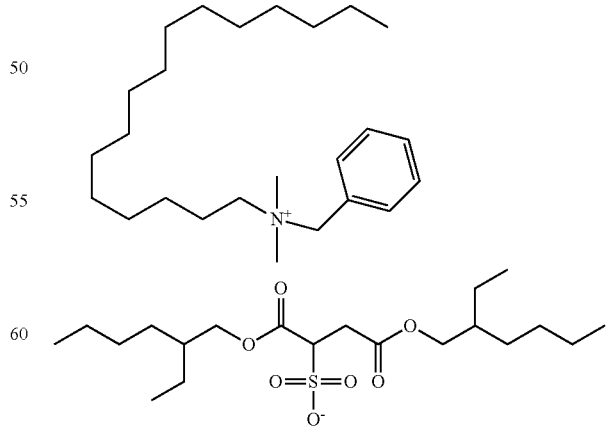

in the honey-like oil was found, i.e. 4.68% by weight based on the mixture of the borates.

$T_g$: −27° C.
Total washes: 8
Intermediate phases: 0

The product was dissolved in 10 g of butyl acetate, and hence a storage-stable solution having a concentration of 34.1% by weight was prepared.

Examples 5 to 9: Variation of Ammonium and/or Borate

Example 5

The procedure was analogous to Example 1, except that 10.0 g of tetrabutylammonium hexyltris(4-fluorophenyl) borate, 6.97 g of benzyldimethylhexadecylammonium chloride hydrate (1.05 molar equivalents) and 0.36 g of sodium bis(2-ethylhexyl)sulphosuccinate (0.05 molar equivalent) in a mixture of 50 ml of butyl acetate and 60 ml of water were used. Here too, the reactant, analogously to Example 1, contained a corresponding preparation-related proportion of the analogous tetraarylborate. For the sake of clarity, these and also the products formed therefrom are not specified in detail.

30 ml water portions were used for washing. This gave 27.5 g of a clear solution which, by $^1$H NMR (in CDCl$_3$, characteristic signals for butyl acetate: δ=4.05 ppm (t, 2H), for hexyltris(4-fluorophenyl)borate: δ=6.65 ppm (t, 6H), δ=2.20 ppm (s, 9H), for benzyldimethylhexadecylammonium: δ=6.95 ppm (d, 2H), δ=3.40 ppm (s, 2H)), had a 41.3% by weight content of the mixture of the borates of the formulae

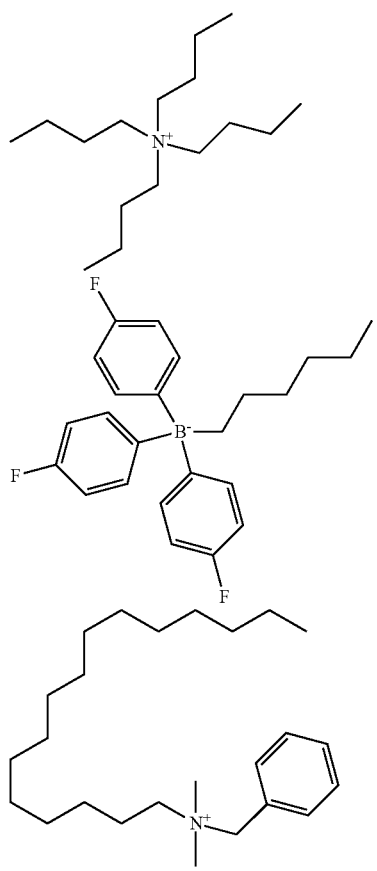

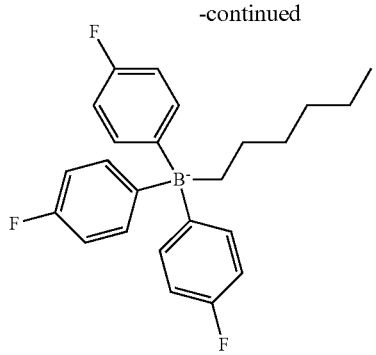

The yield was thus 96.8% of theory. By means of $^1$H NMR (in CDCl$_3$, for signals see Example 1), the molar ratio of the tetrabutylammonium to benzyldimethylhexadecylammonium cations was determined to be 1.4:98.6. Likewise by means of $^1$H NMR (in CDCl$_3$, for signals see Example 1), a content of 1.45% by weight of the sulphosuccinate of the formula

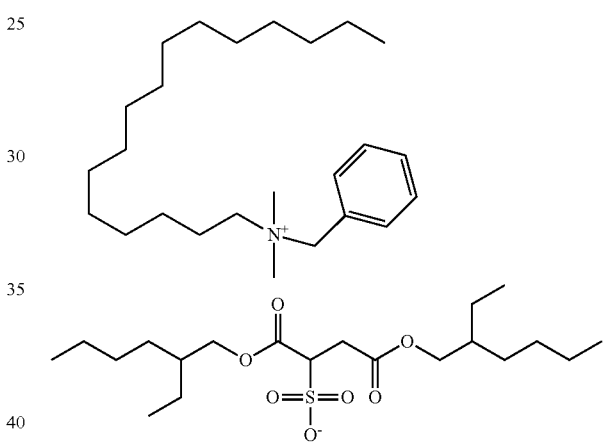

in the solution was found, i.e. 3.51% by weight based on the mixture of the borates.
Total washes: 7
Intermediate phases: 0

After evaporative concentration of a portion of the solution under reduced pressure and drying of the residue at 80° C. under reduced pressure, a colourless honey-like oil having a $T_g$ of −33° C. was obtained.

Example 6

The procedure was analogous to Example 1, except that 9.00 g of tetrabutylammonium 3-phenylpropyltris(4-fluorophenyl)borate, 5.95 g of benzyldimethylhexadecylammonium chloride hydrate (1.05 molar equivalents) and 0.31 g of sodium bis(2-ethylhexyl)sulphosuccinate (0.05 molar equivalent) in a mixture of 60 ml of butyl acetate and 75 ml of water were used. Here too, the reactant, analogously to Example 1, contained a corresponding preparation-related proportion of the analogous tetraarylborate. For the sake of clarity, these and also the products formed therefrom are not specified in detail.

50 ml water portions were used for washing. This gave 13.1 g of a clear solution which, by $^1$H NMR (in CDCl$_3$, characteristic signals for butyl acetate: δ=4.05 ppm (t, 2H), for phenylpropyltris(4-fluorophenyl)borate: δ=6.65 ppm (t, 6H), for benzyldimethylhexadecylammonium: δ=6.95 ppm (d, 2H), δ=3.40 ppm (s, 2H)), had a 26.2% by weight content of the mixture of the borates of the formulae

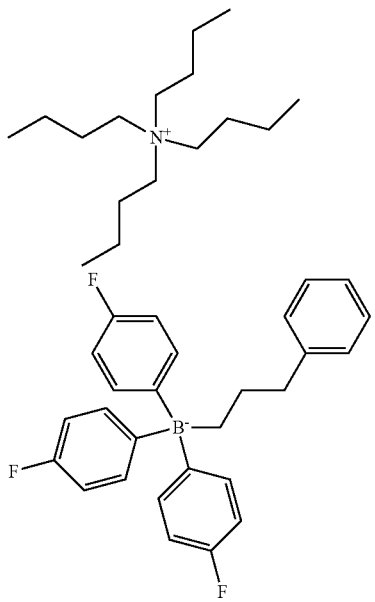

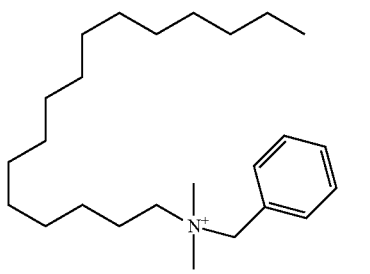

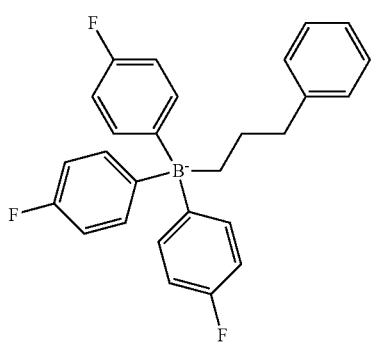

The yield was thus 97.0% of theory. By means of $^1$H NMR (in CDCl$_3$, for signals see Example 1), it was possible to detect tetrabutylammonium in a trace amount (<0.3%). The molar ratio of the tetrabutylammonium to benzyldimethylhexadecylammonium cations was thus determined to be <1:>99. Likewise by means of $^1$H NMR (in CDCl$_3$, for signals see Example 1), a content of 0.7% by weight of the sulphosuccinate of the formula

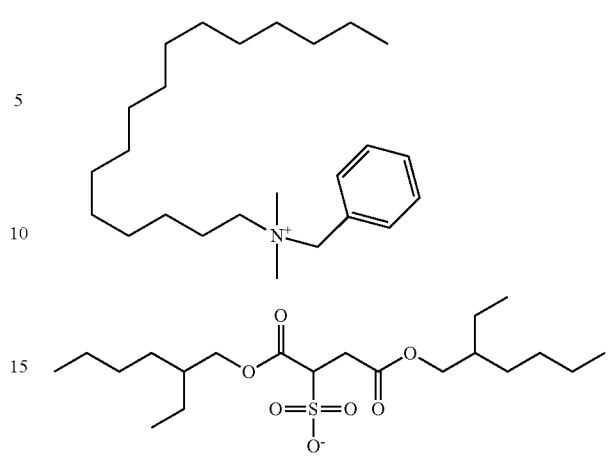

in the solution was found, i.e. 2.67% by weight based on the mixture of the borates.

Total washes: 6

Intermediate phases: 0

After evaporative concentration of a portion of the solution under reduced pressure and drying of the residue at 80° C. under reduced pressure, a colourless honey-like oil having a $T_g$ of −22° C. was obtained.

Example 7

The procedure was analogous to Example 1, except that 9.00 g of tetrabutylammonium dodecyltris(3-chloro-4-methylphenyl)borate, 4.89 g of benzyldimethylhexadecylammonium chloride hydrate (1.05 molar equivalents) and 0.25 g of sodium bis(2-ethylhexyl)sulphosuccinate (0.05 molar equivalent) in a mixture of 60 ml of butyl acetate and 75 ml of water were used. Here too, the reactant, analogously to Example 1, contained a corresponding preparation-related proportion of the analogous tetraarylborate. For the sake of clarity, these and also the products formed therefrom are not specified in detail.

50 ml water portions were used for washing. This gave 39.6 g of a clear solution which, by $^1$H NMR (in CDCl$_3$, characteristic signals for butyl acetate: δ=4.05 ppm (t, 2H), for dodecyltris(3-chloro-4-methylphenyl)borate: δ=6.85 ppm (dd, 3H), δ=2.20 ppm (s, 9H), for benzyldimethylhexadecylammonium: δ=6.95 ppm (d, 2H), δ=3.40 ppm (s, 2H)), had a 25.0% by weight content of the mixture of the borates of the formulae

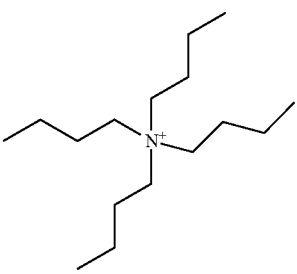

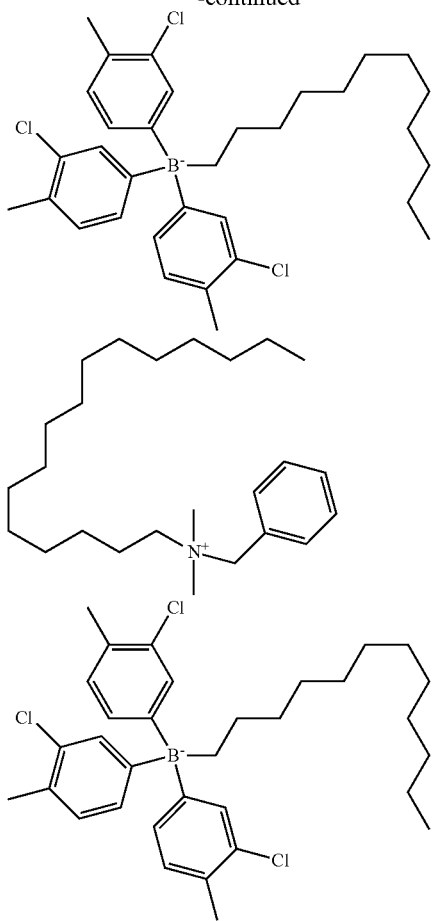

The yield was thus 95.8% of theory. By means of $^1$H NMR (in CDCl$_3$, for signals see Example 1), it was possible to detect tetrabutylammonium in a trace amount (<0.3%). The molar ratio of the tetrabutylammonium to benzyldimethylhexadecylammonium cations was thus determined to be <1:>99. Likewise by means of $^1$H NMR (in CDCl$_3$, for signals see Example 1), a content of 1.25% by weight of the sulphosuccinate of the formula

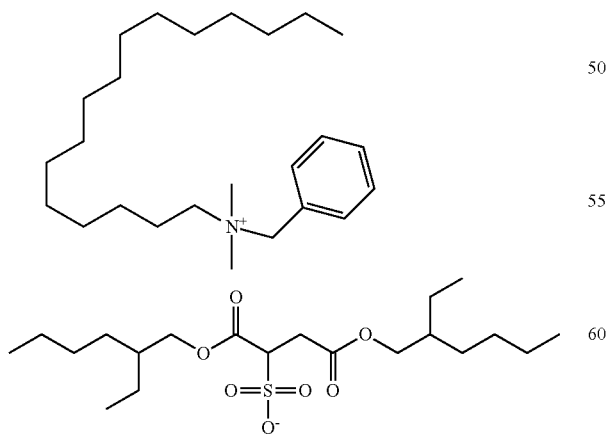

in the solution was found, i.e. 5.00% by weight based on the mixture of the borates.

Total washes: 6

Intermediate phases: 0

After evaporative concentration of a portion of the solution under reduced pressure and drying of the residue at 80° C. under reduced pressure, a yellowish honey-like oil having a $T_g$ of −47° C. was obtained.

Example 8

5.00 g of tetrabutylammonium hexyltris(3-chloro-4-methylphenyl)borate, 2.91 g of 1-hexadecyl-4-tert-butylpyridinium chloride (1.05 molar equivalents) and 0.15 g of sodium bis(2-ethylhexyl)sulphosuccinate (0.05 molar equivalent) were stirred in a mixture of 20 ml of butyl acetate and 30 ml of water at 20° C. for 2.5 h. Here too, the reactant, analogously to Example 1, contained a corresponding preparation-related proportion of the analogous tetraarylborate. For the sake of clarity, these and also the products formed therefrom are not specified in detail. The temperature was maintained in all subsequent steps. The mixture was transferred into a separating funnel and the lower aqueous phase was discharged after 10 min. The organic phase was shaken vigorously with 20 ml of water and separated again from the aqueous phase after 10 min. This procedure was repeated five times. In the last water phase, it was no longer possible to detect any chloride ions (3 ml sample+0.5 ml of 10 percent HNO$_3$+0.5 ml of 5 percent AgNO$_3$ solution). The organic phase was freed of the dissolved and entrained water and the solvent by azeotropic means on a rotary evaporator at bath temperature 60° C. and a final vacuum of 60 mbar. The honey-like substance obtained was dried to constant mass at 80° C. under reduced pressure. This gave 5.71 g of a brownish honey-like oil which, by $^1$H NMR (in CDCl$_3$, characteristic signals for butyl acetate: δ=4.05 ppm (t, 2H), for hexyltris(3-chloro-4-methylphenyl)borate: δ=6.85 ppm (dd, 3H), δ=2.20 ppm (s, 9H), for 1-hexadecyl-4-tert-butylpyridinium: δ=7.10 ppm (d, 2H), δ=3.50 ppm (m, 2H)), consisted to an extent of 96.5% by weight of a mixture of the borates of the formulae

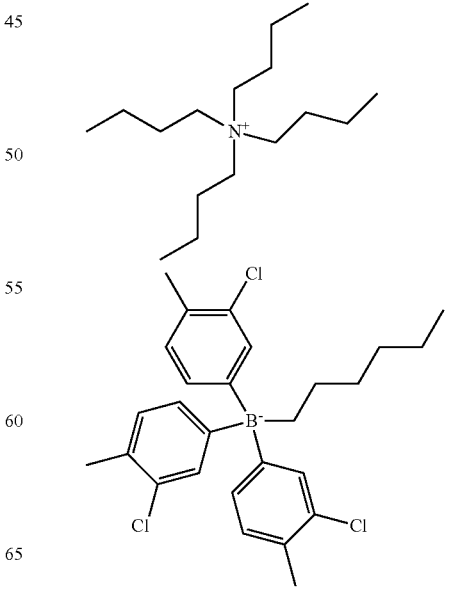

-continued

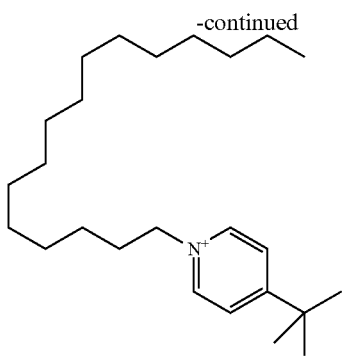

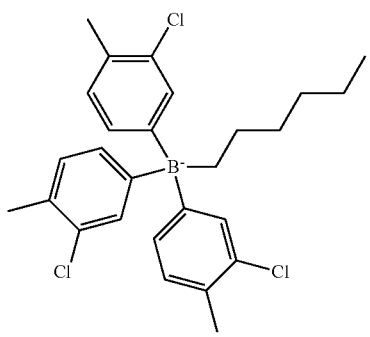

The yield was thus 94.6% of theory. By means of $^1$H NMR (in CDCl$_3$, characteristic signals for tetrabutylammonium: δ=2.55 (m, 8H), for 1-hexadecyl-4-tert-butylpyridinium: δ=7.10 ppm (d, 2H), δ=3.50 ppm (m, 2H)), the molar ratio of the tetrabutylammonium to 1-hexadecyl-4-tert-butylpyridinium cations was determined to be 3.5:96.5. Likewise by means of $^1$H NMR (in CDCl$_3$, for signals see Example 1), a content of 3.5% by weight of the bis(2-ethylhexyl)sulphosuccinate of the formula

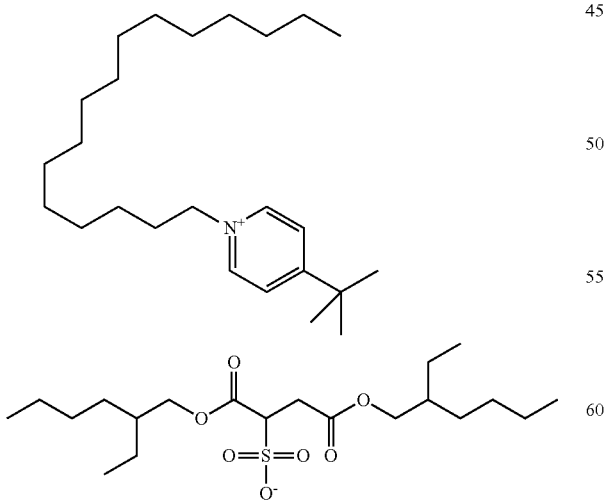

was found, i.e. 3.63% by weight based on the mixture of the borates.

$T_g$: −22° C.
Total washes: 6
Intermediate phases: 0

The 1-hexadecyl-4-tert-butylpyridinium chloride required as a reactant was prepared as follows:

A microspatula-tip of tetrabutylammonium iodide was added to 4.00 g of 4-tert-butylpyridine and 19.7 g of 1-chlorohexadecane, and the mixture was stirred at 130-135° C. for 24 h. After cooling, the pasty crystal mass obtained was boiled together with 30 ml of cyclohexane, which caused it to go partly into solution, and stirred again under cold conditions. The mixture was filtered with suction and washed with 40 ml of cyclohexane. The pasty product was finally stirred in 50 ml of diethyl ether until a suspension of good stirrability was obtained. The latter was filtered with suction and washed with 30 ml of diethyl ether. The beige solid was dried at 50° C. under reduced pressure. This gave 5.85 g (29.2% of theory) of 1-hexadecyl-4-tert-butylpyridinium chloride.

Example 9

3.50 g of tetrabutylammonium hexyltris(3-chloro-4-methylphenyl)borate, 2.15 g of 1-benzyl-3-hexadecylimidazolium chloride (1.05 molar equivalents, prepared according to Heterocycles 2010, 80, 989) and 0.11 g of sodium bis(2-ethylhexyl)sulphosuccinate (0.05 molar equivalent) were stirred in a mixture of 20 ml of butyl acetate and 30 ml of water at 20° C. for 2.5 h. Here too, the reactant, analogously to Example 1, contained a corresponding preparation-related proportion of the analogous tetraarylborate. For the sake of clarity, these and also the products formed therefrom are not specified in detail. The temperature was maintained in all subsequent steps. The mixture was transferred into a separating funnel and the lower aqueous phase was discharged after 10 min. The organic phase was shaken vigorously with 10 ml of water and separated again from the aqueous phase after 10 min. This procedure was repeated three times. In the last water phase, it was no longer possible to detect any chloride ions (3 ml sample+0.5 ml of 10 percent HNO$_3$+0.5 ml of 5 percent AgNO$_3$ solution). The organic phase was freed of the dissolved and entrained water and the solvent by azeotropic means on a rotary evaporator at bath temperature 60° C. and a final vacuum of 60 mbar. The honey-like substance obtained was dried to constant mass at 80° C. under reduced pressure. This gave 4.14 g of a yellowish honey-like oil which, by $^1$H NMR (in CDCl$_3$, characteristic signals for butyl acetate: δ=4.05 ppm (t, 2H), for hexyltris(3-chloro-4-methylphenyl)borate: δ=6.85 ppm (dd, 3H), δ=2.20 ppm (s, 9H), for 1-benzyl-3-hexadecylimidazolium: δ=4.60 ppm (s, 2H)), consisted to an extent of 95.7% by weight of a mixture of the borates of the formulae

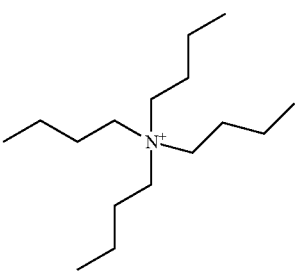

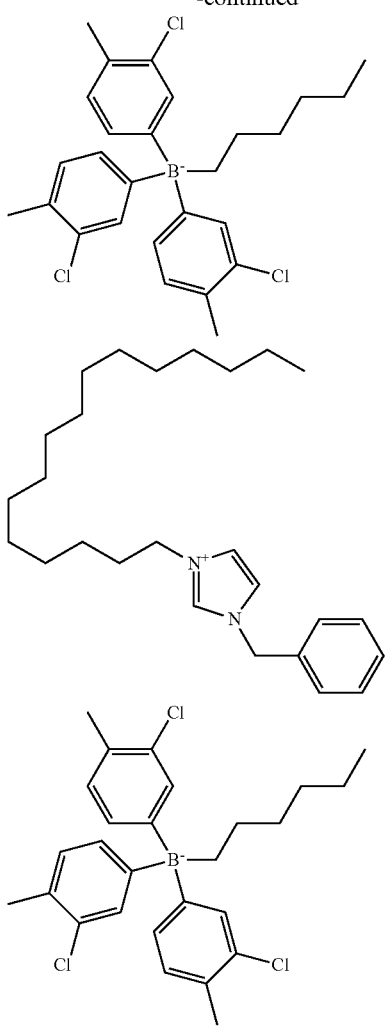

The yield was thus 94.6% of theory. By means of $^1$H NMR (in CDCl$_3$, characteristic signals for tetrabutylammonium: δ=2.55 (m, 8H), for 1-benzyl-3-hexadecylimidazolium: δ=4.60 ppm (s, 2H)), the molar ratio of the tetrabutylammonium to 1-benzyl-3-hexadecylimidazolium cations was determined to be 2.4:97.6. Likewise by means of $^1$H NMR (in CDCl$_3$, for signals see Example 1), a content of 3.5% by weight of the bis(2-ethylhexyl)sulphosuccinate of the formula

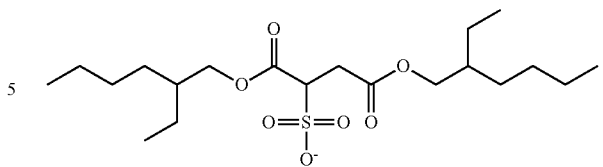

and 0.8% by weight of butyl acetate was found, i.e. 3.66% by weight based on the mixture of the borates.

T$_g$: −37° C.

Total washes: 4

Intermediate phases: 0

Examples 10 to 11: Use of Ammonium Salts Having Two Long-Chain R$^1$ and R$^2$ Radicals, for which the Addition of the Salt of the Formula (II) is Unnecessary Example 10

4.00 g of tetrabutylammonium hexyltris(3-chloro-4-methylphenyl)borate, 3.28 g of distearyldimethylammonium chloride (1.00 molar equivalent) were stirred in a mixture of 50 ml of butyl acetate and 30 ml of water at 25° C. for 5 h. Here too, the reactant, analogously to Example 1, contained a corresponding preparation-related proportion of the analogous tetraarylborate. For the sake of clarity, these and also the products formed therefrom are not specified in detail. The temperature was maintained in all subsequent steps. The mixture was transferred into a separating funnel and the lower aqueous phase was discharged after 10 min. The organic phase was shaken vigorously with 20 ml of water and separated again from the aqueous phase after 10 min. This procedure was repeated five times. In the last water phase, it was no longer possible to detect any chloride ions (3 ml sample+0.5 ml of 10 percent HNO$_3$+0.5 ml of 5 percent AgNO$_3$ solution). The organic phase was freed of the dissolved and entrained water and the solvent by azeotropic means on a rotary evaporator at bath temperature 60° C. and a final vacuum of 60 mbar. The honey-like substance obtained was dried to constant mass at 80° C. under reduced pressure. This gave 5.10 g of a yellowish honey-like oil which, by $^1$H NMR (in CDCl$_3$, characteristic signals for butyl acetate: δ=4.05 ppm (t, 2H), for hexyltris(3-chloro-4-methylphenyl)borate: δ=6.85 ppm (dd, 3H), δ=2.20 ppm (s, 9H), signal for distearyldimethylammonium: δ=1.85 ppm (s, 6H)), consisted exclusively of the borate of the formula

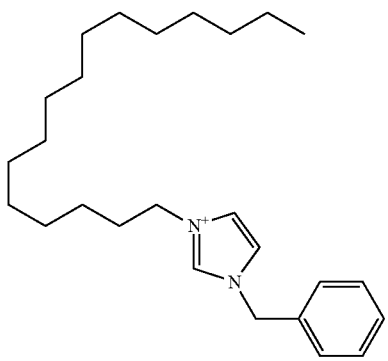

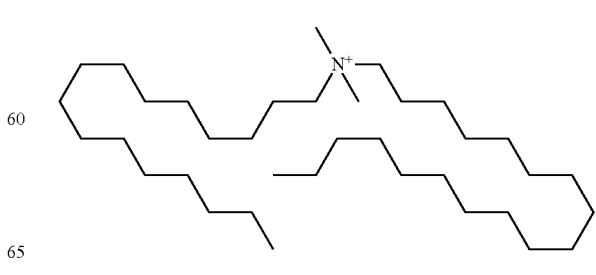

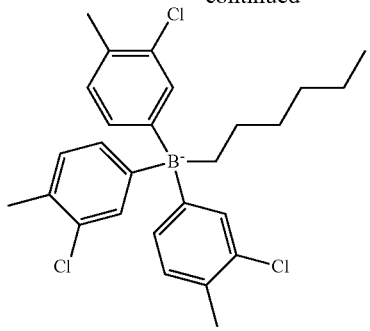

The yield was thus 89.1% of theory. The molar ratio of the tetrabutylammonium to distearyldimethylammonium cations was thus 0:100 ($^1$H NMR in CDCl$_3$, for signals see Example 1).
T$_g$: −39° C.
Total washes: 6
Intermediate phases: 0

The product was dissolved in 9 g of butyl acetate, and hence a storage-stable solution having a concentration of 36% by weight was prepared.

Example 11

3.32 g of tetrabutylammonium hexyltris(3-chloro-4-methylphenyl)borate, 2.91 g of N,N-dioctadecylpiperidinium chloride (prepared according to J. Amer. Chem. Soc. 1955, 77, 485) (1.00 molar equivalent) were stirred in a mixture of 15 ml of butyl acetate and 20 ml of water at 25° C. for 5 h. Here too, the reactant, analogously to Example 1, contained a corresponding preparation-related proportion of the analogous tetraarylborate. For the sake of clarity, these and also the products formed therefrom are not specified in detail. The temperature was maintained in all subsequent steps. The mixture was transferred into a separating funnel and the lower aqueous phase was discharged after 10 min. The organic phase was shaken vigorously with 20 ml of water and separated again from the aqueous phase after 10 min. This procedure was repeated five times. In the last water phase, it was no longer possible to detect any chloride ions (3 ml sample+0.5 ml of 10 percent HNO$_3$+0.5 ml of 5 percent AgNO$_3$ solution). The organic phase was freed of the dissolved and entrained water and the solvent by azeotropic means on a rotary evaporator at bath temperature 60° C. and a final vacuum of 60 mbar. The honey obtained was dried to constant mass at 80° C. under reduced pressure. This gave 4.47 g of a yellowish honey-like oil which, by $^1$H NMR (CDCl$_3$, characteristic signals for butyl acetate: δ=4.05 ppm (t, 2H), for hexyltris(3-chloro-4-methylphenyl)borate: δ=6.85 ppm (dd, 3H), δ=2.20 ppm (s, 9H), for dioctadecylpiperidinium: δ=2.40 ppm (m, 4H)), consisted exclusively of the borate of the formula

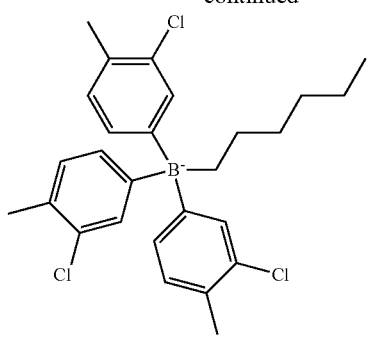

The yield was thus 90.5% of theory. The molar ratio of the tetrabutylammonium to N,N-Dioctadecylpiperidinium was thus 0:100 ($^1$H NMR in CDCl$_3$, for signals see Example 1).
T$_g$: −34° C.
Total washes: 6
Intermediate phases: 0

Example 12

2.50 g of tetrabutylammonium tetrakis(3-chloro-4-methylphenyl)borate and 2.05 g of benzyldimethylhexadecylammonium chloride hydrate (1.5 molar equivalents) were stirred in a mixture of 100 ml of butyl acetate and 100 ml of water at 70° C. for 2.5 h. This temperature was maintained in all subsequent steps. The mixture was transferred into a separating funnel and the lower cloudy aqueous phase was discharged after 10 min. The organic phase was shaken vigorously with 20 ml of water and separated again from the aqueous phase after 10 min. This procedure was repeated seven times. In the last water phase, it was no longer possible to detect any chloride ions (3 ml sample+0.5 ml of 10 percent HNO$_3$+0.5 ml of 5 percent AgNO$_3$ solution). The organic phase was dried with anhydrous magnesium sulphate, filtered and freed of the solvent on a rotary evaporator at bath temperature 60° C. and a final vacuum of 60 mbar. The honey-like substance obtained was dried to constant mass at 80° C. under reduced pressure. This gave 1.35 g of a yellowish honey-like oil which, by $^1$H NMR (in CDCl$_3$, characteristic signals for butyl acetate: δ=4.05 ppm (t, 2H), for tetrakis(3-chloro-4-methylphenyl)borate: δ=6.85 ppm (dd, 4H), δ=2.20 ppm (s, 12H), for benzyldimethylhexadecylammonium: δ=6.95 ppm (d, 2H), δ=3.40 ppm (s, 2H)), had a 96.4% by weight content of the borate of the formula

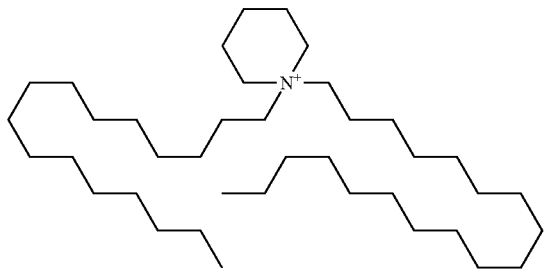

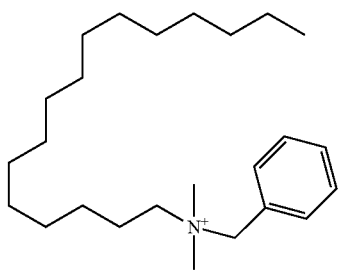

47 -continued

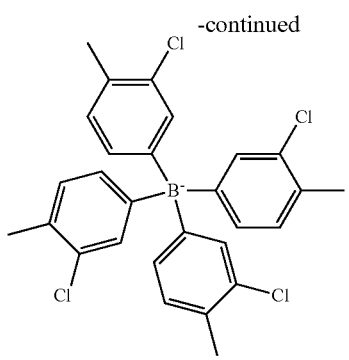

The yield was thus 46.7% of theory. The molar ratio of tetrabutylammonium to benzyldimethylhexadecylammonium was thus 0:100 ($^1$H NMR in CDCl$_3$, for signals see Example 1).

$T_g$: −2.3° C.

Total washes: 8

Intermediate phases: 0

It is shown here that even the pure tetraarylborate as the salt of an inventive cation has a $T_g$<0° C.

Further borates of the formula (Ia) are compiled in the table which follows. They can be prepared analogously to Example 1.

| Example | $R^1\!-\!\underset{R^4}{\underset{|}{\overset{R^3}{\underset{|}{N^+}}}}\!-\!R^2$ | $R^{21}\!-\!\underset{R^{24}}{\underset{|}{\overset{R^{23}}{\underset{|}{B^-}}}}\!-\!R^{22}$ |
|---|---|---|
| 13 | n-C$_{18}$H$_{37}$–N$^+$(CH$_3$)(CH$_3$)–CH$_2$C$_6$H$_5$ | tri(4-tert-butylphenyl)(n-butyl)borate |
| 14 | n-C$_{14}$H$_{29}$–N$^+$(CH$_3$)(CH$_3$)–(CH$_2$)$_3$C$_6$H$_5$ | tri(3-chloro-4-methylphenyl)(n-butyl)borate |
| 15 | n-C$_{18}$H$_{37}$–N$^+$(CH$_3$)(CH$_3$)–CH$_2$C$_6$H$_5$ | tri(3-chlorophenyl)(n-hexyl)borate |

-continued
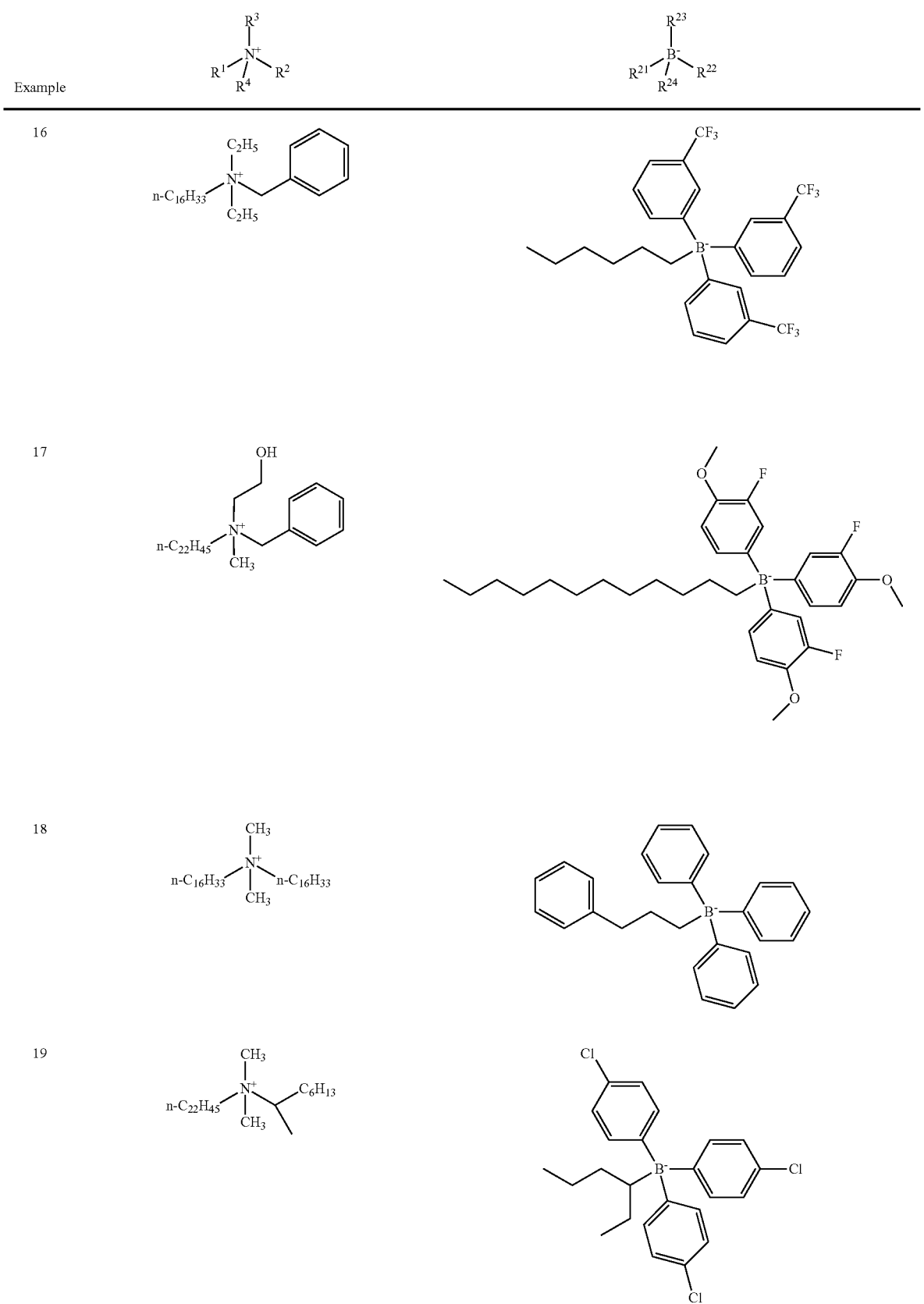

-continued

| Example | $\underset{R^4}{\overset{R^3}{\underset{|}{N^+}}}\underset{}{\overset{|}{R^2}}$ R¹ | $\underset{R^{24}}{\overset{R^{23}}{\underset{|}{B^-}}}\underset{}{\overset{|}{R^{22}}}$ R²¹ |
|---|---|---|
| 20 | n-C₁₄H₂₉—N⁺(CH₃)₂—(CH₂)₈—O—CH₃ | hexyl-B⁻ with three (3-chloro-4-methylphenyl) groups |
| 21 | n-C₁₈H₃₇-N⁺(pyrrolidine)-CH₂-phenyl | butyl-B⁻ with three (3-chloro-4-methylphenyl) groups |
| 22 | n-C₁₆H₃₃-N⁺(morpholine)-(CH₂)₃-phenyl | hexyl-B⁻ with three (4-biphenyl) groups |
| 23 | n-C₁₆H₃₃-N⁺(morpholine)-CH₂-CH(C₂H₅)-C₄H₉ | (3-phenylpropyl)-B⁻ with three (4-fluorophenyl) groups |

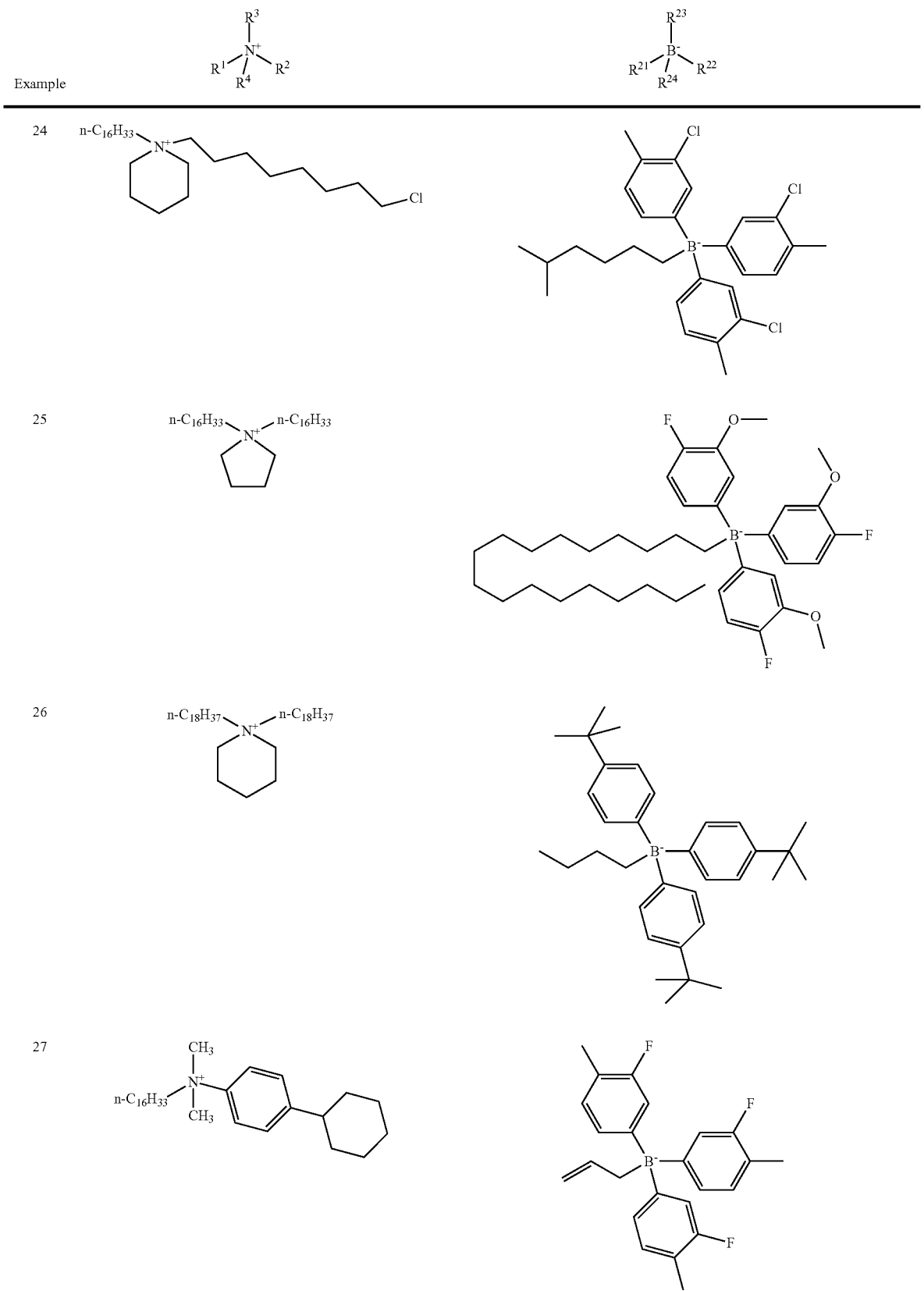

-continued
| Example | $\begin{array}{c} R^3 \\ | \\ R^1-N^+-R^2 \\ | \\ R^4 \end{array}$ | $\begin{array}{c} R^{23} \\ | \\ R^{21}-B^--R^{22} \\ | \\ R^{24} \end{array}$ |
|---|---|---|
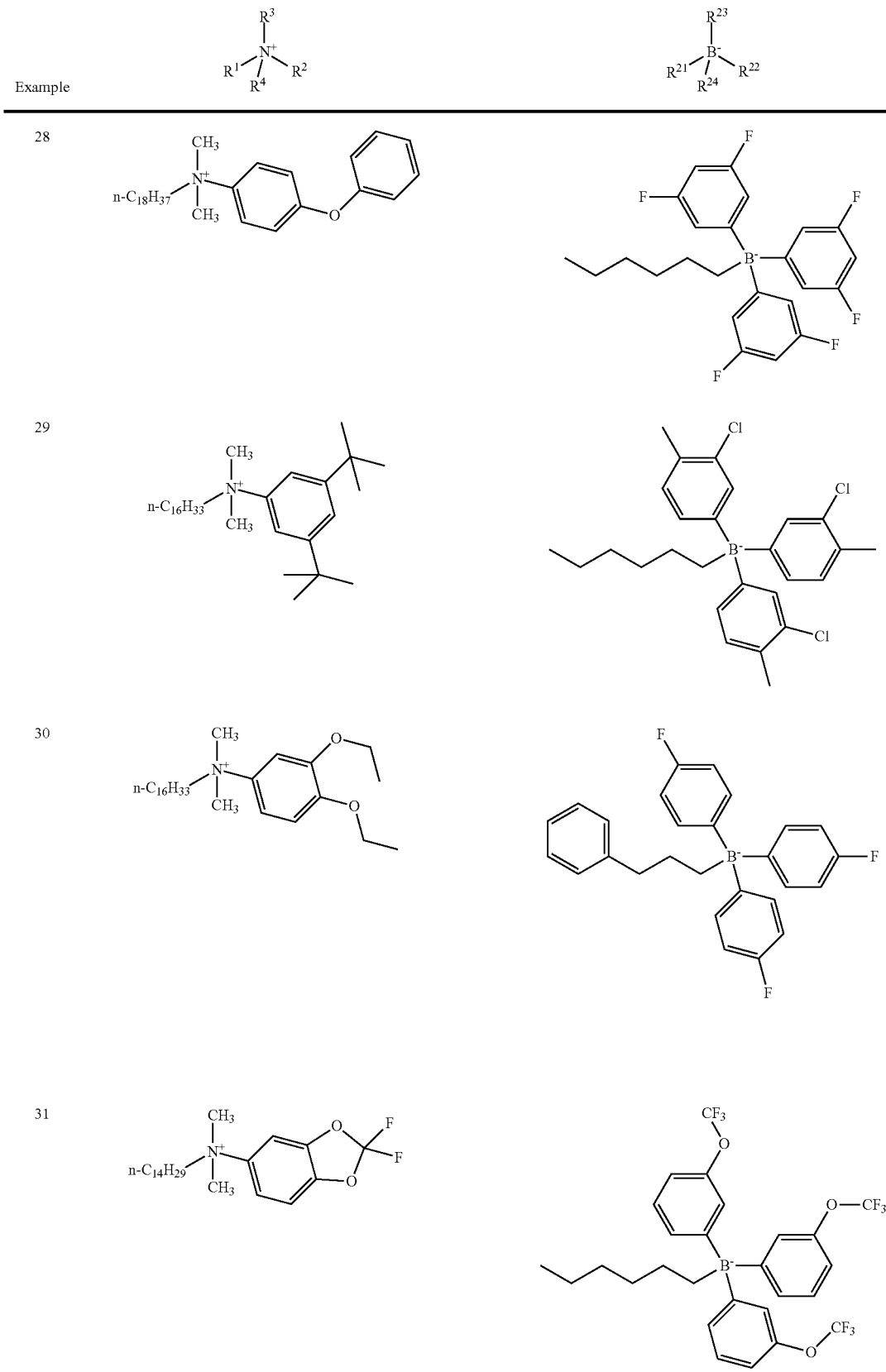

-continued
| Example | $\begin{smallmatrix}&&R^3\\&|\\R^1-&N^+-R^2\\&|\\&R^4\end{smallmatrix}$ | $\begin{smallmatrix}&&R^{23}\\&|\\R^{21}-&B^--R^{22}\\&|\\&R^{24}\end{smallmatrix}$ |
|---|---|---|
| 32 | 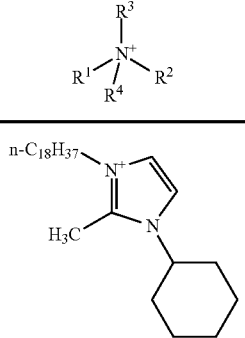 | 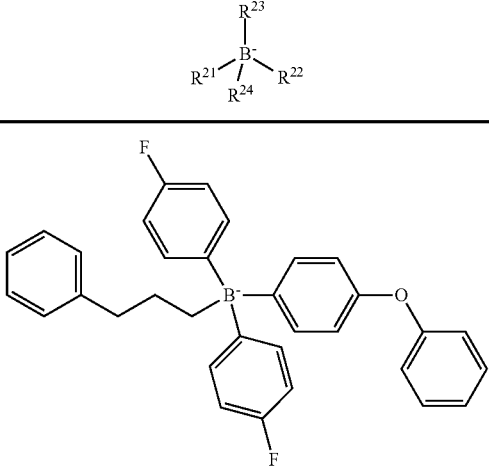 |
| 33 | 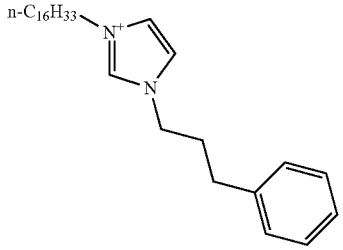 | 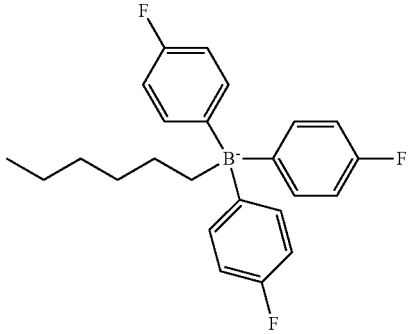 [SMILES: CCCCCC[B-](c1ccc(F)cc1)(c1ccc(F)cc1)c1ccc(F)cc1] |
| 34 | 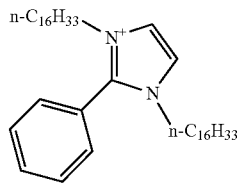 | 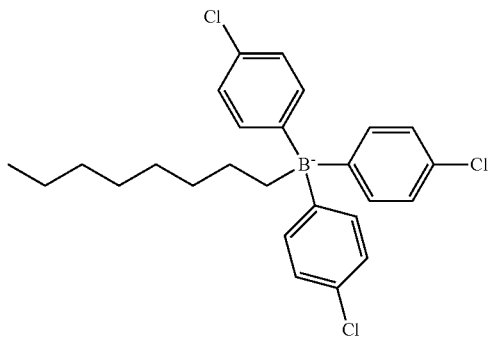 [SMILES: CCCCCCCC[B-](c1ccc(Cl)cc1)(c1ccc(Cl)cc1)c1ccc(Cl)cc1] |
| 35 | 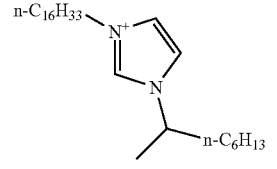 | 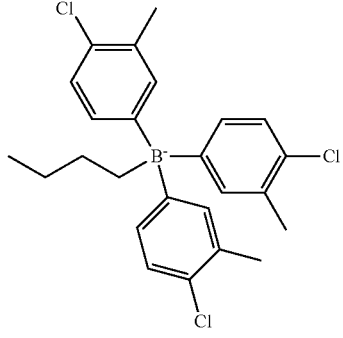 [SMILES: CCCC[B-](c1ccc(Cl)c(C)c1)(c1ccc(Cl)c(C)c1)c1ccc(Cl)c(C)c1] |

-continued
| Example | $\begin{array}{c} R^3 \\ | \\ R^1-N^+-R^2 \\ | \\ R^4 \end{array}$ | $\begin{array}{c} R^{23} \\ | \\ R^{21}-B^--R^{22} \\ | \\ R^{24} \end{array}$ |
|---|---|---|
| 36 | 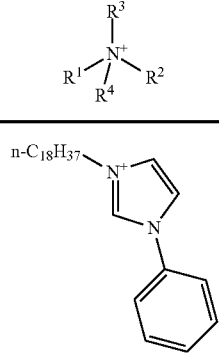 | 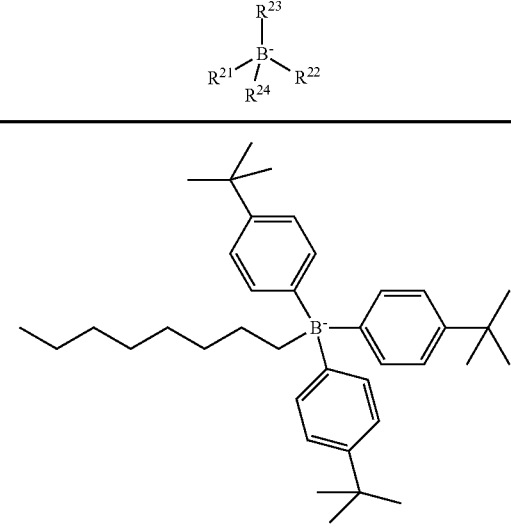 |
| 37 | 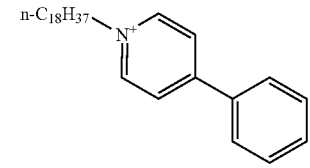 | 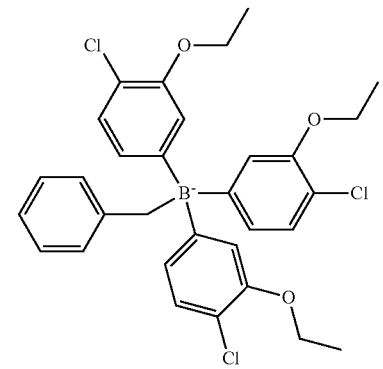 [SMILES: CCOc1cc([B-](Cc2ccccc2)(c2ccc(Cl)c(OCC)c2)c2ccc(Cl)c(OCC)c2)ccc1Cl] |
| 38 | 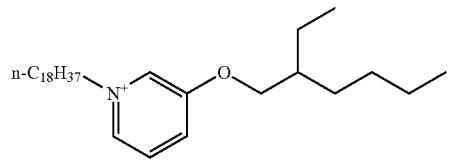 | 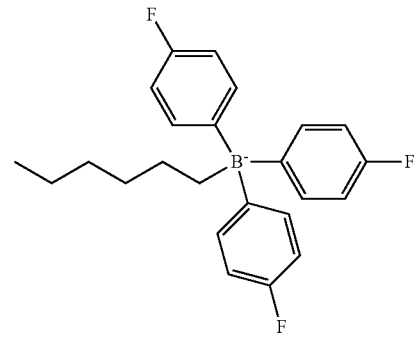 [SMILES: CCCCCC[B-](c1ccc(F)cc1)(c1ccc(F)cc1)c1ccc(F)cc1] |
| 39 | 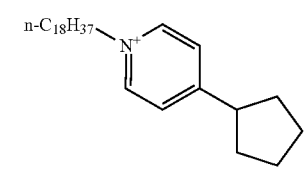 | 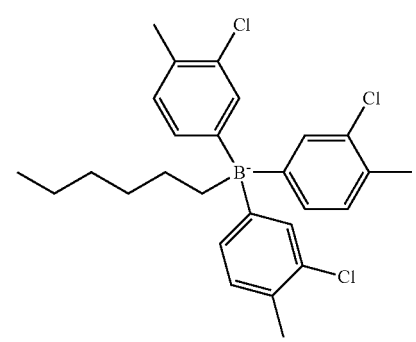 [SMILES: CCCCCC[B-](c1ccc(C)c(Cl)c1)(c1ccc(C)c(Cl)c1)c1ccc(C)c(Cl)c1] |

| Example | $\begin{array}{c} R^3 \\ | \\ R^1\!\!-\!\!\overset{+}{N}\!\!-\!\!R^2 \\ | \\ R^4 \end{array}$ | $\begin{array}{c} R^{23} \\ | \\ R^{21}\!\!-\!\!\overset{-}{B}\!\!-\!\!R^{22} \\ | \\ R^{24} \end{array}$ |
|---|---|---|
| 40 | 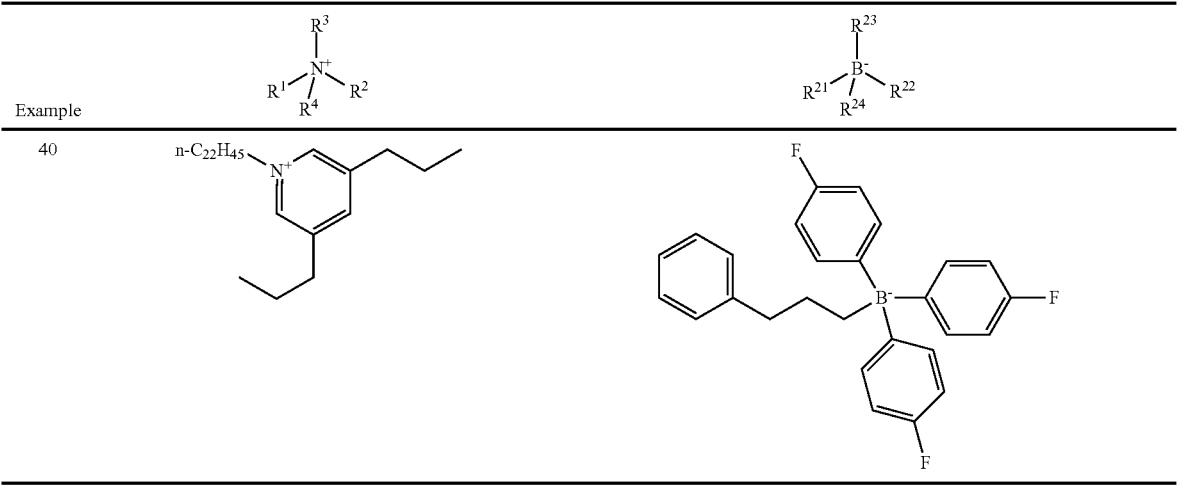 | |

Any ammonium ions present and of the formula

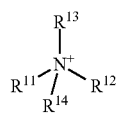

corresponding to part of the formula (IIIa) or (IIIb)
are tetramethylammonium, tetraethylammonium, tetrapropylammonium or tetrabutylammonium;
any borates present and of the formula

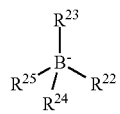

corresponding to part of the formula (Ib)
are the borates listed in the table, with the proviso that the fourth radicals too is an aryl radical. For Example 14, for example, the latter is then a borate of the formula

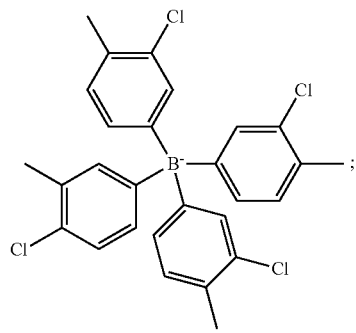 [SMILES: Cc1cc([B-](c2ccc(C)c(Cl)c2)(c2ccc(C)c(Cl)c2)c2ccc(C)c(Cl)c2)ccc1Cl]

any anions present An⁻, corresponding to part of the formula (II), are preferably bis(2-ethylhexyl)sulphosuccinate and sec-dodecylbenzenesulphonate.

Comparative Examples 1 to 5: Preparation Method

Comparative Example 1

50.0 g of tetrabutylammonium hexyltris(3-chloro-4-methylphenyl)borate and 30.4 g of benzyldimethylhexadecylammonium chloride hydrate (1.05 molar equivalents) were stirred in a mixture of 150 ml of butyl acetate and 175 ml of water at room temperature for 3 h. Here too, the reactant, analogously to Example 1, contained a corresponding preparation-related proportion of the analogous tetraarylborate. For the sake of clarity, these and also the products formed therefrom are not specified in detail. The mixture was transferred into a separating funnel and the lower aqueous phase was discharged after 30 min. The organic phase was stirred with 80 ml of water for 30 min and separated again from the aqueous phase in a separating funnel after 30 min. This procedure was repeated three times. In the last water phase, it was still possible to detect a high level of chloride ions (3 ml sample+0.5 ml of 10 percent $HNO_3$+0.5 ml of 5 percent $AgNO_3$ solution). Therefore, the organic phase was stirred again with 80 ml of water for 30 min and transferred into a separating funnel. The phase separation now proceeded, but only very slowly and incompletely. A gel-like third phase had formed between the phases. This operation was repeated five times, with increasing volume of the gel-like phase in the first few washes, but ultimately with decreasing volume again, such that it was possible to completely remove the water phase again in the last wash. This last water phase was also the first in which no chloride ions were detectable any longer. The organic phase was freed of the dissolved and entrained water by azeotropic means on a rotary evaporator at bath temperature 60° C. and a final vacuum of 60 mbar. This gave 109.8 g of a clear solution which, by HPLC, had a 47.5% by weight content of the borate of the formula

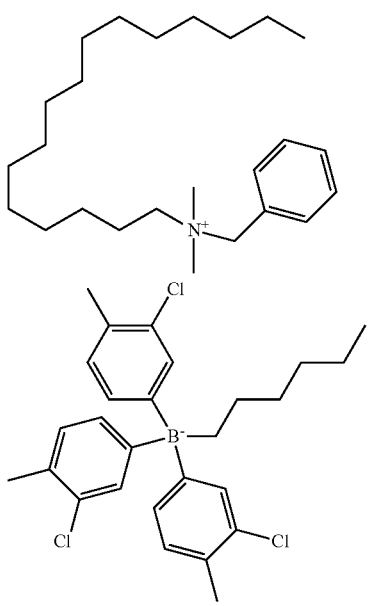

and a 0.1% by weight content of the borate of the formula

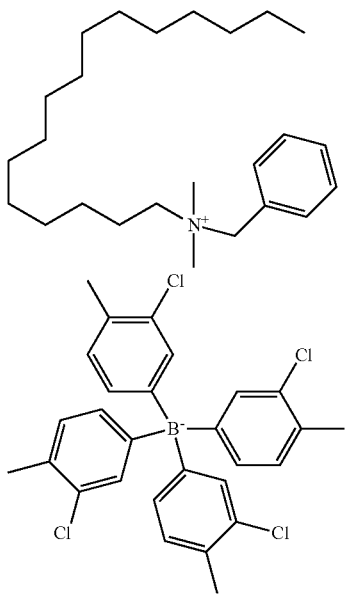

The yield was thus 96.2% of theory. By means of $^1$H NMR (in CDCl$_3$, for signals see Example 1), it was not possible to detect any tetrabutylammonium ion.

Total washes: 10

Intermediate phases: 5

Compared to Example 1, the poor reaction procedure with inadequate phase separations (intermediate phases) when no inventive salt of the formula (II) is added is shown here.

In all the examples that follow too, the tetrabutylammonium hexyltris(3-chloro-4-methylphenyl)borate reactant contained a corresponding preparation-related proportion of the analogous tetraarylborate. However, for the sake of clarity, this is not stated again hereinafter.

Comparative Example 2

100 g of tetrabutylammonium hexyltris(3-chloro-4-methylphenyl)borate and 57.9 g of benzyldimethylhexadecylammonium chloride hydrate (1.00 molar equivalent) were stirred in a mixture of 450 ml of butyl acetate and 300 ml of water at room temperature for 3 h. Here too, the reactant, analogously to Example 1, contained a corresponding preparation-related proportion of the analogous tetraarylborate. For the sake of clarity, these and also the products formed therefrom are not specified in detail.

2 g of sodium sulphate were added and the mixture was stirred for a further hour. The mixture was transferred into a separating funnel and the lower aqueous phase was discharged after 30 min. The organic phase was stirred with a solution of 2 g of sodium sulphate in 250 ml of water for 30 min and separated again from the aqueous phase in a separating funnel after 30 min. This procedure was repeated, but a third phase now occurred between the organic phase and the aqueous phase, and was not discharged together with the water phase. Twice, the organic phase was stirred with 250 ml of water for 30 min and, finally, the water phase was discharged. In the last water phase, it was still possible to detect a distinct level of chloride and sulphate ions (3 ml sample+0.5 ml of 10 percent HNO$_3$+0.5 ml of 5 percent AgNO$_3$ solution or 3 ml sample+0.5 ml of 10 percent BaCl$_2$ solution). Four more times, the organic phase was stirred with 250 ml of water for 30 min and, finally, the water phase was discharged. In the last water phase, no chloride and sulphate ions were detectable any longer. The organic phase was freed of the dissolved and entrained water by azeotropic means on a rotary evaporator at bath temperature 60° C. and a final vacuum of 60 mbar. This gave 412.6 g of a clear solution which, by HPLC, had a 26.8% by weight content of the mixture of the borates of the formulae

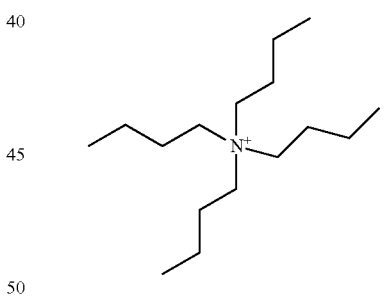

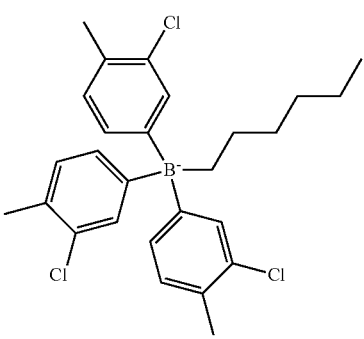

-continued

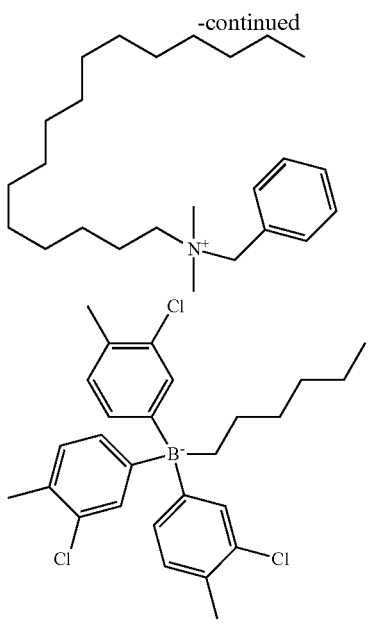

The yield was thus 99.4% of theory. By means of $^1$H NMR (in CDCl$_3$, for signals see Example 1), the molar ratio of the tetrabutylammonium to benzyldimethylhexadecylammonium cations was determined to be 6:94.
Total washes: 8
Intermediate phases: 1

Compared to Example 1, the poor reaction procedure with inadequate phase separations (intermediate phase) and the undesirably high proportion of the tetrabutylammonium ion in the end product when an inorganic salt is used rather than the inventive salt of the formula (II) are shown here.

Comparative Example 3

100 g of tetrabutylammonium hexyltris(3-chloro-4-methylphenyl)borate and 60.8 g of benzyldimethylhexadecylammonium chloride hydrate (1.05 molar equivalents) were stirred in a mixture of 300 ml of butyl acetate and 350 ml of water at room temperature for 2 h. 55 ml of a 10% by weight aqueous sodium chloride solution were added and the mixture was stirred for a further hour. Here too, the reactant, analogously to Example 1, contained a corresponding preparation-related proportion of the analogous tetraarylborate. For the sake of clarity, these and also the products formed therefrom are not specified in detail. The mixture was transferred into a separating funnel and the lower aqueous phase was discharged after 30 min. The organic phase was stirred with a mixture of 170 ml of water and 25 ml of 10% by weight aqueous sodium chloride solution for 30 min and separated again from the aqueous phase in a separating funnel after 30 min. This procedure was repeated, and, in contrast to Comparative Example 2, no third phase occurred between the organic phase and the aqueous phase. Twice, the organic phase was stirred with 170 ml of water for 30 min and, finally, the water phase was discharged. In the last water phase, it was still possible to detect a distinct level of chloride ions (3 ml sample+0.5 ml of 10 percent HNO$_3$+0.5 ml of 5 percent AgNO$_3$ solution). Four more times, the organic phase was stirred with 170 ml of water for 30 min and, finally, the water phase was discharged. In the last water phase, no chloride ions were detectable any longer. The organic phase was freed of the dissolved and entrained water by azeotropic means on a rotary evaporator at bath temperature 60° C. and a final vacuum of 60 mbar. This gave 207.0 g of a clear solution which, by HPLC, had a 45.8% by weight content of the mixture of the borates of the formulae

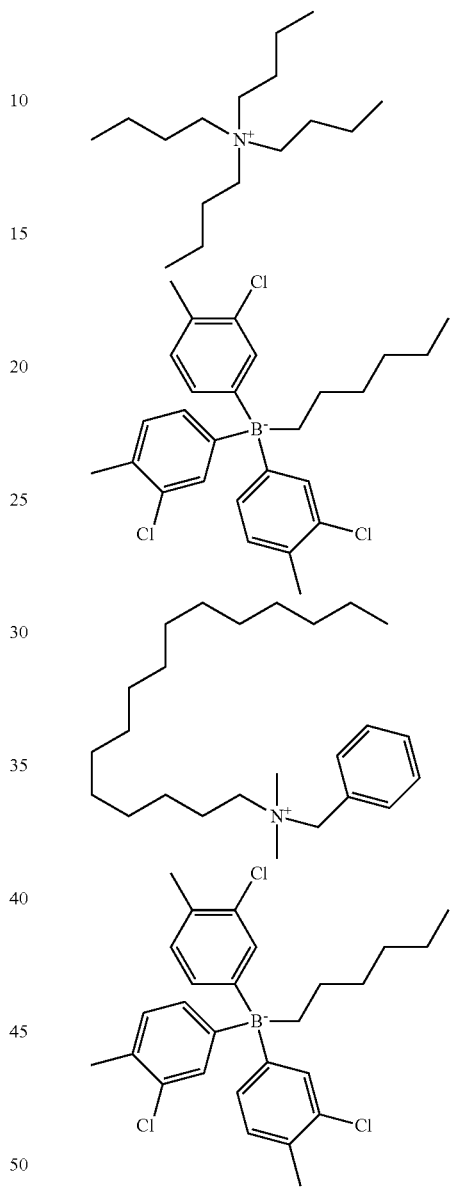

The yield was thus 87.4% of theory. By means of $^1$H NMR (in CDCl$_3$, for signals see Example 1), the molar ratio of the tetrabutylammonium to benzyldimethylhexadecylammonium cations was determined to be 4:96.
Total washes: 8
Intermediate phases: 0

Compared to Example 1, the undesirably high proportion of the tetrabutylammonium ion in the end product and the relatively low yield when an inorganic salt is used rather than the inventive salt of the formula (II) are shown here.

Comparative Example 4

750 g of tetrabutylammonium hexyltris(3-chloro-4-methylphenyl)borate and 455 g of benzyldimethylhexadecylammonium chloride hydrate (1.05 molar equivalents) were stirred in a mixture of 2300 ml of butyl acetate and 2500 ml of water in a 6 l flange apparatus. Here too, the reactant, analogously to Example 1, contained a corresponding preparation-related proportion of the analogous tetraarylborate. For the sake of clarity, these and also the products formed therefrom are not specified in detail. The mixture was heated to 45-50° C. over the course of 45 min and stirred at this temperature for 2 h. The temperature of 45-50° C. was maintained in all the subsequent steps. 400 ml of 10% by weight aqueous sodium sulphate solution were added. After stirring for 30 min, the stirrer was switched off. After 30 min, the lower aqueous phase was discharged through the base valve. The organic phase was stirred with a mixture of 1000 ml of water and 150 ml of 10% by weight aqueous sodium sulphate solution for 30 min. The stirrer was switched off and, after 30 min, the lower aqueous phase was discharged. The operation was repeated twice, except that a mixture of 1000 ml of water and 75 ml of 10% by weight aqueous sodium sulphate solution was used here. In both cases, a third phase (volume about 650 ml) occurred between the organic phase and the aqueous phase, but was not discharged together with the water phase. Twice, the organic phase was stirred with 1000 ml of water for 30 min and, finally, after no stirring for 30 minutes, the water phase was discharged. In the last water phase, it was still possible to detect a distinct level of chloride and sulphate ions (3 ml sample+0.5 ml of 10 percent $HNO_3$+0.5 ml of 5 percent $AgNO_3$ solution or 3 ml sample+0.5 ml of 10 percent $BaCl_2$ solution). Four more times, the organic phase was stirred with 1000 ml of water for 30 min and, finally, after no stirring for 30 minutes, the water phase was discharged. In the last water phase, no chloride and sulphate ions were detectable any longer. The organic phase, in two portions, was freed of the dissolved and entrained water by azeotropic means on a rotary evaporator at bath temperature 60° C. and a final vacuum of 60 mbar. This gave 1462 g of a clear solution which, by HPLC, had a 54.1% by weight content of the mixture of the borates of the formulae

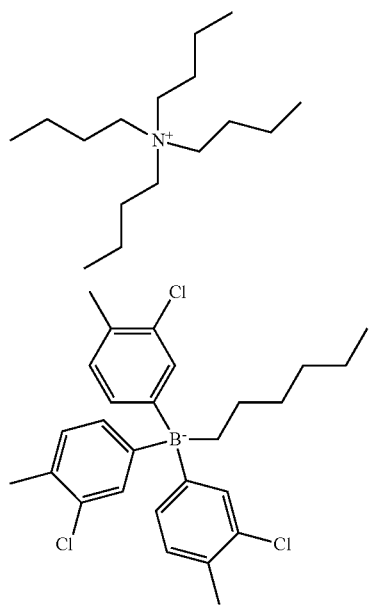

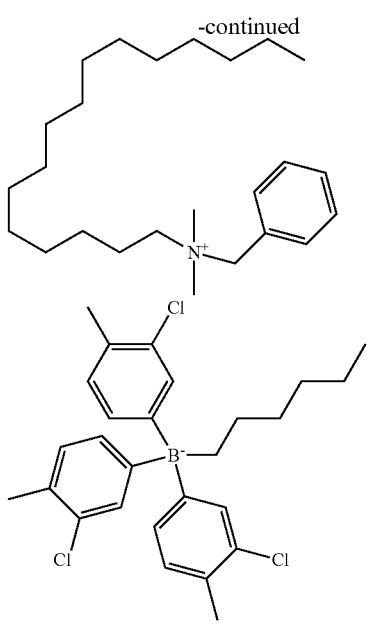

The yield was thus 98.2% of theory. By means of $^1$H NMR (in $CDCl_3$, for signals see Example 1), the molar ratio of the tetrabutylammonium to benzyldimethylhexadecylammonium cations was determined to be 5:95.
Total washes: 9
Intermediate phases: 2

Compared to Example 1, the poor reaction procedure with inadequate phase separations (intermediate phases) and the undesirably high proportion of the tetrabutylammonium ion in the end product when an inorganic salt is used rather than the inventive salt of the formula (II) and a higher temperature is employed are shown here.

Comparative Example 5

500 g of tetrabutylammonium hexyltris(3-chloro-4-methylphenyl)borate and 304 g of benzyldimethylhexadecylammonium chloride hydrate (1.05 molar equivalents) were stirred in a mixture of 1170 ml of butyl acetate and 1700 ml of water in a 6 l flange apparatus. Here too, the reactant, analogously to Example 1, contained a corresponding preparation-related proportion of the analogous tetraarylborate. For the sake of clarity, these and also the products formed therefrom are not specified in detail. The mixture was heated to 45-50° C. over the course of 45 min and stirred at this temperature for 2 h. The temperature of 45-50° C. was maintained in all the subsequent steps. 270 ml of 10% by weight aqueous sodium chloride solution were added. After stirring for 30 min, the stirrer was switched off. After 30 min, the lower aqueous phase was discharged through the base valve. The organic phase was stirred with a mixture of 415 ml of water and 50 ml of 10% by weight aqueous sodium chloride solution for 30 min. The stirrer was switched off and, after 30 min, the lower aqueous phase was discharged. The operation was repeated twice, except that a mixture of 415 ml of water and 25 ml of 10% by weight aqueous sodium chloride solution was used here. In both cases, no third phase occurred between the organic phase and the aqueous phase. Four times, the organic phase was stirred with 415 ml of water for 30 min and, finally, after no stirring for 30 minutes, the water phase was discharged. In the last water phase, it was still possible to detect a distinct level of chloride ions (3 ml sample+0.5 ml of 10 percent HNO$_3$+0.5 ml of 5 percent AgNO$_3$ solution). Four more times, the organic phase was stirred with 415 ml of water for 30 min and, finally, after no stirring for 30 minutes, the water phase was discharged. In the last water phase, no chloride ions were detectable any longer. The organic phase was freed of the dissolved and entrained water by azeotropic means on a rotary evaporator at bath temperature 60° C. and a final vacuum of 60 mbar. This gave 856.3 g of a clear solution which, by HPLC, had a 59.2% by weight content of the mixture of the borates of the formulae

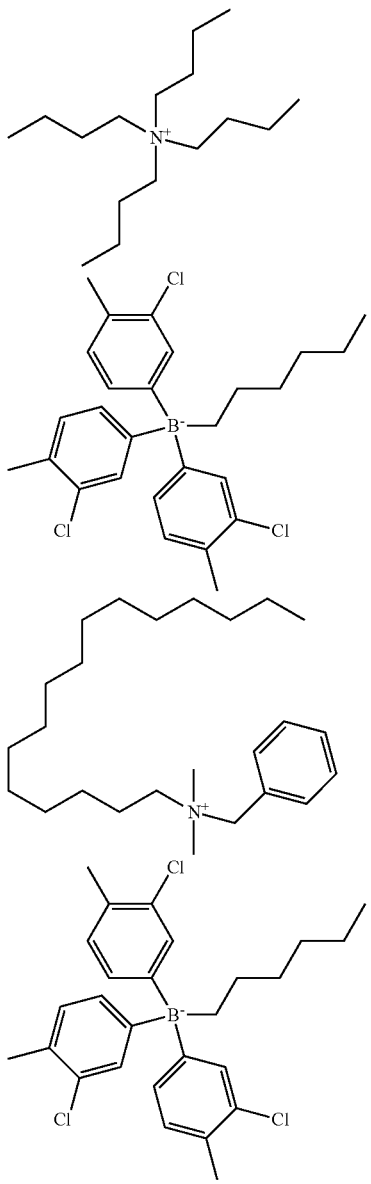

The yield was thus 95.6% of theory. By means of $^1$H NMR (in CDCl$_3$, for signals see Example 1), the molar ratio of tetrabutylammonium to benzyldimethylhexadecylammonium was determined to be 10:90.

Total washes: 11
Intermediate phases: 0

Compared to Example 1, the poor reaction procedure with a much greater number of water washes and the undesirably high proportion of the tetrabutylammonium ion in the end product when an inorganic salt is used rather than the inventive salt of the formula (II) and a higher temperature is employed are shown here.

Comparative Example 6 to 7: with Noninventive Ammonium and Pyridinium Ions

Comparative Example 6

5.00 g of tetrabutylammonium hexyltris(3-chloro-4-methylphenyl)borate and 2.75 g of 1-hexadecylpyridinium chloride (1.10 molar equivalents) were stirred in a mixture of 40 ml of butyl acetate and 25 ml of water at 20° C. for 3 h. Here too, the reactant, analogously to Example 1, contained a corresponding preparation-related proportion of the analogous tetraarylborate. For the sake of clarity, these and also the products formed therefrom are not specified in detail. The temperature was maintained in all subsequent steps. The mixture was transferred into a separating funnel and the lower aqueous phase was discharged after 10 min. The organic phase was shaken vigorously with 25 ml of water and separated again from the aqueous phase after 10 min. This procedure was repeated six times. After only the fourth water wash, it was no longer possible to detect any chloride ions in the water phase (3 ml sample+0.5 ml of 10 percent HNO$_3$+0.5 ml of 5 percent AgNO$_3$ solution). The organic phase was freed of the dissolved and entrained water and the solvent by azeotropic means on a rotary evaporator at bath temperature 60° C. and a final vacuum of 60 mbar. The waxy substance obtained was dried to constant mass at 80° C. under reduced pressure. This gave 4.96 g of a yellowish wax which, by $^1$H NMR (in CDCl$_3$, characteristic signals for butyl acetate: δ=4.05 ppm (t, 2H), for hexyltris(3-chloro-4-methylphenyl)borate: δ=6.85 ppm (dd, 3H), δ=2.20 ppm (s, 9H), for 1-hexadecylpyridinium: δ=6.98 ppm (d, 2H), δ=3.50 ppm (m, 2H)), contained 6.4% butyl acetate and hence consisted to an extent of 93.6% by weight of a mixture of the borates of the formulae

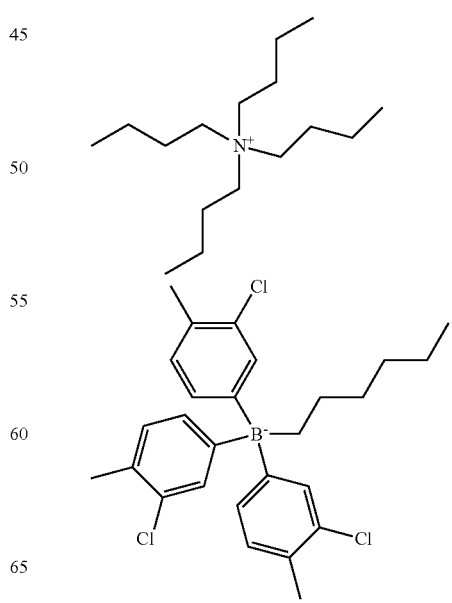

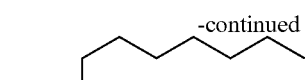

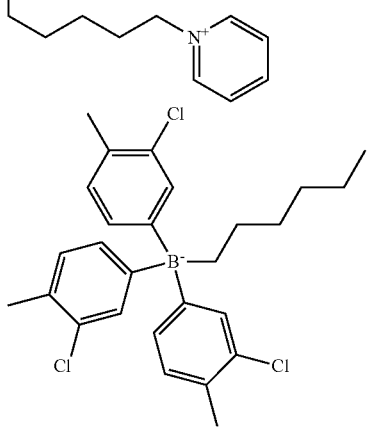

The yield was thus 85.4% of theory. By means of $^1$H NMR (in CDCl$_3$, characteristic signals for tetrabutylammonium: δ=2.55 (m, 8H), for 1-hexadecylpyridinium: δ=6.98 ppm (d, 2H), δ=3.50 ppm (m, 2H)), the molar ratio of tetrabutylammonium to 1-hexadecylpyridinium was determined to be 43:57.
Total washes: 7
Intermediate phases: 0

A comparably poor result is achieved when 1-docosylpyridinium bromide is used rather than 1-hexadecylpyridinium chloride.

Compared to Example 8, it is shown here that the cation exchange does not take place in the required manner when the pyridinium salt with long-chain substitution does not bear any inventive additional substituent in the ring. This is all the more surprising in that an even greater excess of the pyridinium salt with long-chain substitution was used here compared to Example 7.

Comparative Example 7

25.0 g of tetrabutylammonium hexyltris(3-chloro-4-methylphenyl)borate, 14.8 g of methyltrioctylammonium chloride (1.05 molar equivalents) and 0.78 g of sodium bis(2-ethylhexyl)sulphosuccinate (0.05 molar equivalent) were stirred in a mixture of 75 ml of butyl acetate and 85 ml of water at 20° C. for 3 h. Here too, the reactant, analogously to Example 1, contained a corresponding preparation-related proportion of the analogous tetraarylborate. For the sake of clarity, these and also the products formed therefrom are not specified in detail. The temperature was maintained in all subsequent steps. The mixture was transferred into a separating funnel and the lower aqueous phase was discharged after 20 min. The organic phase was shaken vigorously with 40 ml of water and separated again from the aqueous phase after 20 min. This procedure was repeated four times. In the last water phase, it was no longer possible to detect any chloride ions (3 ml sample+0.5 ml of 10 percent HNO$_3$+0.5 ml of 5 percent AgNO$_3$ solution). The organic phase was freed of the dissolved and entrained water by azeotropic means on a rotary evaporator at bath temperature 60° C. and a final vacuum of 60 mbar. This gave 46.7 g of a solution which, by $^1$H NMR (in CDCl$_3$, characteristic signals for butyl acetate: δ=4.05 ppm (t, 2H), for hexyltris(3-chloro-4-methylphenyl)borate: δ=6.85 ppm (dd, 3H), 5=2.20 ppm (s, 9H), for methyltrioctylammonium: δ=1.90 ppm (s, 3H)), consisted to an extent of 55.7% by weight of a mixture of the borates of the formulae

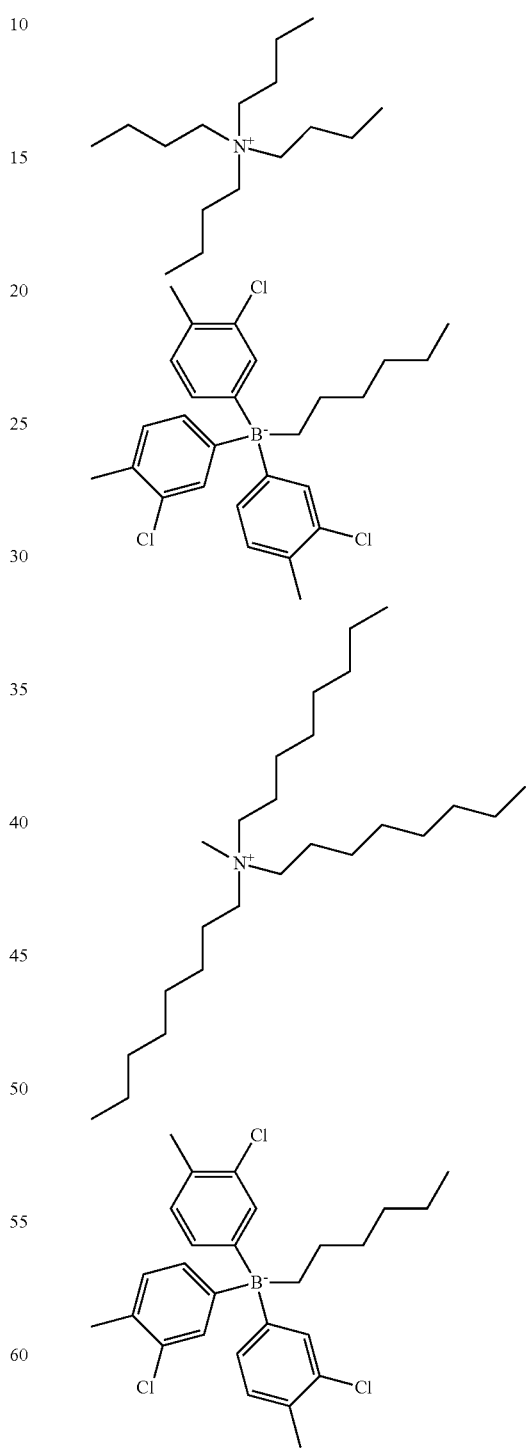

The yield was thus 86.6% of theory. By means of $^1$H NMR (in CDCl$_3$, characteristic signals for tetrabutylammonium: δ=2.55 (m, 8H), for methyltrioctylammonium: δ=1.90 ppm (s, 3H)), the molar ratio of tetrabutylammonium to methyltrioctylammonium was determined to be 19:81. Likewise by means of ¹H NMR (in CDCl₃, for signals see Example 1), a content of 2.5% by weight of the sulphosuccinate of the formula

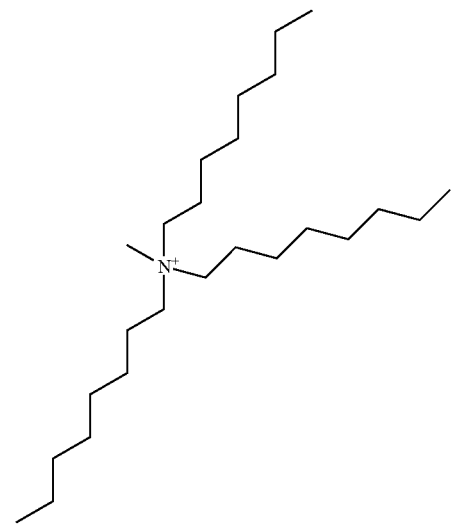

in the solution was found, i.e. 4.5% by weight based on the mixture of the borates.

Total washes: 5

Intermediate phases: 0

Compared to Example 1, it is shown here that the cation exchange does not take place in the required manner when the ammonium salt, in spite of an equal number of carbon atoms (25), does not bear at least one inventive $C_{14}$- to $C_{22}$-alkyl radical.

Materials Used:

Materials Used for the Photopolymer Layers:

Component A experimental product from Bayer MaterialScience AG, Leverkusen, Germany, preparation described below.

Component B1 (phosphothioyltris(oxy-4,1-phenyleneiminocarbonyloxyethane-2,1-diyl)triacrylate)

experimental product from Bayer MaterialScience AG, Leverkusen, Germany, preparation described below.

Component B2 (2-({[3-(methylsulphanyl)phenyl]carbamoyl}oxy)ethyl prop-2-enoate)

experimental product from Bayer MaterialScience AG, Leverkusen, Germany, preparation described below.

Component C (bis(2,2,3,3,4,4,5,5,6,6,7,7-dodecafluoroheptyl)(2,2,4-trimethylhexane-1,6-diyl)biscarbamate)

experimental product from Bayer MaterialScience AG, Leverkusen, Germany, preparation described below.

Component D

Fascat 4102 0.07%, urethanization catalyst, butyltin tris(2-ethylhexanoate), product from Arkema GmbH, Düsseldorf, Germany.

BYK® 310:

silicone-based surface additive from BYK-Chemie GmbH, Wesel, 25% solution in xylene Component E1

Dye 1=C. I. Basic Blue 3 (as bis(2-ethylhexyl)sulphosuccinate) 0.26%, dye 2=Safranin O (as bis(2-ethylhexyl)sulphosuccinate) 0.13% and dye 3=Astrazon Orange G (as bis(2-ethylhexyl)sulphosuccinate) 0.13% with one of the borates 1.5%, dissolved as a solution in 5.8% ethyl acetate. Percentages are based on the overall formulation of the medium.

Component E2

Dye 2=Safranin O (as bis(2-ethylhexyl)sulphosuccinate) 0.2% with one of the borates 1.5%, dissolved as a solution in 5.8% ethyl acetate. Percentages are based on the overall formulation of the medium.

The three dyes were prepared by the process known from WO2012062655.

Borates:

Borate 1 (Inventive)

prepared according to Example 1.

Borate 2 (Noninventive):

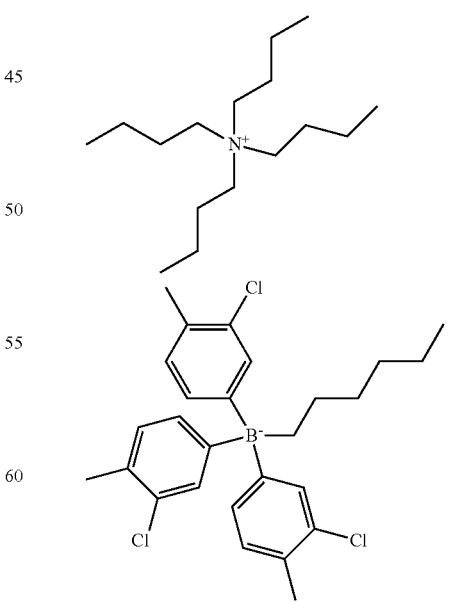

contains 0.3% tetraarylborate of the formula

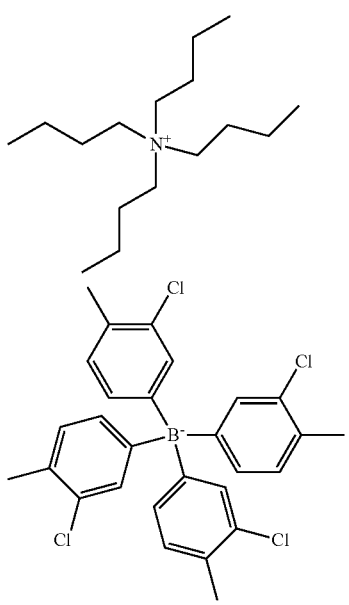

m.p.=119-121° C., no $T_g$

This compound is known from U.S. Pat. No. 6,919,159, Example b-5, and was prepared analogously to DE 196 48 282, Example 2, Method B, using 1-bromo-3-chloro-4-methylbenzene rather than 1-bromo-4-chlorobenzene.

Component F ethyl acetate (CAS No. 141-78-6).

Component G

Desmodur® N 3900, commercial product from Bayer MaterialScience AG, Leverkusen, Germany, hexane diisocyanate-based polyisocyanate, proportion of iminooxadiazinedione at least 30%, NCO content: 23.5%.

Test Methods:

Measurement of Dry Layer Thickness of the Photopolymers

The physical layer thickness was determined with commercial white light interferometers, for example the instrument FTM-Lite NIR film thickness gauge from Ingenieursbüro Fuchs.

The determination of the layer thickness was based on the principle of interference phenomena in thin layers. This involved superimposition of light waves which have been reflected at two interfaces of different optical density. The undistorted superimposition of the reflected component beams led to periodic brightening and quenching in the spectrum of a white continuum radiator (for example halogen lamp). This superimposition is called interference by the person skilled in the art. The interference spectra were measured and evaluated mathematically.

Solids Content

About 1 g of the sample was applied in an uncoated can lid and distributed adequately by means of a paper clip. The can lid and paper clip had been weighed beforehand. The sample together with the paper clip and can lid were dried in an oven at 125° C. for one hour. The solids content was calculated as follows: (final tare weight)*100/(starting tare weight).

Viscosity

The viscosities reported were determined to DIN EN ISO 3219/A.3 at 23° C. and a shear rate of 40 s$^{-1}$.

Isocyanate Content (NCO Content)

The NCO values (isocyanate contents) reported were determined to DIN EN ISO 11909.

Preparation Methods for Further Starting Materials for the Holographic Media

Preparation of Polyol Component A

A 1 l flask was initially charged with 0.18 g of tin octoate, 374.8 g of ε-caprolactone and 374.8 g of a difunctional polytetrahydrofuran polyether polyol (equivalent weight 500 g/mol OH), which were heated to 120° C. and kept at this temperature until the solids content (proportion of nonvolatile constituents) was 99.5% by weight or higher. Subsequently, the mixture was cooled and the product was obtained as a waxy solid.

Preparation of Component B1 (phosphothioyltris (oxy-4,1-phenyleneiminocarbonyloxyethane-2,1-diyl)triacrylate)

A 500 ml round-bottom flask was initially charged with 0.1 g of 2,6-di-tert-butyl-4-methylphenol, 0.05 g of dibutyltin dilaurate (Desmorapid® Z, Bayer MaterialScience AG, Leverkusen, Germany) and and 213.07 g of a 27% solution of tris(p-isocyanatophenyl) thiophosphate in ethyl acetate (Desmodur® RFE, product from Bayer MaterialScience AG, Leverkusen, Germany), which were heated to 60° C. Subsequently, 42.37 g of 2-hydroxyethyl acrylate were added dropwise and the mixture was still kept at 60° C. until the isocyanate content had fallen below 0.1%. This was followed by cooling and complete removal of the ethyl acetate under reduced pressure. The product was obtained as a semicrystalline solid.

Preparation of Component B2 (2-({[3-(methylsulphanyl)phenyl]carbamoyl}oxy)ethyl prop-2-enoate)

A 100 ml round-bottom flask was initially charged with 0.02 g of 2,6-di-tert-butyl-4-methylphenol, 0.01 g of Desmorapid® Z, 11.7 g of 3-(methylthio)phenyl isocyanate and initially charged, and the mixture was heated to 60° C. Subsequently, 8.2 g of 2-hydroxyethyl acrylate were added dropwise and the mixture was still kept at 60° C. until the isocyanate content had fallen below 0.1%. This was followed by cooling. The product was obtained as a pale yellow liquid.

Preparation of Additive C (bis(2,2,3,3,4,4,5,5,6,6,7,7-dodecafluoroheptyl)(2,2,4-trimethylhexane-1,6-diyl)biscarbamate)

A 25 ml round-bottom flask was initially charged with 0.02 g of Desmorapid® Z and 3.60 g of 2,4,4-trimethylhexane 1,6-diisocyanate (TMDI), and the mixture was heated to 70° C. Subsequently, 11.39 g of 2,2,3,3,4,4,5,5,6,6,7,7-dodecafluoroheptan-1-ol were added dropwise and the mixture was still kept at 70° C. until the isocyanate content had fallen below 0.1%. This was followed by cooling. The product was obtained as a colourless oil.

Production of Holographic Media on a Film Coating System

There follows a description of the continuous production of holographic media in the form of films of inventive and noninventive photopolymer formulations.

There follows a description of the continuous production of holographic media in the form of films of inventive and noninventive photopolymer formulations.

Figure 1:
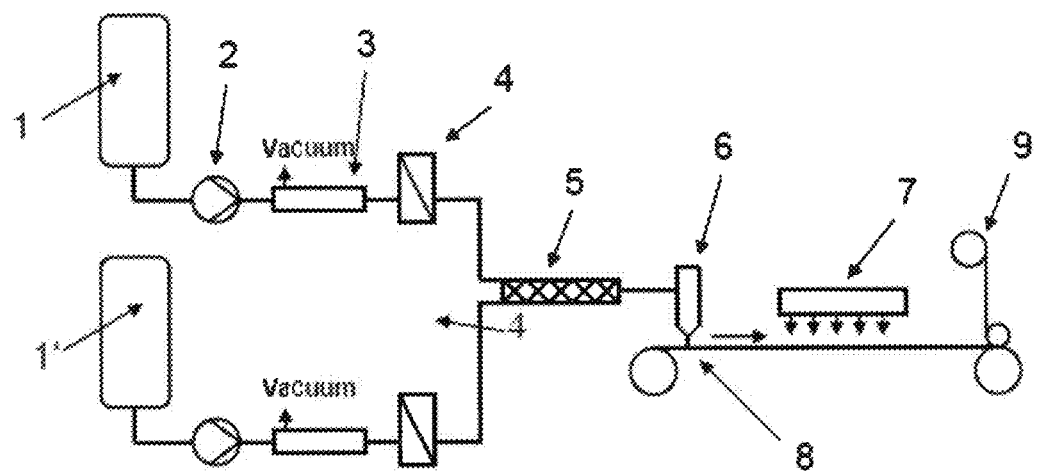
FIG. 1 shows the schematic structure of the coating system used.

For the production, the film coating system shown in FIG. 1 was used, and the individual components are assigned the reference numerals which follow. FIG. 1 shows the schematic structure of the coating system used. In the figure, the individual components have the following reference numerals:

1 reservoir vessel
2 metering unit
3 vacuum devolatilization unit
4 filter
5 static mixer
6 coating unit
7 air circulation dryer
8 carrier substrate
9 covering layer To produce the photopolymer formulation, a mixture of 138 g of writing monomer B1 and 138 g of writing monomer B2, 191 g of additive C, 0.6 g of catalyst D and 2.55 g of BYK® 310 surface-active additive and 101 g of component F were added to and mixed with 304.3 g of polyol component A in a stepwise manner. Subsequently, 66.5 g of a solution of component E1 or E2 were added to the mixture in the dark and mixed, so as to obtain a clear solution. If necessary, the formulation was heated at 60° C. for a short period in order to bring the starting materials into solution more quickly. This mixture was introduced into one of the two reservoir vessels 1 of the coating system. The polyisocyanate component G was introduced into the second reservoir vessel 1'. The two components were then each conveyed by means of the metering units 2 in a ratio of 942.2 (components A to F) to 57.8 (component G) to the vacuum devolatilization unit 3 and devolatilized. From here, they were then each passed through the filters 4 into the static mixer 5, in which the components were mixed to give the photopolymer formulation. The liquid material obtained was then fed to the coating unit 6.

The coating unit 6 in the present case was a doctor blade system known to those skilled in the art. Alternatively, however, it is also possible to use a slot die. With the aid of the coating unit 6, the photopolymer formulation was applied at a processing temperature of 20° C. to a carrier substrate 8 in the form of a 36 μm-thick polyethylene terephthalate film, and dried in an air circulation dryer 7 at a crosslinking temperature of 80° C. for 5.8 minutes. This gave a medium in the form of a film, which was then provided with a 40 μm-thick polyethylene film as covering layer 9 and wound up.

The desired target layer thickness of the film was preferably between 10 to 60 μm.

The production speed was preferably in the range from 0.2 m/min to 300 m/min and more preferably in the range from 1.0 m/min to 50 m/min.

The layer thickness achieved in the film was 18 μm±1 μm.

Test Methods

Measurement of the holographic properties of diffraction efficiency DE and refractive index contrast Δn of the holographic media by means of twin-beam interference in a reflection arrangement.

Figure 2:
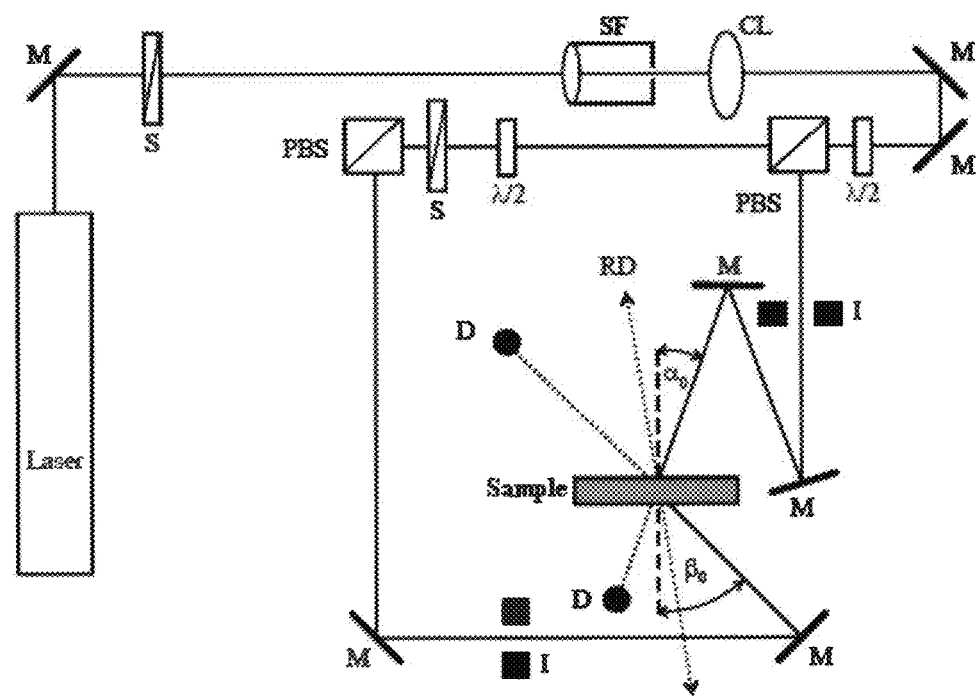
FIG. 2 shows the geometry of a holographic media tester (HMT) at λ=532 nm (DPSS laser).

A holographic test setup as shown in FIG. 2 was used to measure the diffraction efficiency (DE) of the media. The beam of a DPSS laser (emission wavelength 532 nm) was converted to a parallel homogeneous beam with the aid of the spatial filter (SF) and together with the collimation lens (CL). The final cross sections of the signal and reference beam are fixed by the iris diaphragms (I). The diameter of the iris diaphragm opening is 0.4 cm. The polarization-dependent beam splitters (PBS) split the laser beam into two coherent beams of identical polarization. By means of the λ/2 plates, the power of the reference beam was set to 0.87 mW and the power of the signal beam to 1.13 mW. The powers were determined using the semiconductor detectors (D) with the sample removed. The angle of incidence ($\alpha_0$) of the reference beam is −21.8°; the angle of incidence ($\beta_0$) of the signal beam is 41.8°. The angles are measured proceeding from the sample normal to the beam direction. According to FIG. 2, therefore, $\alpha_0$ has a negative sign and $\beta_0$ a positive sign. At the location of the sample (medium), the interference field of the two overlapping beams produced a pattern of light and dark strips parallel to the angle bisectors of the two beams incident on the sample (reflection hologram). The strip spacing Λ, also called grating period, in the medium is ~225 nm (the refractive index of the medium assumed to be ~1.504).

FIG. 2 shows the geometry of a holographic media tester (HMT) at λ=532 nm (DPSS laser): M=mirror, S=shutter, SF=spatial filter, CL=collimator lens, λ/2=λ/2 plate, PBS=polarization-sensitive beam splitter, D=detector, I=iris diaphragm, $\alpha_0$=−21.8°, $\beta_0$=41.8° are the angles of incidence of the coherent beams measured outside the sample (outside the medium). RD=reference direction of the turntable.

Holograms were recorded in the medium in the following manner:

Both shutters (S) are opened for the exposure time t.
Thereafter, with the shutters (S) closed, the medium is allowed 5 minutes for the diffusion of the as yet unpolymerized writing monomers.

The holograms recorded were then reconstructed in the following manner. The shutter of the signal beam remained closed. The shutter of the reference beam was opened. The iris diaphragm of the reference beam was closed to a diameter of <1 mm. This ensured that the beam was always completely within the previously recorded hologram for all angles of rotation (Ω) of the medium. The turntable, under computer control, swept over the angle range from $\Omega_{min}$ to $\Omega_{max}$ with an angle step width of 0.05°. Ω is measured from the sample normal to the reference direction of the turntable. The reference direction of the turntable is obtained when the angles of incidence of the reference beam and of the signal beam have the same absolute value on recording of the hologram, i.e. $\alpha_0$=−31.8° and $\beta_0$=31.8°. In that case, $\Omega_{recording}$=0°. When $\alpha_0$=−21.8° and $\beta_0$=41.8°, $\Omega_{recording}$ is therefore 10°. In general, for the interference field in the course of recording of the hologram:

$$\alpha_0 = \theta_0 + \Omega_{recording}.$$

$\theta_0$ is the semiangle in the laboratory system outside the medium and, in the course of recording of the hologram:

$$\theta_0 = \frac{\alpha_0 - \beta_0}{2}.$$

Thus, in this case, $\theta_0 = -31.8°$. At each setting for the angle of rotation $\Omega$, the powers of the beam transmitted in the zeroth order were measured by means of the corresponding detector D, and the powers of the beam diffracted in the first order by means of the detector D. The diffraction efficiency was calculated at each setting of angle $\Omega$ as the quotient of:

$$\eta = \frac{P_D}{P_D + P_T}$$

$P_D$ is the power in the detector for the diffracted beam and $P_T$ is the power in the detector for the transmitted beam.

By means of the process described above, the Bragg curve, which describes the diffraction efficiency $\eta$ as a function of the angle of rotation $\Omega$ for the recorded hologram, was measured and saved on a computer. In addition, the intensity transmitted into the zeroth order was also recorded against the angle of rotation $\Omega$ and saved on a computer.

The maximum diffraction efficiency (DE=$\eta_{max}$) of the hologram, i.e. the peak value thereof, was determined at $\Omega_{reconstruction}$. In some cases, it was necessary for this purpose to change the position of the detector for the diffracted beam in order to determine this maximum value.

The refractive index contrast $\Delta n$ and the thickness d of the photopolymer layer were now determined by means of coupled wave theory (see: H. Kogelnik, The Bell System Technical Journal, Volume 48, November 1969, Number 9 page 2909-page 2947) from the measured Bragg curve and the variation of the transmitted intensity with angle. In this context, it should be noted that, because of the shrinkage in thickness which occurs as a result of the photopolymerization, the strip spacing $\Delta'$ of the hologram and the orientation of the strips (slant) can differ from the strip spacing $\Delta$ of the interference pattern and the orientation thereof. Accordingly, the angle $\alpha_0'$ and the corresponding angle of the turntable $\Omega_{reconstruction}$ at which maximum diffraction efficiency is achieved will also differ from $\alpha_0$ and from the corresponding $\Omega_{recording}$. This alters the Bragg condition. This alteration is taken into account in the evaluation process. The evaluation process is described hereinafter:

All geometric parameters which relate to the recorded hologram and not to the interference pattern are shown as parameters with primes.

For the Bragg curve $\eta(\Omega)$ of a reflection hologram, according to Kogelnik:

$$\eta = \begin{cases} \dfrac{1}{1 - \dfrac{1-(\xi/v)^2}{\sin^2\left(\sqrt{\xi^2 - v^2}\right)}}, & \text{for } v^2 - \xi^2 < 0 \\[2ex] \dfrac{1}{1 + \dfrac{1-(\xi/v)^2}{\sinh^2\left(\sqrt{v^2 - \xi^2}\right)}}, & \text{for } v^2 - \xi^2 \geq 0 \end{cases}$$

with:

$$v = \frac{\pi \cdot \Delta n \cdot d'}{\lambda \cdot \sqrt{|c_s \cdot c_r|}}$$

$$\xi = -\frac{d'}{2 \cdot c_s} \cdot DP$$

$$c_s = \cos(\vartheta') - \cos(\Psi') \cdot \frac{\lambda}{n \cdot \Lambda'}$$

$$c_r = \cos(\vartheta')$$

$$DP = \frac{\pi}{\Lambda'} \cdot \left(2 \cdot \cos(\Psi' - \vartheta') - \frac{\lambda}{n \cdot \Lambda'}\right)$$

$$\Psi' = \frac{\beta' + \alpha'}{2}$$

$$\Lambda' = \frac{\lambda}{2 \cdot n \cdot \cos(\Psi' - \alpha')}$$

In the reconstruction of the hologram, as explained analogously above:

$$\vartheta'_0 = \theta_0 + \Omega$$

$$\sin(\vartheta'_0) = n \cdot \sin(\vartheta')$$

Under the Bragg condition, the "dephasing" DP=0. And it follows correspondingly that:

$$\alpha'_0 = \theta_0 + \Omega_{reconstruction}$$

$$\sin(\alpha'_0) = n \cdot \sin(\alpha')$$

The as yet unknown angle $\beta'$ can be determined from the comparison of the Bragg condition of the interference field in the course of recording of the hologram and the Bragg condition in the course of reconstruction of the hologram, assuming that only shrinkage in thickness takes place. It then follows that:

$$\sin(\beta') = \frac{1}{n} \cdot [\sin(\alpha_0) + \sin(\beta_0) - \sin(\theta_0 + \Omega_{reconstruction})]$$

$v$ is the grating thickness, $\xi$ is the detuning parameter and $\psi'$ is the orientation (slant) of the refractive index grating which has been recorded. $\alpha'$ and $\beta'$ correspond to the angles $\alpha_0$ and $\beta_0$ of the interference field in the course of recording of the hologram, except measured in the medium and applying to the grating of the hologram (after shrinkage in thickness). n is the mean refractive index of the photopolymer and was set to 1.504. $\lambda$ is the wavelength of the laser light in the vacuum.

The maximum diffraction efficiency (DE=$\eta_{max}$), when $\xi=0$, is then calculated to be:

$$DE = \tanh^2(v) = \tanh^2\left(\frac{\pi \cdot \Delta n \cdot d'}{\lambda \cdot \sqrt{\cos(\alpha') \cdot \cos(\alpha' - 2\Psi)}}\right)$$

Figure 3:
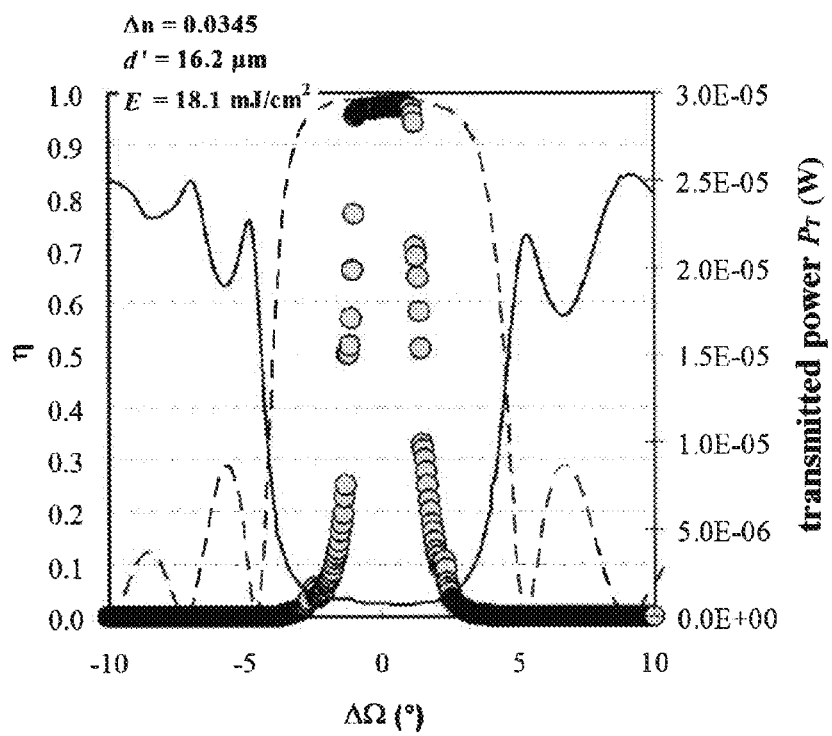
FIG. 3 shows the measured transmitted power $P_T$ (right-hand y-axis) plotted as a solid line against the angle detuning $\Delta\Omega$.

FIG. 3 shows the measured transmitted power $P_T$ (right-hand y-axis) plotted as a solid line against the angle detuning $\Delta\Omega$; the measured diffraction efficiency η (left-hand y-axis) is plotted as filled circles against the angle detuning $\Delta\Omega$ (to the extent allowed by the finite size of the detector), and the fitting to the Kogelnik theory as a broken line (left-hand y-axis).

The measured data for the diffraction efficiency, the theoretical Bragg curve and the transmitted intensity are, as shown in FIG. 3, plotted against the centred angle of rotation $\Delta\Omega = \Omega_{reconstruction} - \Omega = \alpha'_0 - \vartheta'_0$, also called angle detuning.

Since DE is known, the shape of the theoretical Bragg curve, according to Kogelnik, is determined only by the thickness d' of the photopolymer layer. Δn is corrected via DE for a given thickness d' such that measurement and theory for DE are always in agreement. d' is adjusted until the angle positions of the first secondary minima of the theoretical Bragg curve correspond to the angle positions of the first secondary maxima of the transmitted intensity, and there is additionally agreement in the full width at half maximum (FWHM) for the theoretical Bragg curve and for the transmitted intensity.

Since the direction in which a reflection hologram also rotates when reconstructed by means of an Ω scan, but the detector for the diffracted light can cover only a finite angle range, the Bragg curve of broad holograms (small d') is not fully covered in an Ω scan, but rather only the central region, given suitable detector positioning. Therefore, the shape of the transmitted intensity, which is complementary to the Bragg curve, is additionally employed for adjustment of the layer thickness d'.

FIG. 3 shows the plot of the Bragg curve η according to the coupled wave theory (broken line), the measured diffraction efficiency (filled circles) and the transmitted power (black solid line) against the angle detuning $\Delta\Omega$.

For a formulation, this procedure was repeated, possibly several times, for different exposure times t on different media, in order to find the mean energy dose of the incident laser beam in the course of recording of the hologram at which DE reaches the saturation value. The mean energy dose E is calculated as follows from the powers of the two component beams assigned to the angles $\alpha_0$ and $\beta_0$ (reference beam where $P_r = 0.87$ mW and signal beam where $P_s = 1.13$ mW), the exposure time t and the diameter of the iris diaphragm (0.4 cm):

$$E(\mathrm{mJ/cm}^2) = \frac{2 \cdot [P_r + P_s] \cdot t(s)}{\pi \cdot 0.4^2 \ \mathrm{cm}^2}$$

The powers of the component beams were adjusted such that the same power density is attained in the medium at the angles $\alpha_0$ and $\beta_0$ used.

Test Results

Four holographic films were produced:
Inventive:
film 1, containing dyes 1, 2 and 3 and borate 1
film 2, containing dye 2, borate 1
Noninventive:
film A, containing dyes 1, 2 and 3 and borate 2
film B, containing dye 2, borate 2

In order to test the long-term stability thereof, the films were stored at room temperature with exclusion of light for 12 months, and then a hologram was exposed.

The results of the holographic exposure with a green laser (532 nm) are compiled in the following table, Table 1:

TABLE 1

| Film | Δn at 1.99 mJ/cm² | Δn at 3.02 mJ/cm² | Δn at 5.97 mJ/cm² | Δn at 7.96 mJ/cm² | Δn at 15.92 mJ/cm² | Δn at 31.83 mJ/cm² |
|---|---|---|---|---|---|---|
| 1 | 0.0053 | 0.0191 |  | 0.0311 | 0.0339 | 0.0344 |
| A | 0.0000 | 0.0152 |  | 0.0286 | 0.0327 | 0.0338 |
| 2 |  |  | 0.0284 | 0.0325 | 0.0312 | 0.0306 |
| B |  |  | 0.0268 | 0.0284 | 0.0278 | 0.0278 |

It can be seen that the inventive films 1 and 2 give higher refractive index contrasts Δn than the noninventive films A and B. This becomes particularly clear when, as shown in Table 2 below, the quotients Q of the Δn values of the corresponding pairs are considered, where $Q = \Delta n(1)/\Delta n(A)$ and $Q = \Delta n(2)/\Delta n(B)$.

TABLE 2

| Film comparison | Q at 1.99 mJ/cm² | Q at 3.02 mJ/cm² | Q at 5.97 mJ/cm² | Q at 7.96 mJ/cm² | Q at 15.92 mJ/cm² | Q at 31.83 mJ/cm² |
|---|---|---|---|---|---|---|
| 1 over A | ∞ | 1.26 |  | 1.09 | 1.04 | 1.02 |
| 2 over B |  |  | 1.06 | 1.14 | 1.12 | 1.10 |

It can be seen that the inventive film 1 is superior to the noninventive film A, especially at low light doses. It thus exhibits a higher sensitivity. The inventive film 2 is similarly distinctly superior to the noninventive film B, but over a wide range of light doses.

The four films were subjected to a bleaching process after exposure of a hologram. A two-stage bleaching process was employed. First of all, the films were exposed to radiation from a high-pressure mercury vapour lamp of the Dynax 2000-EC type for 45 seconds, at a power density at the surface of the film of 75 mW/cm² and a dose of 7 J/cm2. This was followed immediately thereafter by full-area illumination by means of a CF2000 UV-LED system from Clearstone Technologies at a wavelength of 365 nm, at a power density at the surface of the film of 40 mW/cm² for 300 seconds and an accumulated dose of 12 J/cm².

Figure 4:
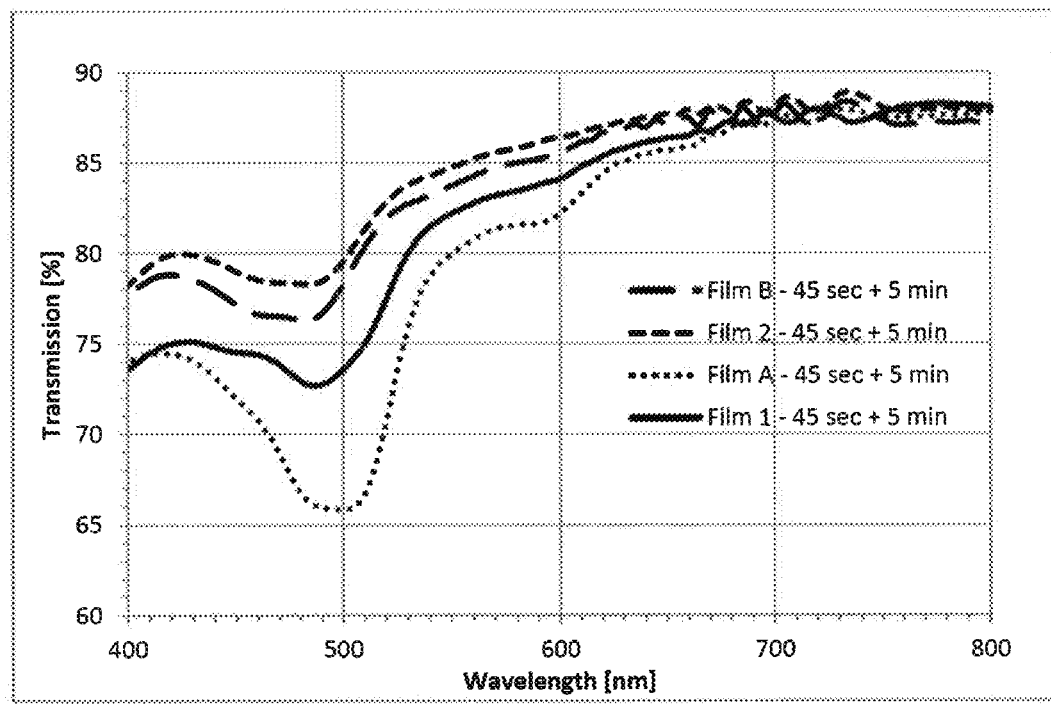
FIG. 4 shows the transmission spectra of films 1, 2, A and B after bleaching.
Figure 5:
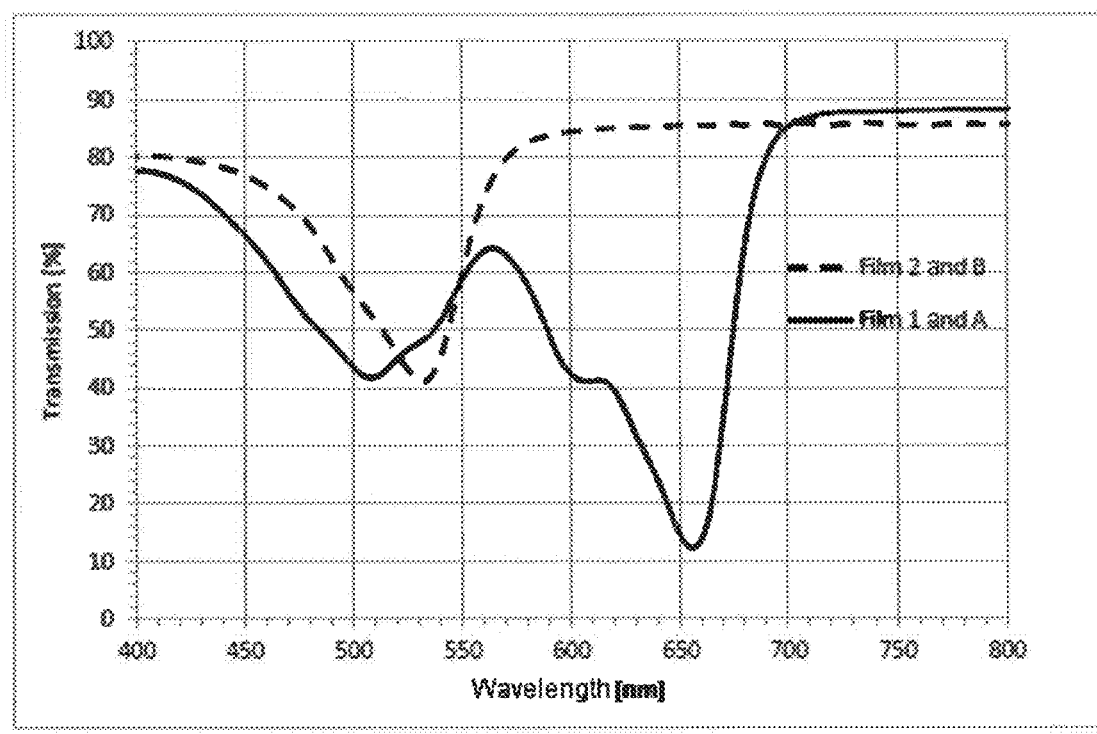
FIG. 5 shows the transmission spectra of films 1, 2, A and B before bleaching.

The results can be found in FIG. 4. This shows the transmission spectra of films 1, 2, A and B after bleaching. FIG. 5 contains the transmission spectra of films 1, 2, A and B before bleaching.

It can be seen that the inventive films 1 and 2 give a higher transmission after bleaching than the noninventive films A and B. This difference is especially marked in the region of shorter wavelengths and thus leads to lower "residual yellowness" in the inventive films. Consequently, films 1 and 2 have distinctly improved bleachability.

The invention claimed is:

1. A photopolymer formulation comprising a component reactive toward isocyanates, a polyisocyanate component, a writing monomer and a photoinitiator consisting essentially of at least one dye and a coinitiator, wherein the coinitiator consists essentially of at least one substance of the formula (Ia)

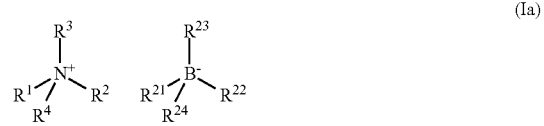

in which $R^1$ is an optionally branched $C_{14}$- to $C_{22}$-alkyl radical, $R^2$ is an optionally branched and/or optionally substituted $C_8$- to $C_{22}$-alkyl radical, a cyclohexyl or cycloheptyl radical, a $C_7$- to $C_{10}$-aralkyl radical, or a phenyl radical substituted by nonionic radicals, and $R^3$ and $R^4$ are each independently an optionally branched and/or optionally substituted $C_1$- to $C_5$-alkyl radical or $R^1$ is an optionally branched $C_{14}$- to $C_{22}$-alkyl radical, $R^2$ is an optionally branched and/or optionally substituted $C_8$- to $C_{22}$-alkyl radical or a $C_7$- to $C_{10}$-aralkyl radical and $R^3$ and $R^4$ together form a —$(CH_2)_4$—, —$(CH_2)_5$— or —$(CH_2)_2$—O—$(CH_2)_2$— bridge or $R^1$ is an optionally branched $C_{14}$- to $C_{22}$-alkyl radical, $R^2$, $R^3$ and $R^4$ together with the $N^+$ form an imidazole or pyridine ring substituted at least by one radical selected from $C_1$- to $C_8$-alkyl, $C_1$- to $C_8$-alkoxy, $C_5$- to $C_7$-cycloalkyl, benzyl or phenyl and in which $R^{21}$ is an optionally substituted $C_1$- to $C_{22}$-alkyl, $C_3$- to $C_{22}$-alkenyl, $C_5$- to $C_7$-cycloalkyl or $C_7$- to $C_{13}$-aralkyl radical, and $R^{22}$ to $R^{24}$ are each independently a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and phenoxy.

2. The photopolymer formulation according to claim 1, wherein the coinitiator has a glass transition temperature $T_g$ of ≤0° C.

3. The photopolymer formulation according to claim 1, wherein the coinitiator additionally contains at least one substance of the formula (Ib)

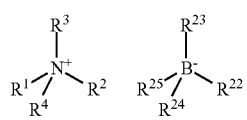

(Ib)

in which $R^1$ to $R^4$ are each as defined in claim 1 and $R^{22}$ to $R^{25}$ are each independently a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and phenoxy.

4. The photopolymer formulation according to claim 3, wherein the coinitiator contains the substances of the formulae (Ia) and (Ib) in a molar ratio of 80:20 to 99.99:0.01.

5. The photopolymer formulation according to claim 3, wherein the coinitiator contains the substances (IIIa) and (IIIb) in the same ratio relative to one another as the substances (Ia) and (Ib).

6. The photopolymer formulation according to claim 1, wherein the coinitiator additionally contains substances of the formulae (IIIa) and optionally (IIIb)

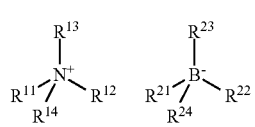

(IIIa)

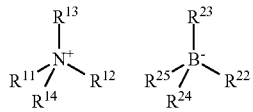

(IIIb)

in which $R^{11}$ to $R^{14}$ are each independently $C_1$- to $C_4$-alkyl and $R^{21}$ to $R^{24}$ are each as defined in claim 1 and $R^{25}$ is a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and phenoxy.

7. The photopolymer formulation according to claim 5, wherein the coinitiator contains the substances of the formulae (Ia) and (Ib) in a molar ratio of 80:20 to 99.99:0.01, wherein the coinitiator contains 1 to 5% by weight, based on the total amount of coinitiator, of salts of the formula (II).

8. The photopolymer formulation according to claim 1, wherein the coinitiator additionally contains at least one salt of the formula (II)

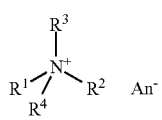

(II)

in which $An^-$ is an anion having an AC log P in the range of 3-6 and $R^1$ to $R^4$ are each as defined in claim 1.

9. The photopolymer formulation according to claim 8, wherein the coinitiator contains 0.01 to 10% by weight, based on the total amount of coinitiator, of salts of the formula (II).

10. The photopolymer formulation according to claim 6, wherein the molar ratio of the substances (IIIa) and optionally (IIIb) to the sum total of the substances (Ia) and optionally (Ib) is ≤15:85.

11. A holographic medium comprising the photopolymer formulation according to claim 1 provided on a substrate.

12. A laminate structure comprising a carrier substrate, a holographic medium according to claim 11 applied thereto, and optionally a covering layer applied to the opposite side of the holographic medium from the carrier substrate.

13. A process for producing a holographic medium, comprising (I) preparing the photopolymer formulation according to claim 1 by mixing all the constituents, (II) converting the photopolymer formulation to a form desired for the holographic medium at a processing temperature in the range of from 20 to 40° C. and (III) curing in the desired form with urethane formation at a crosslinking temperature above the processing temperature.

14. A photopolymer formulation comprising a component reactive toward isocyanates, a polyisocyanate component, a writing monomer and a photoinitiator consisting essentially of at least one dye and a coinitiator, wherein the coinitiator consists essentially of at least one substance of the formula (Ia)

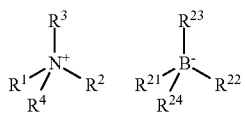 (Ia)

in which
$R^1$ is an optionally branched $C_{14}$- to $C_{22}$-alkyl radical,
$R^2$ is an optionally branched and/or optionally substituted $C_8$- to $C_{22}$-alkyl radical, a cyclohexyl or cycloheptyl radical, a $C_7$- to $C_{10}$-aralkyl radical, or a phenyl radical substituted by nonionic radicals, and
$R^3$ and $R^4$ are each independently an optionally branched and/or optionally substituted $C_1$- to $C_5$-alkyl radical or
$R^1$ is an optionally branched $C_{14}$- to $C_{22}$-alkyl radical,
$R^2$ is an optionally branched and/or optionally substituted $C_8$- to $C_{22}$-alkyl radical or a $C_7$- to $C_{10}$-aralkyl radical and
$R^3$ and $R^4$ together form a $—(CH_2)_4—$, $—(CH_2)_5—$ or $—(CH_2)_2—O—(CH_2)_2—$ bridge or
$R^1$ is an optionally branched $C_{14}$- to $C_{22}$-alkyl radical,
$R^2$, $R^3$ and $R^4$ together with the $N^+$ form an imidazole or pyridine ring substituted at least by one radical selected from $C_1$- to $C_8$-alkyl, $C_1$- to $C_8$-alkoxy, $C_5$- to $C_7$-cycloalkyl, benzyl or phenyl
and in which
$R^{21}$ is an optionally substituted $C_1$- to $C_{22}$-alkyl, $C_3$- to $C_{22}$-alkenyl, $C_5$- to $C_7$-cycloalkyl or $C_7$- to $C_{13}$-aralkyl radical, and
$R^{22}$ to $R^{24}$ are each independently a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and phenoxy,
wherein the coinitiator additionally contains at least one salt of the formula (II)

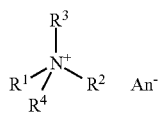 (II)

in which
$An^-$ is an anion having an AC log P in the range of 3-6 and
$R^1$ to $R^4$ are each as above,
and wherein the coinitiator additionally contains substances of the formulae (IIIa) and optionally (IIIb)

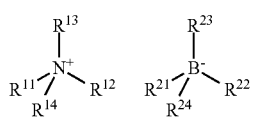 (IIIa)

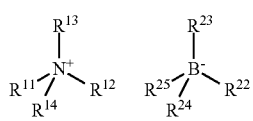 (IIIb)

in which
$R^{11}$ to $R^{14}$ are each independently $C_1$- to $C_4$-alkyl and
$R^{21}$ to $R^{24}$ are each as defined in claim 1 and
$R^{25}$ is a $C_6$- to $C_{10}$-aryl radical optionally substituted by at least one radical selected from halogen, $C_1$- to $C_4$-alkyl, trifluoromethyl, $C_1$- to $C_4$-alkoxy, trifluoromethoxy, phenyl and phenoxy.

\* \* \* \* \*